US011802294B2

(12) United States Patent
Abeliovich et al.

(10) Patent No.: US 11,802,294 B2
(45) Date of Patent: Oct. 31, 2023

(54) GENE THERAPIES FOR LYSOSOMAL DISORDERS

(71) Applicant: Prevail Therapeutics, Inc., New York, NY (US)

(72) Inventors: Asa Abeliovich, New York, NY (US); Laura Heckman, New York, NY (US); Herve Rhinn, New York, NY (US)

(73) Assignee: Prevail Therapeutics, Inc., New York, NY (US)

( * ) Notice: Subject to any disclaimer, the term of this patent is extended or adjusted under 35 U.S.C. 154(b) by 696 days.

(21) Appl. No.: 16/753,016

(22) PCT Filed: Oct. 3, 2018

(86) PCT No.: PCT/US2018/054225

§ 371 (c)(1),
(2) Date: Apr. 2, 2020

(87) PCT Pub. No.: WO2019/070893

PCT Pub. Date: Apr. 11, 2019

(65) Prior Publication Data

US 2020/0231954 A1 Jul. 23, 2020

Related U.S. Application Data

(60) Provisional application No. 62/567,296, filed on Oct. 3, 2017.

(51) Int. Cl.

| | |
|---|---|
| ***C12N 15/864*** | (2006.01) |
| ***A61K 48/00*** | (2006.01) |
| ***C12N 15/113*** | (2010.01) |
| ***C12N 15/12*** | (2006.01) |
| ***A61K 31/7115*** | (2006.01) |
| ***C12N 15/52*** | (2006.01) |
| ***A61P 25/16*** | (2006.01) |
| ***C12N 15/861*** | (2006.01) |
| ***C07K 14/435*** | (2006.01) |
| ***C07K 14/705*** | (2006.01) |
| ***C12N 7/00*** | (2006.01) |
| ***C12N 9/24*** | (2006.01) |
| ***C12N 15/86*** | (2006.01) |
| *A61K 9/00* | (2006.01) |

(52) U.S. Cl.

CPC ........ *C12N 15/861* (2013.01); *A61K 48/0058* (2013.01); *C07K 14/435* (2013.01); *C07K 14/70596* (2013.01); *C12N 7/00* (2013.01); *C12N 9/2402* (2013.01); *C12N 15/113* (2013.01); *C12N 15/86* (2013.01); *C12Y 302/01045* (2013.01); *A61K 9/0019* (2013.01); *A61K 48/00* (2013.01); *C12N 2310/14* (2013.01); *C12N 2310/141* (2013.01); *C12N 2710/14043* (2013.01); *C12N 2750/14143* (2013.01)

(58) Field of Classification Search

None

See application file for complete search history.

(56) References Cited

U.S. PATENT DOCUMENTS

| | | | |
|---|---|---|---|
| 5,879,680 | A | 3/1999 | Ginns et al. |
| 6,521,225 | B1 | 2/2003 | Srivastava et al. |
| 6,696,272 | B1 | 2/2004 | Mahuran et al. |
| 7,172,893 | B2 | 2/2007 | Rabinowitz |
| 7,452,716 | B2 | 11/2008 | Yew |
| 8,389,487 | B2 | 3/2013 | Bohn et al. |
| 8,454,954 | B2 | 6/2013 | Schlossmacher et al. |
| 8,962,273 | B2 | 2/2015 | Reczek |
| 9,034,836 | B2 | 5/2015 | Dodge et al. |
| 9,290,759 | B2 | 3/2016 | Abeliovich et al. |
| 9,347,107 | B2 | 5/2016 | Lai et al. |
| 10,213,494 | B2 | 2/2019 | Schlossmacher et al. |
| 10,837,028 | B2 | 11/2020 | Abeliovich et al. |
| 11,060,113 | B2 | 7/2021 | Abeliovich et al. |
| 2003/0100115 | A1 | 5/2003 | Raj et al. |
| 2003/0133924 | A1 | 7/2003 | Canfield |
| 2006/0292117 | A1 | 12/2006 | Loiler et al. |
| 2008/0003204 | A1 | 1/2008 | Flotte et al. |
| 2015/0284472 | A1 | 8/2015 | Sardi et al. |
| 2016/0237414 | A1 | 8/2016 | Grabowski et al. |

(Continued)

FOREIGN PATENT DOCUMENTS

| | | | |
|---|---|---|---|
| EP | 3091087 | A1 | 11/2016 |
| EP | 3701030 | A1 | 9/2020 |

(Continued)

OTHER PUBLICATIONS

Zhang et al, Disease-modifying therapeutic directions for Lewy-Body dementias, Front. Neurosci.2015, pp. 1-9.*

(Continued)

*Primary Examiner* — Maria Marvich
(74) *Attorney, Agent, or Firm* — Cooley LLP; Ivor Elrifi

(57) ABSTRACT

The disclosure relates, in some aspects, to compositions and methods for treatment of diseases associated with aberrant lysosomal function, for example Parkinson's disease and Gaucher disease. In some embodiments, the disclosure provides expression constructs comprising a transgene encoding beta-Glucocerebrosidase (GBA) or a portion thereof, Lysosomal Membrane Protein 2 (LIMP2), Prosaposin, or any combination of the foregoing. In some embodiments, the disclosure provides methods of Parkinson's disease by administering such expression constructs to a subject in need thereof.

44 Claims, 26 Drawing Sheets

Specification includes a Sequence Listing.

(56) References Cited

U.S. PATENT DOCUMENTS

| | | | |
|---|---|---|---|
| 2016/0264965 | A1 | 9/2016 | Mouradian et al. |
| 2017/0035860 | A1 | 2/2017 | Flynn |
| 2018/0071373 | A1 | 3/2018 | Melvor et al. |
| 2018/0147300 | A1 | 5/2018 | Park et al. |
| 2019/0038773 | A1 | 2/2019 | Esteves et al. |
| 2019/0055578 | A1 | 2/2019 | Sah et al. |
| 2019/0282662 | A1 | 9/2019 | Kay et al. |
| 2019/0328906 | A1 | 10/2019 | Chen Plotkin et al. |
| 2020/0071726 | A1 | 3/2020 | Abeliovich et al. |
| 2020/0231970 | A1 | 7/2020 | Abeliovich et al. |
| 2020/0338148 | A1 | 10/2020 | Abeliovich et al. |
| 2021/0010032 | A1 | 1/2021 | Abeliovich et al. |
| 2021/0332385 | A1 | 10/2021 | Abeliovich et al. |
| 2022/0211871 | A1 | 7/2022 | Abeliovich et al. |

FOREIGN PATENT DOCUMENTS

| | | | |
|---|---|---|---|
| WO | WO-0183692 | A2 | 11/2001 |
| WO | WO 02/24932 | A2 | 3/2002 |
| WO | WO 2004/098648 | A1 | 11/2004 |
| WO | WO-2009079399 | A2 | 6/2009 |
| WO | WO 2012/027558 | A2 | 3/2012 |
| WO | WO 2012/027713 | A2 | 3/2012 |
| WO | WO 2014/071282 | A1 | 5/2014 |
| WO | WO 2014/186579 | A1 | 11/2014 |
| WO | WO 2016/081927 | A2 | 3/2016 |
| WO | WO 2017/077451 | A1 | 5/2017 |
| WO | WO 2017/136202 | A1 | 8/2017 |
| WO | WO 2019/070891 | A1 | 4/2019 |
| WO | WO 2019/070894 | A1 | 4/2019 |
| WO | WO-2020210615 | A1 | 10/2020 |
| WO | WO-2020210713 | A1 | 10/2020 |

OTHER PUBLICATIONS

Orme et al,The Genetics of Dementia with Lewy Bodies: Current Understanding and Future Directions, Current Neurology and Neuroscience Reports (2018), pp. 1-13.*

Fischell and Fishman, A Multifaceted Approach to Optimizing AAV Delivery to the Brain for the Treatment of Neurodegenerative Diseases, Frontiers in Neuroscience, pp. 1-20.*

Hudry et al, Therapeutic AAV Gene Transfer to the Nervous System: A Clinical Reality, Neuron 101, 2019, pp. 839-862 and p. 263.*

Marchi et al, Delivery of therapeutic AAV9 vectors via cisterna magna to treat neurological disorders, Cell Press, Trends in Molecular Medicine, 2022, p. 79-80.*

Garcia-Gomez, M., et al., "Modelling Gaucher Disease Through Interference RNA Technology," Human Gene Therapy, Sep. 1, 2015, 26(9), PO37, A22-A23.

Khodr, et al. "Targeting alpha-synuclein with a microRNA-embedded silencing vector in the rat substantia nigra: Positive and negative effects," Brain Research, Mar. 6, 2014, 1550:47-60 (23 pages total).

Naso, et al., "Adeno-Associated Virus (AAV) as a Vector for Gene Therapy," BioDrugs, 2017, 31, 317-334.

Sinclair, et al., "Synonymous codon usage bias and the expression of human glucocerebrosidase in the methylotrophic yeast, *Pichia pastrois*," Protein Expression and Purification, 2002, 26, 96-105.

Wang, et al., "Adeno-Associated Virus Type 2 DNA Replication in Vivo: Mutation Analyses of the D Sequence in Viral Inverted Terminal Repeats," Journal of Virology, Apr. 1997, 71(4), 3077-3082.

GenBank Accession No. NP_000148.2 "lysosomal acid glucosylceramidase isoform 1 precursor [*Homo sapiens*]" Jan. 8, 2020 [online].

GenBank Accession No. NP_005497.1 "lysosome membrane protein 2 isoform 1 precursor [*Homo sapiens*]" Jan. 1, 2020 [online].

GenBank Accession No. NP_002769.1 "prosaposin isoform a preproprotein [*Homo sapiens*]" Sep. 27, 2019 [online].

GenBank Accession No. NP_001191184.1 "lysosome membrane protein 2 isoform 2 precursor [*Homo sapiens*]" Jan. 4, 2020 [online].

GenBank Accession No. AAH01503.1 "Prosaposin [*Homo sapiens*]" Aug. 4, 2008 [online].

GenBank Accession No. AAH07612.1 "Prosaposin [*Homo sapiens*]" Aug. 4, 2008 [online].

GenBank Accession No. AAH04275.1 "Prosaposin [*Homo sapiens*]" Aug. 4, 2008 [online].

GenBank Accession No. AAA60303.1 "Prosaposin [*Homo sapiens*]" Jan. 9, 1995 [online].

GenBank Accession No. AAP36904.1 "*Homo sapiens* glucosidase, beta; acid (includes glucosylceramidase), partial [synthetic construct]" Jul. 25, 2016 [online].

GenBank Accession No. BT008212.1 "Synthetic construct *Homo sapiens* glucosidase, beta; acid (includes glucosylceramidase) mRNA, partial cds" Jul. 25, 2016 [online].

GenBank Accession No. NP_001005742.1 "lysosomal acid glucosylceramidase isoform 1 precursor [*Homo sapiens*]" Nov. 11, 2019 [online].

GenBank Accession No. NP_001165282.1 "lysosomal acid glucosylceramidase isoform 2 [*Homo sapiens*]" Nov. 11, 2019 [online].

GenBank Accession No. NP_001165283.1 "lysosomal acid glucosylceramidase isoform 3 [*Homo sapiens*]" Nov. 11, 2019 [online].

GenBank Accession No. NP_065995.1 "non-lysosomal glucosylceramidase isoform 1 [*Homo sapiens*]" Aug. 22, 2019 [online].

GenBank Accession No. NP_000144.2 "galactocerebrosidase isoform a precursor [*Homo sapiens*]" Sep. 26, 2019 [online].

GenBank Accession No. NP_001899.1 "cathepsin B isoform 1 preproprotein [*Homo sapiens*]" Jan. 27, 2020 [online].

GenBank Accession No. NP_000534.3 "sphingomyelin phosphodiesterase isoform 1 precursor [*Homo sapiens*]" Jan. 13, 2020 [online].

GenBank Accession No. NP_003920.1 "ras-related protein Rab-7L1 isoform 1 [*Homo sapiens*]" Dec. 31, 2019 [online].

GenBank Accession No. NP_060676.2 "vacuolar protein sorting-associated protein 35 [*Homo sapiens*]" Oct. 11, 2019 [online].

GenBank Accession No. NP_689669.2 "interleukin-34 isoform 1 precursor [*Homo sapiens*]" Dec. 25, 2019 [online].

GenBank Accession No. NP_061838.1 "triggering receptor expressed on myeloid cells 2 precursor isoform 1 precursor [*Homo sapiens*]" Feb. 2, 2020 [online].

GenBank Accession No. NP_060844.2 "transmembrane protein 106B [*Homo sapiens*]" Jul. 28, 2019 [online].

GenBank Accession No. NP_002078.1 "progranulin precursor [*Homo sapiens*]" Jan. 21, 2020 [online].

GenBank Accession No. NP_001317589.1 "non-lysosomal glucosylceramidase isoform 2 [*Homo sapiens*]" Aug. 7, 2019 [online].

GenBank Accession No. EAW81359.1 "galactosylceramidase, isoform CRA_a [*Homo sapiens*]" Mar. 23, 2015 [online].

GenBank Accession No. EAW81360.1 "galactosylceramidase, isoform CRA_b [*Homo sapiens*]" Mar. 23, 2015 [online].

GenBank Accession No. EAW81362.1 "galactosylceramidase, isoform CRA_c [*Homo sapiens*]" Mar. 23, 2015 [online].

GenBank Accession No. EAW68726.1 "sphingomyelin phosphodiesterase 1, acid lysosomal (acid sphingomyelinase), isoform CRA a [*Homo sapiens*]" Mar. 23, 2015 [online].

GenBank Accession No. EAW68727.1 "sphingomyelin phosphodiesterase 1, acid lysosomal (acid sphingomyelinase), isoform CRA_b [*Homo sapiens*]" Mar. 23, 2015 [online].

GenBank Accession No. EAW68728.1 "sphingomyelin phosphodiesterase 1, acid lysosomal (acid sphingomyelinase), isoform CRA_c [*Homo sapiens*]" Mar. 23, 2015 [online].

GenBank Accession No. EAW68729.1 "sphingomyelin phosphodiesterase 1, acid lysosomal (acid sphingomyelinase), isoform CRA_d [*Homo sapiens*]" Mar. 23, 2015 [online].

GenBank Accession No. AAC37547.1 "cathepsinB [*Homo sapiens*]" Apr. 7, 1994 [online].

GenBank Accession No. AAH95408.1 "Cathepsin B [*Homo sapiens*]" Jul. 17, 2006 [online].

(56) References Cited

OTHER PUBLICATIONS

GenBank Accession No. AAH10240.1 "Cathepsin B [*Homo sapiens*]" Jul. 15, 2006 [online].
GenBank Accession No. AAH02585.1 "RAB7, member RAS oncogene family-like 1 [*Homo sapiens*]" Jul. 15, 2006 [online].
GenBank Accession No. AAH25415.1 "GTP cyclohydrolase 1 [*Homo sapiens*]" Aug. 7, 2008 [online].
GenBank Accession No. AAH29804.1 "Interleukin 34 [*Homo sapiens*]" Jun. 9, 2008 [online].
GenBank Accession No. AAF69824.1 "triggering receptor expressed on myeloid cells 2 [*Homo sapiens*]" May 23, 2000 [online].
GenBank Accession No. NP_002087.1 "general transcription factor IIF, polypeptide 1, 74kDa [*Homo sapiens*]" Jun. 3, 2007 [online].
GenBank Accession No. NP_000152.1 "GTP cyclohydrolase 1 isoform 1 [*Homo sapiens*]" Dec. 30, 2019 [online].
Fumoto, et al. "Targeted Gene Delivery: Importance of Administration Routes." Chapter 1, Intech, 2013, pp. 3-31.
Hudry and Vandenberghe. "Therapeutic AAV Gene Transfer to the Nervous System: A Clinical Reality." Neuron 101, Mar. 6, 2019, 839-862.
Lazic and Barker. "Cell-based therapies for disorders of the CNS." Expert Opin. Ther. Patents (2005) 15(10): 1361-1376.
Ling, et al. "The Adeno-Associated Virus Genome Packaging Puzzle." J Mol Genet Med 2015, 9: 175, 4 pages.
Manno, et al. "Successful transduction of liver in hemophilia by AAV-Factor IX and limitations imposed by the host immune response." Nature Medicine, 2006, 12(3):342-349; 12(5):592.
Molnar and Nemeth. "Gene therapy in neurology: review of ongoing clinical trials." Clin. Invest. (2012) 2(6), 639-652.
Niederkofler, et al. "Characterization of relevant mouse models for new biomarkers." Poster #141, 2019, Society for Neuroscience Meeting, Chicago, IL, USA.
Salmon, et al. "Safety profile of recombinant adeno-associated viral vectors: focus on alipogene tiparvovec (Glybera)." Expert Rev. V Clin. Pharmacol., 2014,7(1), 53-65.
Shanks, et al. "Are animal models predictive for humans?" Philosophy, Ethics, and Humanities in Medicine, 2009, 4(2), 20 pages.
Wong, et al. "Lysosomal Trafficking Defects Link Parkinson's Disease With Gaucher's Disease." Movement Disorders, 2013, 31(11):1610-1618.
François, et al. "The Cellular TATA Binding Protein Is Required for Rep-Dependent Replication of a Minimal Adeno-Associated Virus Type 2 p5 Element", Journal of Virology, Sep. 2005; 79(17): 11082-94.
Genbank Accession No. AF043303.1, "Adeno-associated virus 2, complete genome", pp. 1-4; May 20, 2010.
GenBank Accession No. NM_000157.3, "(GBA1):c.1448T>C and Gaucher disease type III", pp. 1-2; Mar. 5, 2022.
Lonser, et al., "Convection-enhanced delivery to the central nervous system", J Neurosurg. Mar. 2015; 122(3): 697-706. Epub Nov. 14, 2014.
Siman, et al., "A Rapid Gene Delivery-Based Mouse Model for Early-Stage Alzheimer Disease-Type Tauopathy", J Neuropathol Exp Neurol. Nov. 2013; 72(11): 1062-71.
Xhima, et al., "Noninvasive Delivery of an A-Synuclein Gene Silencing Vector With Magnetic Resonance-Guided Focused Ultrasound", Movement Disorders. Oct. 2018; 33(10): 1567-79. Epub Sep. 28, 2018.
Xu, et al., "Tau Silencing by siRNA in the P301S Mouse model of Tauopathy", Current Gene Therapy, Oct. 2014, 14(5): 343-51.
Giasson, B. et al. "Neuronal α-Synucleinopathy with Severe Movement Disorder in Mice Expressing A53T Human α-Synuclein," Neuron, May 16, 2002, 34:521-533.
Mazzulli, J. et al. "Cytosolic Catechols Inhibit α-Synuclein Aggregation and Facilitate the Formation of Intracellular Soluble Oligomeric Intermediates," The Journal of Neuroscience, Sep. 27, 2006, 26(39):10068-10078.
Mazzulli, J. et al. "Gaucher Disease Glucocerebrosidase and α-Synuclein Form a Bidirectional Pathogenic Loop in Synucleinopathies," Cell, Jul. 8, 2011, 146:37-52.

* cited by examiner

PrevailVector_FP1_JetLong_GBA1_bGH_JetLong_SCARB2_SV40L_4464nt
11,420 bp

GENE THERAPIES FOR LYSOSOMAL DISORDERS

RELATED APPLICATIONS

This Application is a 35 U.S.C. § 371 national phase application of International Application No. PCT/US2018/054255, filed Oct. 3, 2018, which claims priority under 35 U.S.C. § 119(e) to the filing date of U.S. Provisional Application Ser. No. 62/567,296, filed Oct. 3, 2017, entitled "GENE THERAPIES FOR LYSOSOMAL DISORDERS". The disclosure of each of these applications is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVL-002-02US_SeqList.txt, date recorded: Apr. 2, 2020, file size ~211,004 bytes).

BACKGROUND

Gaucher disease is a rare inborn error of glycosphingolipid metabolism due to deficiency of lysosomal acid β-glucocerebrosidase (Gcase, "GBA"). Patients suffer from non-CNS symptoms and findings including hepatosplenomegly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease.

Several therapeutics exist that address the peripheral disease and the principal clinical manifestations in hematopoietic bone marrow and viscera, including enzyme replacement therapies, chaperone-like small molecule drugs that bind to defective Gcase and improve stability, and substrate reduction therapy that block the production of substrates that accumulate in Gaucher disease, leading to symptoms and pathology. However, other aspects of Gaucher disease and appear refractory to treatment.

SUMMARY

In addition to Gaucher disease patients (who possess mutations in both chromosomal alleles of GBA1 gene), patients with mutations in only one allele of GBA1 are at highly increased risk of Parkinson's disease (PD). The severity of PD symptoms—which include gait difficulty, a tremor at rest, rigidity, and often depression, sleep difficulties, and cognitive decline—correlate with the degree of enzyme activity reduction. Thus, Gaucher disease patients have the most severe course, whereas patient with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders.

Deficits in enzymes such as Gcase (e.g., the gene product of GBA1 gene), as well as common variants in many genes implicated in lysosome function or trafficking of macromolecules to the lysosome (e.g., Lysosomal Membrane Protein 1 (LIMP), also referred to as SCARB2), have been associated with increased PD risk. The disclosure is based, in part, on expression constructs (e.g., vectors) encoding Gcase (or a portion thereof), prosaposin (or a portion thereof), LIMP2 (or a portion thereof), or a combination of Gcase (or a portion thereof) and one or more additional gene products from PD-associated genes (e.g., LIMP2, Prosaposin, and/or α-Synuclein (α-Syn)). In some embodiments, combinations of gene products described herein act together (e.g., synergistically) to reduce one or more signs and symptoms of PD when expressed in a subject.

Accordingly, in some aspects, the disclosure provides an isolated nucleic acid comprising an expression construct encoding a Gcase (e.g., the gene product of GBA1 gene). In some embodiments, the isolated nucleic acid comprises a Gcase-encoding sequence that has been codon optimized (e.g., codon optimized for expression in mammalian cells, for example human cells). In some embodiments, the nucleic acid sequence encoding the Gcase encodes a protein comprising an amino acid sequence as set forth in SEQ ID NO: 14 (e.g., as set forth in NCBI Reference Sequence NP_000148.2). In some embodiments, the isolated nucleic acid comprises the sequence set forth in SEQ ID NO: 15. In some embodiments the expression construct comprises adeno-associated virus (AAV) inverted terminal repeats (ITRs), for example AAV ITRs flanking the nucleic acid sequence encoding the Gcase.

In some aspects, the disclosure provides an isolated nucleic acid comprising an expression construct encoding Prosaposin (e.g., the gene product of PSAP gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the prosaposin encodes a protein comprising an amino acid sequence as set forth in SEQ ID NO: 16 (e.g., as set forth in NCBI Reference Sequence NP_002769.1). In some embodiments, the isolated nucleic acid comprises the sequence set forth in SEQ ID NO: 17. In some embodiments the expression construct comprises adeno-associated virus (AAV) inverted terminal repeats (ITRs), for example AAV ITRs flanking the nucleic acid sequence encoding the prosaposin.

In some aspects, the disclosure provides an isolated nucleic acid comprising an expression construct encoding LIMP2/SCARB2 (e.g., the gene product of SCARB2 gene). In some embodiments, the isolated nucleic acid comprises a SCARB2-encoding sequence that has been codon optimized (e.g., codon optimized for expression in mammalian cells, for example human cells). In some embodiments, the nucleic acid sequence encoding the LIMP2/SCARB2 encodes a protein comprising an amino acid sequence as set forth in SEQ ID NO: 18 (e.g., as set forth in NCBI Reference Sequence NP_005497.1). In some embodiments, the isolated nucleic acid comprises the sequence set forth in SEQ ID NO: 29. In some embodiments the expression construct comprises adeno-associated virus (AAV) inverted terminal repeats (ITRs), for example AAV ITRs flanking the nucleic acid sequence encoding the SCARB2.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product or a second gene product is LIMP2 or a portion thereof, or Prosaposin or a portion thereof. In some embodiments, the first gene product is a Gcase protein, and the second gene product is LIMP2 or a portion thereof, or Prosaposin or a portion thereof.

In some embodiments, an expression construct further encodes an interfering nucleic acid (e.g., shRNA, miRNA, dsRNA, etc.). In some embodiments, an interfering nucleic acid inhibits expression of α-Synuclein (α-Synuclein). In some embodiments, an interfering nucleic acid that targets α-Synuclein comprises a sequence set forth in any one of SEQ ID NOs: 20-25. In some embodiments, an interfering nucleic acid that targets α-Synuclein binds to (e.g., hybridizes with) a sequence set forth in any one of SEQ ID NO: 20-25.

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter (or an RNA pol III promoter (e.g., U6, etc.).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments, ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 29). In some embodiments, the ITR having the modified D region is the 5' ITR of the rAAV vector. In some embodiments, a modified "D" region comprises an "S" sequence, for example as set forth in SEQ ID NO: 26. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 26 or 27.

In some embodiments, an isolated nucleic acid (e.g., an rAAV vector) comprises a TRY region. In some embodiments, a TRY region comprises the sequence set forth in SEQ ID NO: 28.

In some embodiments, an isolated nucleic acid described by the disclosure comprises or consists of the sequence set forth in any one of SEQ ID NOs: 1 to 13, 15, 17, and 19. In some embodiments, an isolated nucleic acid described by the disclosure encodes a peptide comprising or consisting of the sequence set forth in any one of SEQ ID NOs: 14, 16, and 18.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector. In some embodiments, an rAAV vector is single-stranded (e.g., single-stranded DNA).

In some aspects, the disclosure provides a host cell comprising an isolated nucleic acid as described by the disclosure or a vector as described by the disclosure.

In some aspects, the disclosure provides a recombinant adeno-associated virus (rAAV) comprising a capsid protein and an isolated nucleic acid or a vector as described by the disclosure.

In some embodiments, a capsid protein is capable of crossing the blood-brain barrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, administration comprises direct injection to the CNS of a subject. In some embodiments, direct injection is intracerebral injection, intraparenchymal injection, intrathecal injection, intra-cisterna magna injection, or any combination thereof. In some embodiments, direct injection to the CNS of a subject comprises convection enhanced delivery (CED).

In some embodiments, administration comprises peripheral injection. In some embodiments, peripheral injection is intravenous injection.

DETAILED DESCRIPTION

Figure 1:
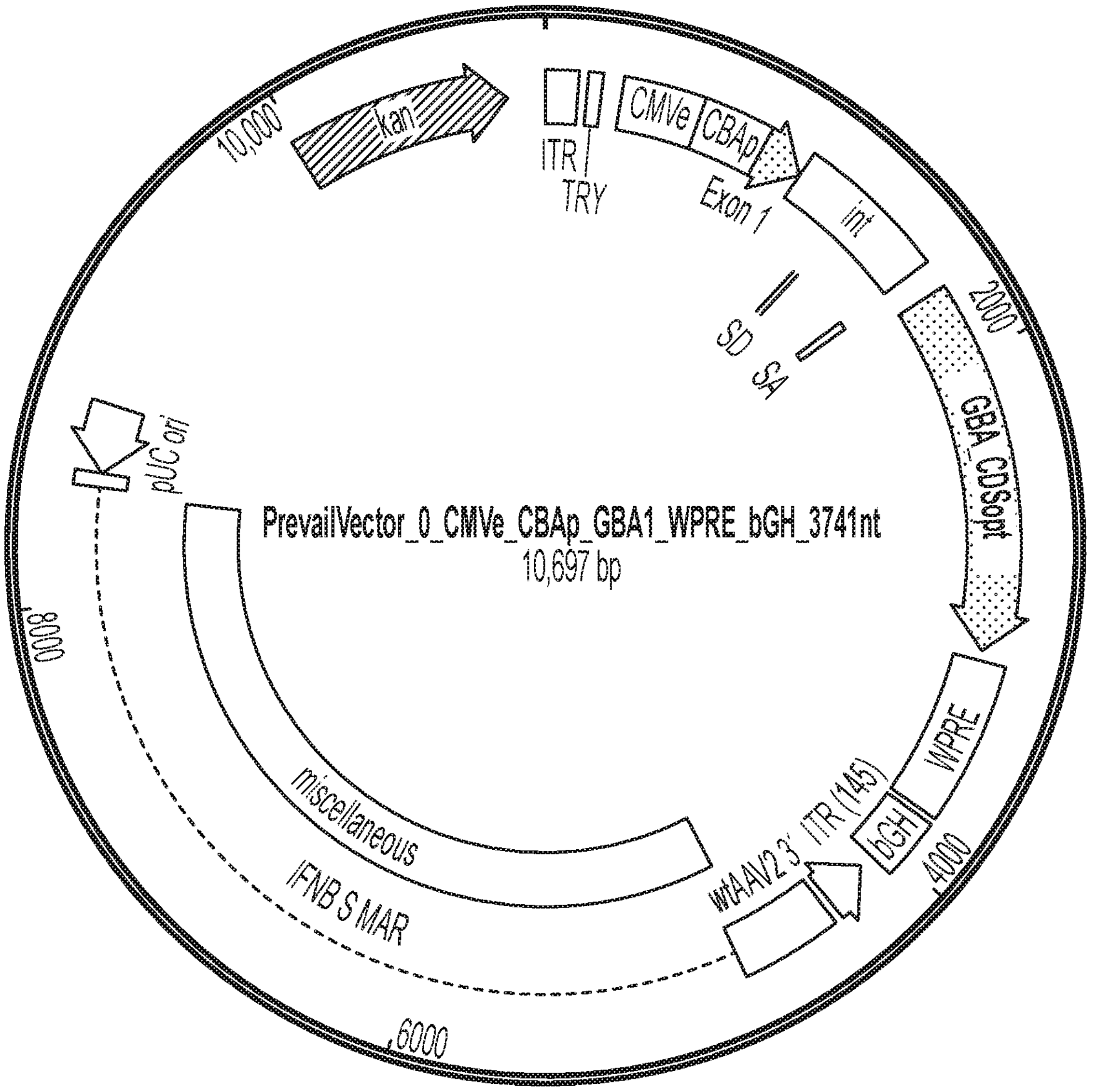
FIG. 1 is a schematic depicting one embodiment of a plasmid comprising an rAAV vector that includes an expression construct encoding Gcase (e.g., GBA1 or a portion thereof).
Figure 2:
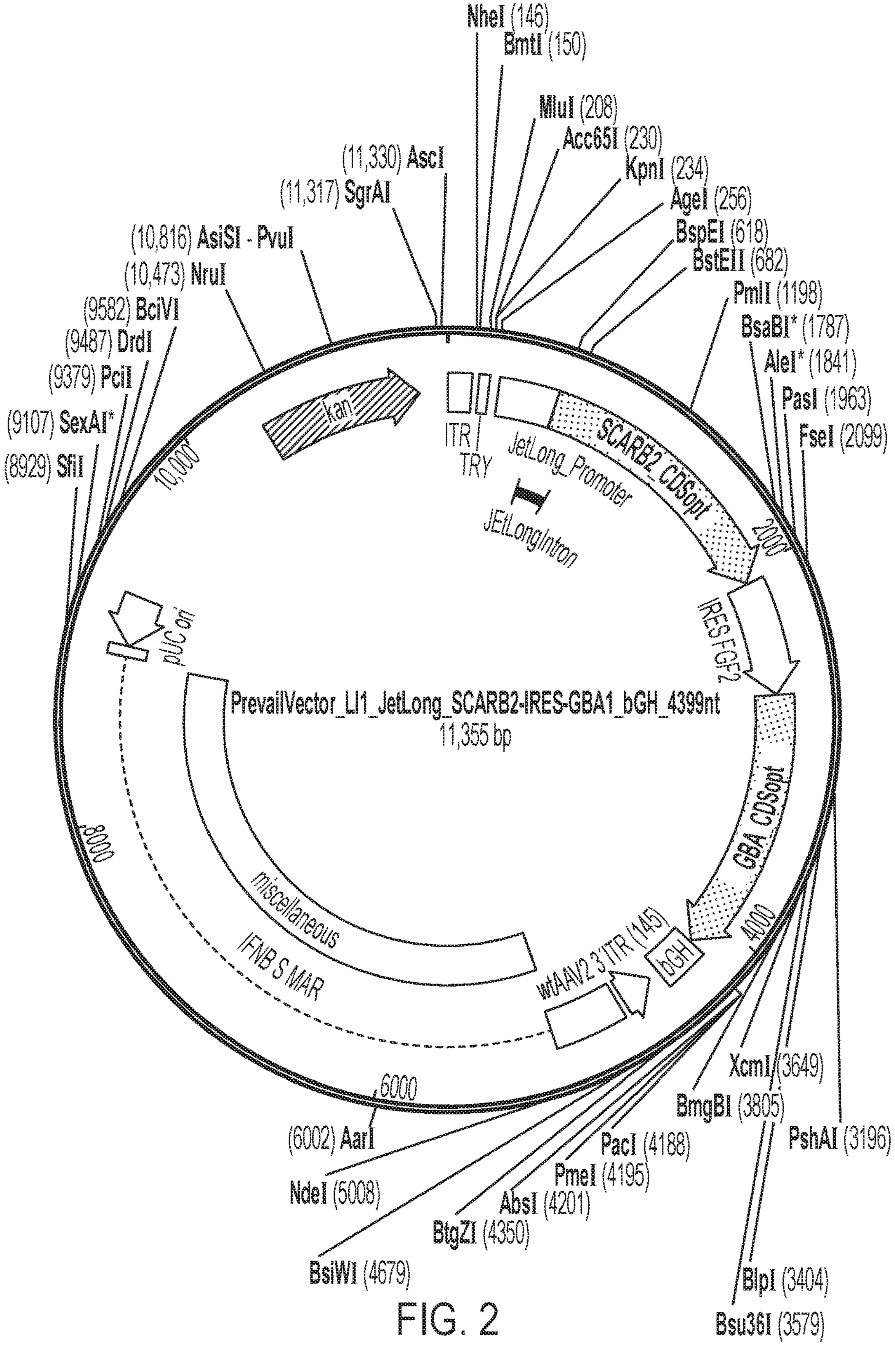
FIG. 2 is a schematic depicting one embodiment of a plasmid comprising an rAAV vector that includes an expression construct encoding Gcase (e.g., GBA1 or a portion thereof) and LIMP2 (SCARB2) or a portion thereof. The coding sequences of Gcase and LIMP2 are separated by an internal ribosomal entry site (IRES).
Figure 3:
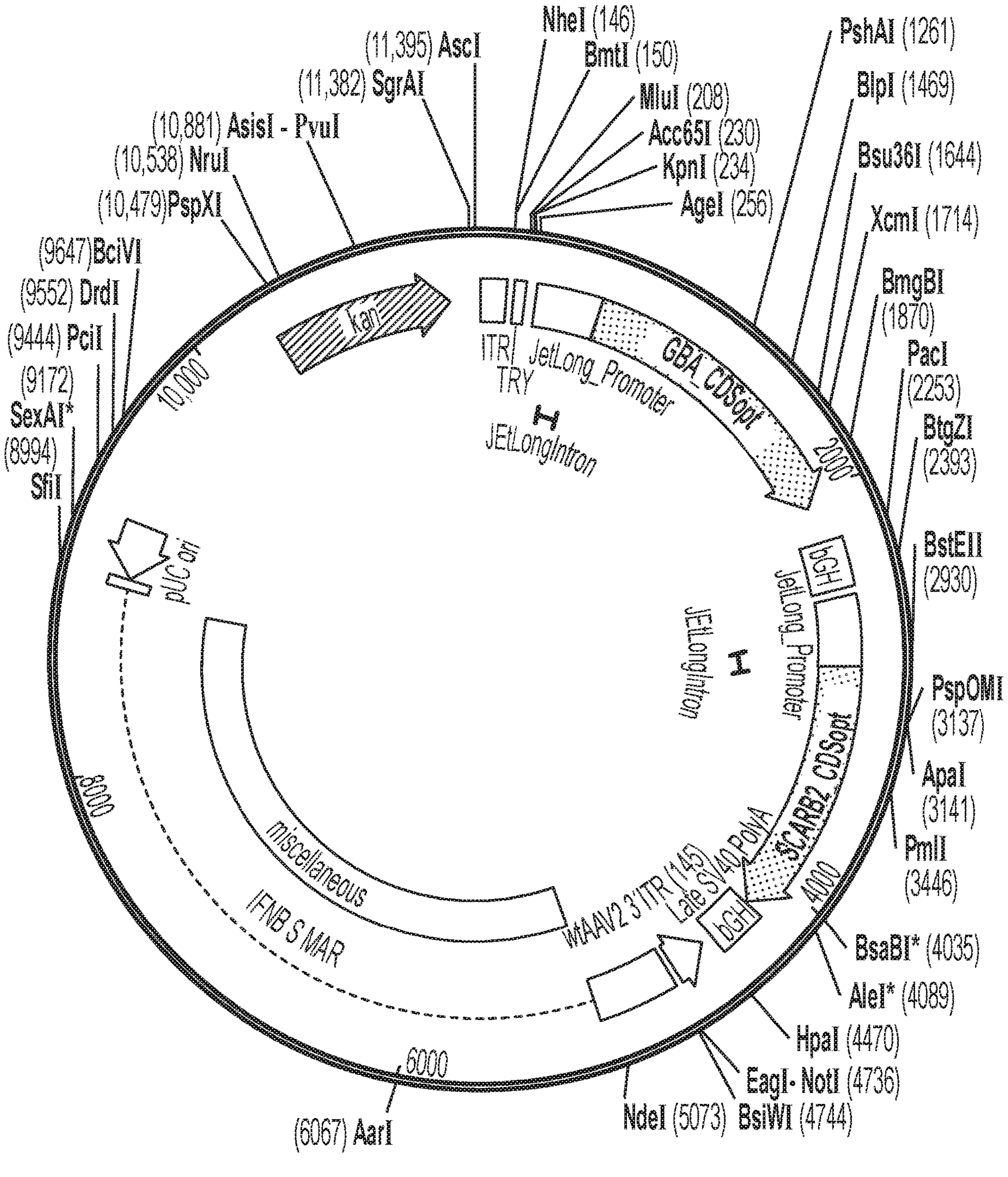
FIG. 3 is a schematic depicting one embodiment of a plasmid comprising an rAAV vector that includes an expression construct encoding Gcase (e.g., GBA1 or a portion thereof) and LIMP2 (SCARB2) or a portion thereof. Expression of the coding sequences of Gcase and LIMP2 are each driven by a separate promoter.
Figure 4:
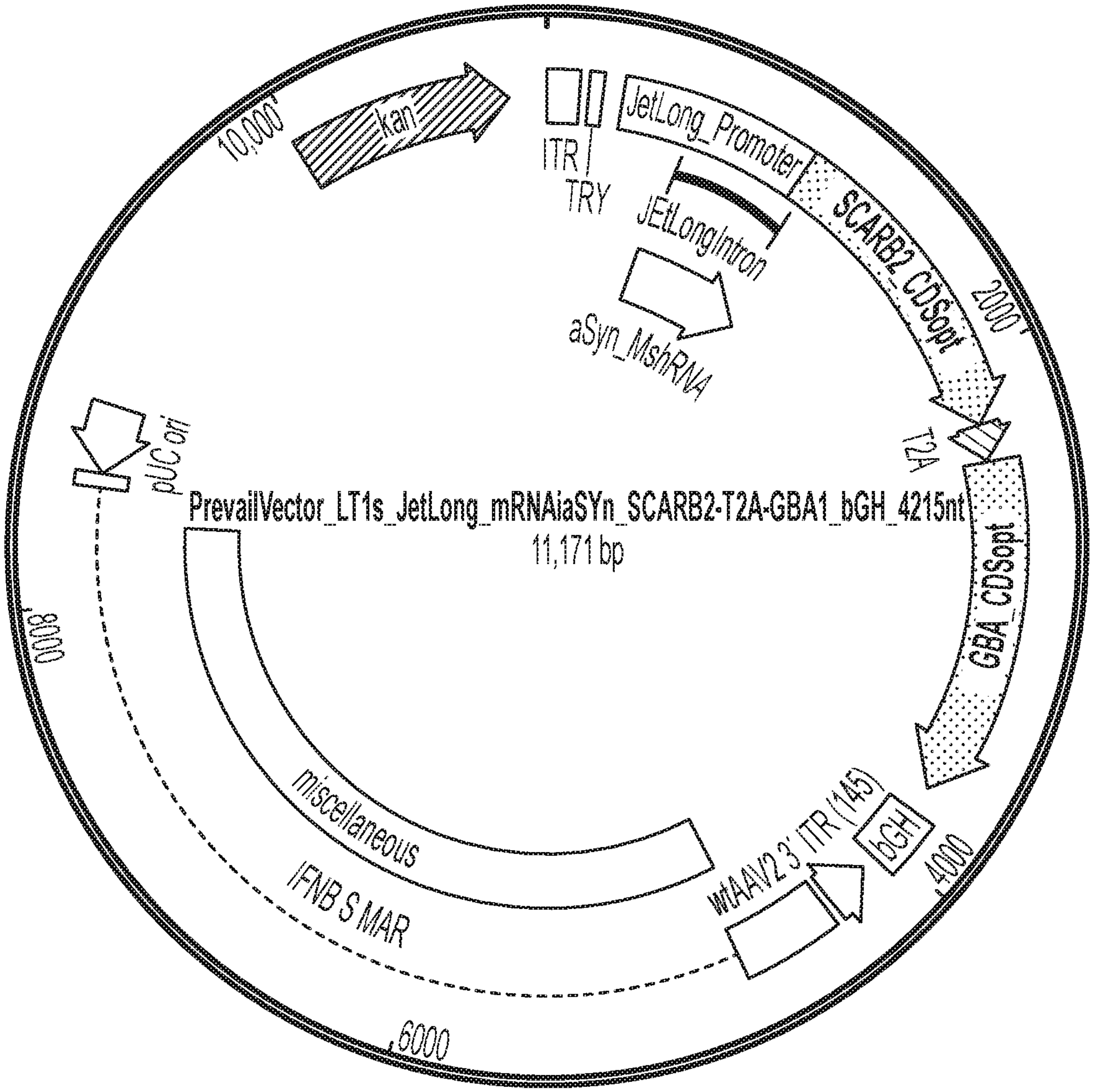
FIG. 4 is a schematic depicting one embodiment of a plasmid comprising an rAAV vector that includes an expression construct encoding Gcase (e.g., GBA1 or a portion thereof), LIMP2 (SCARB2) or a portion thereof, and an interfering RNA for α-Syn.
Figure 5:
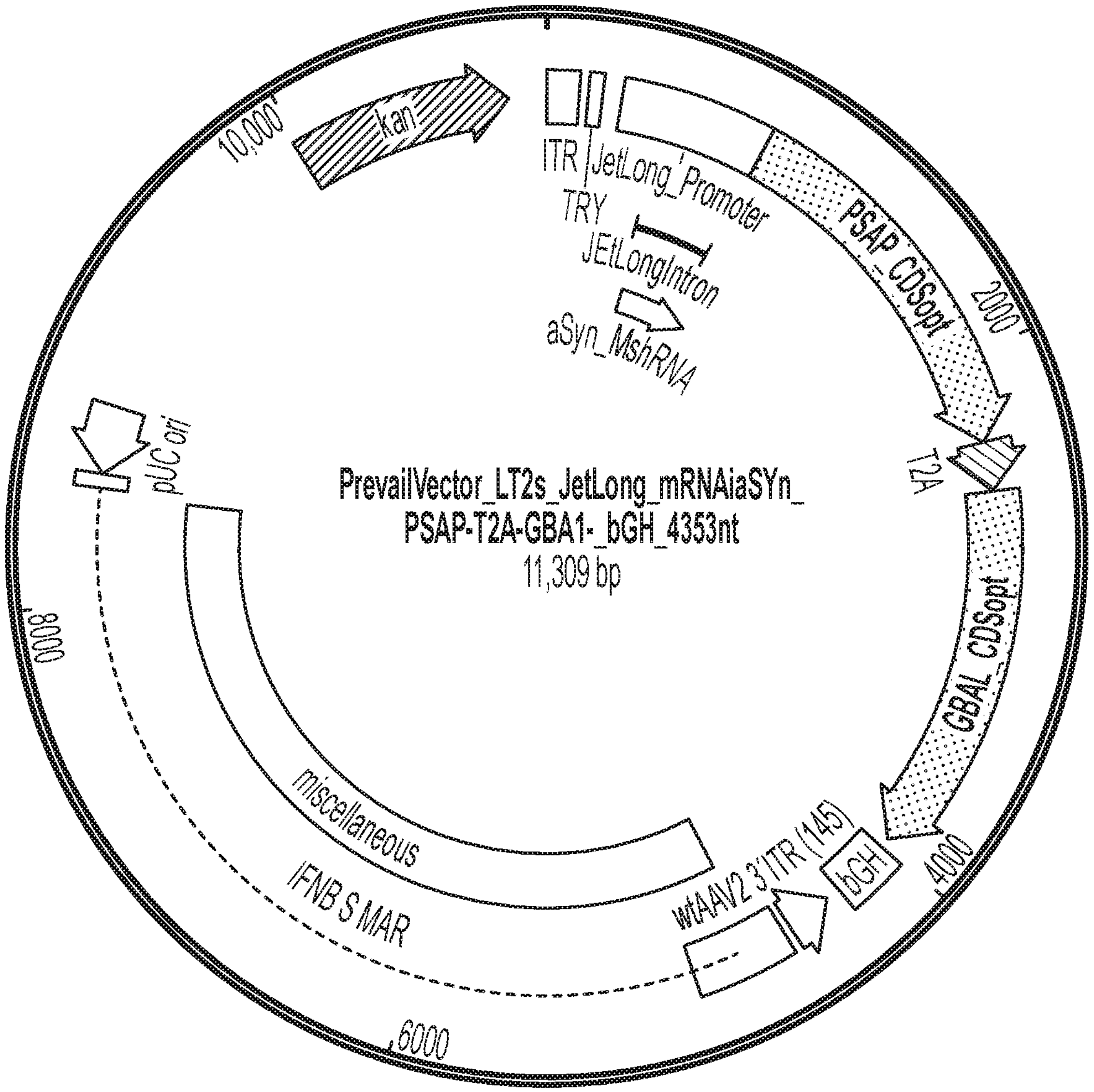
FIG. 5 is a schematic depicting one embodiment of a plasmid comprising an rAAV vector that includes an expression construct encoding Gcase (e.g., GBA1 or a portion thereof), Prosaposin (e.g., PSAP or a portion thereof), and an interfering RNA for α-Syn.
Figure 6:
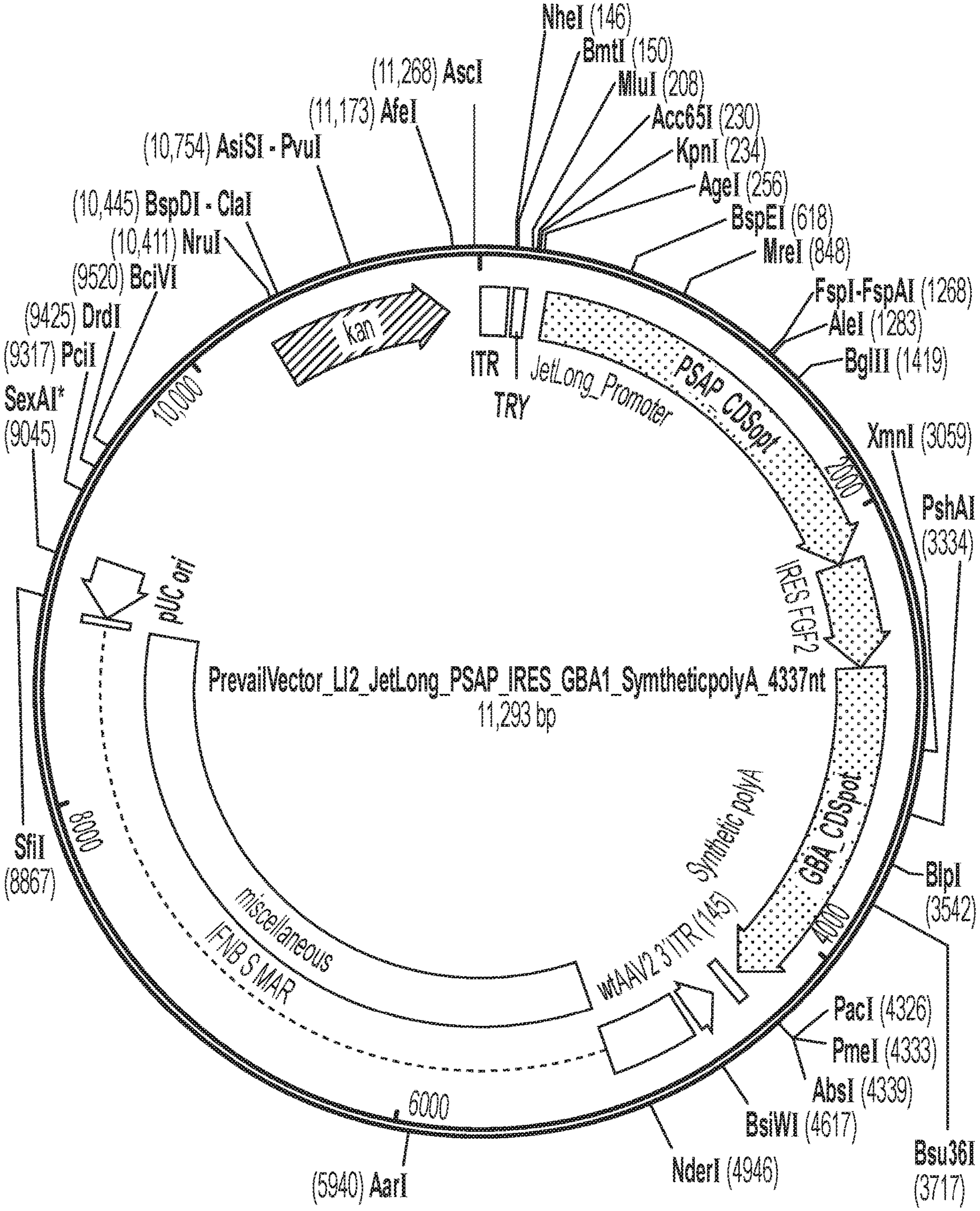
FIG. 6 is a schematic depicting one embodiment of a plasmid comprising an rAAV vector that includes an expression construct encoding Gcase (e.g., GBA1 or a portion thereof) and Prosaposin (e.g., PSAP or a portion thereof). The coding sequences of Gcase and Prosaposin are separated by an internal ribosomal entry site (IRES).

The disclosure is based, in part, on compositions and methods for expression of combinations of PD-associated gene products in a subject. A gene product can be a protein, a fragment (e.g., portion) of a protein, an interfering nucleic acid that inhibits a PD-associated gene, etc. In some embodiments, a gene product is a protein or a protein fragment encoded by a PD-associated gene. In some embodiments, a gene product is an interfering nucleic acid (e.g., shRNA, siRNA, miRNA, amiRNA, etc.) that inhibits a PD-associated gene.

A PD-associated gene refers to a gene encoding a gene product that is genetically, biochemically or functionally associated with PD. For example, individuals having mutations in the GBA1 gene (which encodes the protein Gcase), have been observed to be have an increased risk of developing PD compared to individuals that do not have a mutation in GBA1. In another example, PD is associated with accumulation of protein aggregates comprising α-Synuclein (α-Syn) protein; accordingly, SCNA (which encodes α-Syn) is a PD-associated gene. In some embodiments, an expression cassette described herein encodes a wild-type or non-mutant form of a PD-associated gene (or coding sequence thereof). Examples of PD-associated genes are listed in Table 1.

TABLE 1

Examples of PD-associated genes

| Name | Gene | Function | NCBI Accession No. |
|---|---|---|---|
| Lysosome membrane protein 2 | SCARB2/ LIMP2 | lysosomal receptor for glucosylceramidase (GBA targeting) | NP_005497.1 (Isoform 1), NP_001191184.1 (Isoform 2) |
| Prosaposin | PSAP | precursor for saposins A, B, C, and D, which localize to the lysosomal compartment and facilitate the catabolism of glycosphingolipids with short oligo-saccharide groups | AAH01503.1, AAH07612.1, AAH04275.1, AAA60303.1 |
| beta-Glucocerebrosidase | GBA1 | cleaves the beta-glucosidic linkage of glucocerebroside | NP_001005742.1 (Isoform 1), NP_001165282.1 (Isoform 2), NP_001165283.1 (Isoform 3) |

Isolated Nucleic Acids and Vectors

An isolated nucleic acid may be DNA or RNA. The disclosure provides, in some aspects, an isolated nucleic acid comprising an expression construct encoding a Gcase (e.g., the gene product of GBA1 gene) or a portion thereof. Gcase, also referred to as ß-glucocerebrosidase or GBA, refers to a lysosomal protein that cleaves the beta-glucosidic linkage of the chemical glucocerebroside, an intermediate in glycolipid metabolism. In humans, Gcase is encoded by the GBA1 gene, located on chromosome 1. In some embodiments, GBA1 encodes a peptide that is represented by NCBI Reference Sequence NP_000148.2 (SEQ ID NO: 14). In some embodiments, the isolated nucleic acid comprises a Gcase-encoding sequence that has been codon optimized (e.g., codon optimized for expression in mammalian cells, for example human cells), such as the sequence set forth in SEQ ID NO: 15.

In some aspects, the disclosure provides an isolated nucleic acid comprising an expression construct encoding Prosaposin (e.g., the gene product of PSAP gene). Prosaposin is a precursor glycoprotein for sphingolipid activator proteins (saposins) A, B, C, and D, which facilitate the catabolism of glycosphingolipids with short oligosaccharide groups. In humans, the PSAP gene is located on chromosome 10. In some embodiments, PSAP encodes a peptide that is represented by NCBI Reference Sequence NP_002769.1 (e.g., SEQ ID NO: 16). In some embodiments, the isolated nucleic acid comprises a prosaposin-encoding sequence that has been codon optimized (e.g., codon optimized for expression in mammalian cells, for example human cells), such as the sequence set forth in SEQ ID NO: 17.

Aspects of the disclosure relate to an isolated nucleic acid comprising an expression construct encoding LIMP2/SCARB2 (e.g., the gene product of SCARB2 gene). SCARB2 refers to a membrane protein that regulates lysosomal and endosomal transport within a cell. In humans, SCARB2 gene is located on chromosome 4. In some embodiments, the SCARB2 gene encodes a peptide that is represented by NCBI Reference Sequence NP_005497.1 (SEQ ID NO: 18). In some embodiments, the isolated nucleic acid comprises the sequence set forth in SEQ ID NO: 19. In some embodiments the isolated nucleic acid comprises a SCARB2-encoding sequence that has been codon optimized.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is a protein (or a fragment thereof) encoded by the SCARB2/LIMP2 gene and/or the PSAP gene. However, the skilled artisan recognizes that the order of expression of a first gene product (e.g., Gcase) and a second gene product (e.g., LIMP2) can generally be reversed (e.g., LIMP2 is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1.

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) *BMC Cell Biol.* 9:2; doi: 10.1186/1471-2121-9-2), a CD68 promoter, or a JeT promoter (for example as described by Tornøe et al. (2002) *Gene* 297(1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34(Database issue): D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an expression construct, for example in an intron upstream of the sequence encoding a first gene product. An inhibitory nucleic acid can be a double stranded RNA (dsRNA), siRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA).

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, the vector is a recombinant AAV (rAAV) vector. In some embodiments, an rAAV vector is single-stranded (e.g., single-stranded DNA). In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) *Gene Ther.* 10(26):2112-8.

Figure 19:
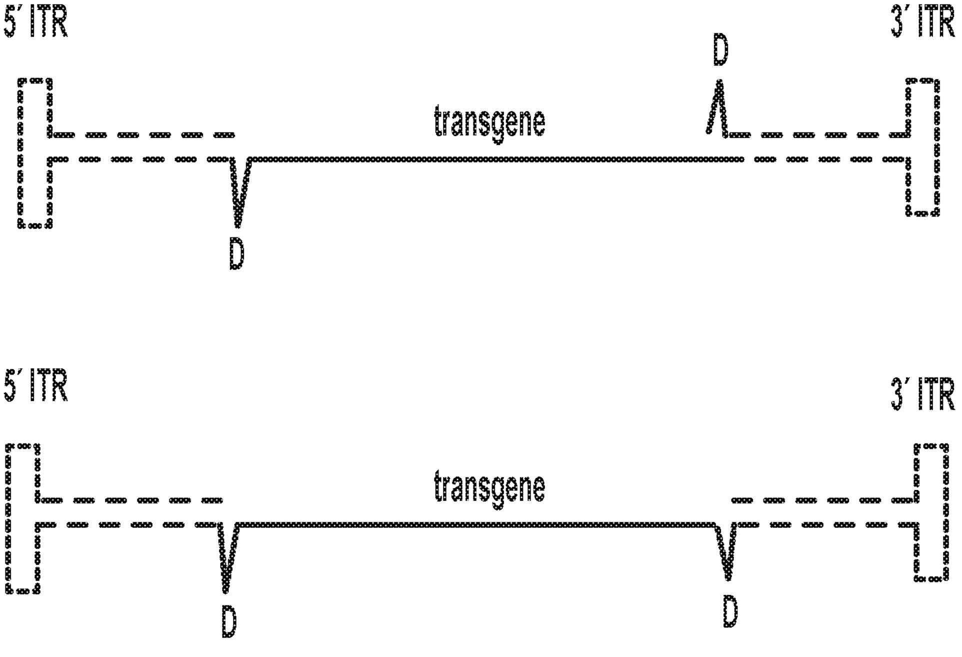
FIG. 19 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 29). The structure of wild-type AAV2 ITR is shown in FIG. 19. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region. (FIG. 19). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 27. The "D" region has been observed to play an important role in encapsidation of rAAV vectors by capsid proteins, for example as disclosed by Ling et al. (2015) *J Mol Genet Med* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs. In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 27). A modified "D" sequence may have at least 1, 2, 3, 4, 5, 6, 7, 8, 9, 10, or more than 10 nucleotide substitutions relative to a wild-type "D" sequence (e.g., SEQ ID NO: 27). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 27). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type "D" sequence (e.g., SEQ ID NO: 27). In some embodiments, a modified "D" sequence comprises the sequence set forth in SEQ ID NO: 26, also referred to as an "S" sequence as described in Wang et al. (1995) *J Mol Biol* 250(5):573-80.

An isolated nucleic acid or rAAV vector as described by the disclosure may further comprise a "TRY" sequence, for example as set forth in SEQ ID NO: 28 or as described in Francois, et al. The Cellular TATA Binding Protein Is Required for Rep-Dependent Replication of a Minimal Adeno-Associated Virus Type 2 p5 Element. J Virol. 2005. In some embodiments, a TRY sequence is positioned between an ITR (e.g., a 5' ITR) and an expression construct (e.g., a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh. 10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20 25, 50, 100, etc.) amino acid substitutions (e.g., mutations) relative to the wild-type AAV capsid protein from which it is derived.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh. 10 serotype. Production of rAAVs is described, for example, by Samulski et al. (1989) *J Virol.* 63(9):3822-8 and Wright (2009) *Hum Gene Ther.* 20(7): 698-706.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) *Hum Gene Ther* 13(16):1935-43, Smith et al. (2009) *Mol Ther* 17(11): 1888-1896, U.S. Pat. Nos. 8,945,918, 9,879,282, and International PCT Publication WO 2017/184879. However, an rAAV can be produced using any suitable method (e.g., using recombinant rep and cap genes).

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

Methods

The disclosure is based, in part, on compositions for expression of combinations of PD-associated gene products in a subject that act together (e.g., synergistically) to treat Parkinson's disease. As used herein "treat" or "treating" refers to (a) preventing or delaying onset of Parkinson's disease; (b) reducing severity of Parkinson's disease; (c) reducing or preventing development of symptoms characteristic of Parkinson's disease; (d) and/or preventing worsening of symptoms characteristic of Parkinson's disease. Symptoms of Parkinson's disease include, for example, motor dysfunction (e.g., shaking, rigidity, slowness of movement, difficulty with walking), cognitive dysfunction (e.g., dementia, depression, anxiety), emotional and behavioral dysfunction.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) *Expert Rev Neurother.* 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1: rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and LIMP2 and/or Prosaposin, by fusion of the protein sequences; or using a 2A peptide linker, such as T2A or P2A, which leads 2 peptide fragments with added amino acids due to prevention of the creation of a peptide bond; or using an IRES element; or by expression with 2 separate expression cassettes. The presence of a short intronic sequence that is efficiently spliced, upstream of the expressed gene, can improve expression levels. shRNAs and other regulatory RNAs can potentially be included within these sequences. Examples of plasmids comprising rAAV vectors described by the disclosure are shown in FIGS. 1-6 and in Table 2 below.

TABLE 2

| Name | Promoter 1 | shRNA | CDS1 | PolyA1 | Bicistronic element | Promoter 2 | CDS2 | PolyA2 | Length between ITRs |
|---|---|---|---|---|---|---|---|---|---|
| CMVe_CBAp_GBA1_WPRE_bGH | CBA | | GBA1 | WPRE-bGH | | | | | 3741 |
| LT1s_JetLong_mRNAiaSYn_SCARB2-T2A-GBA1_bGH | JetLong | aSyn | SCARB2 | bGH | T2A | | GBA1 | | 4215 |
| LI1_JetLong_SCARB2-IRES-GBA1_bGH | JetLong | | SCARB2 | bGH | IRES | | GBA1 | | 4399 |
| FP1_JetLong_GBA1_bGH_JetLong_SCARB2_SV40L | JetLong | | GBA1 | bGH | | JetLong | SCARB2 | SV40L | 4464 |
| PrevailVector_LT2s_JetLong_mRNAiaSYn_PSAP-T2A-GBA1_bGH_4353nt | JetLong | aSyn | PSAP | bGH | T2A | — | GBA1 | — | 4353 |
| PrevailVector_LI2_JetLong_PSAP_IRES_GBA1_SymtheticpolyA_4337nt | JetLong | — | PSAP | Synthetic pA | IRES | — | GBA1 | — | 4337 |

Example 2: Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (GluCer and GluSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-αSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can is also quantified using protein ELISA measures, or by standard Gcase activity assays.

Example 3: In Vivo Assays Using Mutant Mice

This example describes in vivo assays of AAV vectors using mutant mice. In vivo studies of AAV vectors as above in mutant mice are performed using assays described, for example, by Liou et al. (2006) *J. Biol. Chem.* 281(7): 4242-4253, Sun et al. (2005) *J. Lipid Res.* 46:2102-2113, and Farfel-Becker et al. (2011) *Dis. Model Mech.* 4(6):746-752.

The intrathecal or intraventricular delivery of vehicle control and AAV vectors (e.g., at a dose of $2\times10^{11}$ vg/mouse) are performed using concentrated AAV stocks, for example at an injection volume between 5-10 μL. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4: Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J Pathol.* 239(4):496-509.

Intrathecal or intraventricular delivery of vehicle control and AAV vectors (e.g., at a dose of $2\times10^{11}$ vg/mouse) are performed using concentrated AAV stocks, for example with injection volume between 5-10 μL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5: Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6: Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7: Treatment of CNS Forms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8: Gene Therapy of Parkinson's Disease in Subjects Having Mutations in GBA1

This example describes administration of a recombinant adeno-associated virus (rAAV) encoding GBA1 to a subject having Parkinson's disease characterized by a mutation in GBA1 gene.

The rAAV vector insert contains the CBA promoter element (CBA), consisting of four parts: the CMV enhancer (CMVe), CBA promoter (CBAp), Exon 1, and intron (int) to constitutively express the codon optimized coding sequence (CDS) of human GBA1 (maroon). The 3' region also contains a Woodchuck hepatitis virus Posttranscriptional Regulatory Element (WPRE) followed by a bovine Growth Hormone polyA signal (bGH polyA) tail. The flanking ITRs allow for the correct packaging of the intervening sequences. Two variants of the 5' ITR sequence (FIG. 7, inset box, bottom sequence) were evaluated; these variants have several nucleotide differences within the 20-nucleotide "D" region of the ITR, which is believed to impact the efficiency of packaging and expression. The rAAV product contains the "D" domain nucleotide sequence shown in FIG. 7 (inset box, top sequence). A variant vector, harbors a mutant "D" domain (termed an "S" domain herein, with the nucleotide changes shown by shading), performed similarly in preclinical studies. The backbone contains the gene to confer resistance to kanamycin as well as a stuffer sequence to prevent reverse packaging. A schematic depicting the rAAV vector is shown in FIG. 8 The rAAV vector is packaged into an rAAV using AAV9 serotype capsid proteins.

GBA1-rAAV is administered to a subject as a single dose via a fluoroscopy guided sub-occipital injection into the cisterna magna (intracisternal magna; ICM). One embodiment of a dosing regimen study is as follows:

A single dose of rAAV is administered to patients (N=12) at one of two dose levels (3e13 vg (low dose); 1e14 vg (high dose), etc.) which are determined based on the results of nonclinical pharmacology and toxicology studies.

Initial studies were conducted in a chemical mouse model involving daily delivery of conduritol-b-epoxide (CBE), an inhibitor of GCase to assess the efficacy and safety of the rAAV vector and a variant rAAV S-variant construct (as described further below). Additionally, initial studies were performed in a genetic mouse model, which carries a homozygous GBA1 mutation and is partially deficient in saposins (4L/PS-NA). Additional dose-ranging studies in mice and nonhuman primates (NHPs) are conducted to further evaluate vector safety and efficacy.

Figure 7:
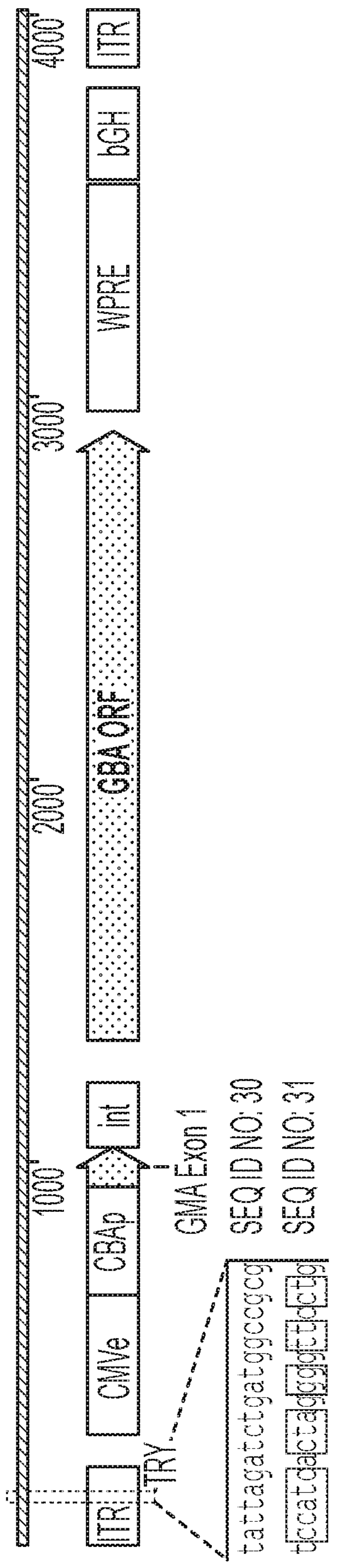
FIG. 7 is a schematic depicting one embodiment of an rAAV vector that includes an expression construct encoding a Gcase (e.g., GBA1 or a portion thereof). In this embodiment, the vector comprises a CBA promoter element (CBA), consisting of four parts: the CMV enhancer (CMVe), CBA promoter (CBAp), Exon 1, and intron (int) to constitutively express the codon optimized coding sequence of human GBA1. The 3' region also contains a WPRE regulatory element followed by a bGH polyA tail. Three transcriptional regulatory activation sites are included at the 5' end of the promoter region: TATA, RBS, and YY1. The flanking ITRs allow for the correct packaging of the intervening sequences. Two variants of the 5' ITR sequence (inset box) were evaluated; these have several nucleotide differences within the 20-nucleotide "D" region of wild-type AAV2 ITR. In some embodiments, an rAAV vector contains the "D" domain nucleotide sequence shown on the top line. In some embodiments, an rAAV vector comprises a mutant "D" domain (e.g., an "S" domain, with the nucleotide changes shown on the bottom line).
Figure 8:
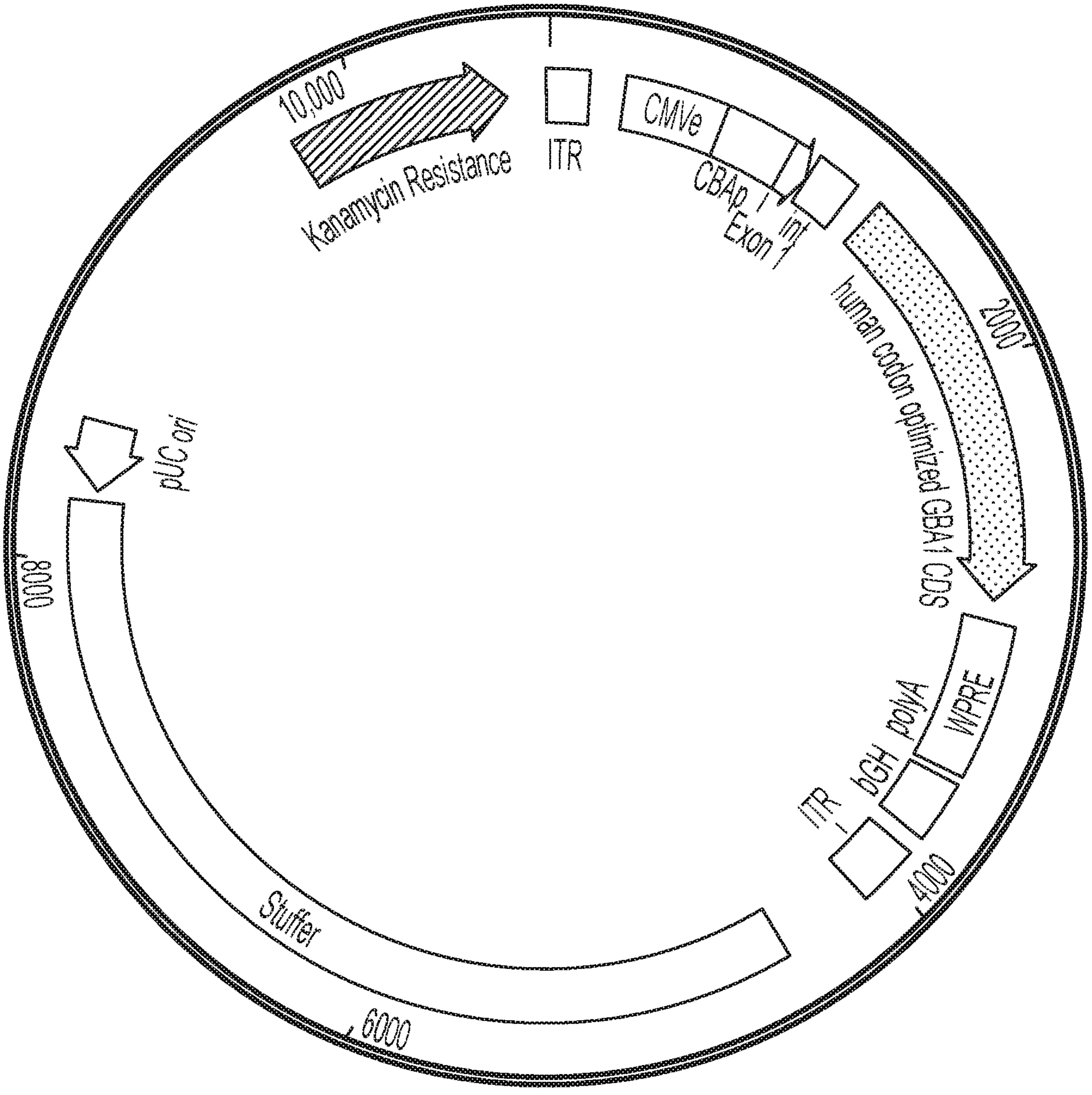
FIG. 8 is a schematic depicting one embodiment of a plasmid encoding the rAAV vector described in FIG. 7.

Two slightly different versions of the 5' inverted terminal repeat (ITR) in the AAV backbone were tested to assess manufacturability and transgene expression (FIG. 7). The 20 bp "D" domain within the 145 bp 5' ITR is thought to be necessary for optimal viral vector production, but mutations within the "D" domain have also been reported to increase transgene expression in some cases. Thus, in addition to the viral vector, which harbors an intact "D" domain, a second vector form with a mutant D domain (termed an "S" domain herein) was also evaluated. Both rAAV and variant rAAV express the same transgene. While both vectors produced virus that was efficacious in vivo as detailed below, the rAAV which contains a wild-type "D" domain, was selected for further development.

Figure 9:
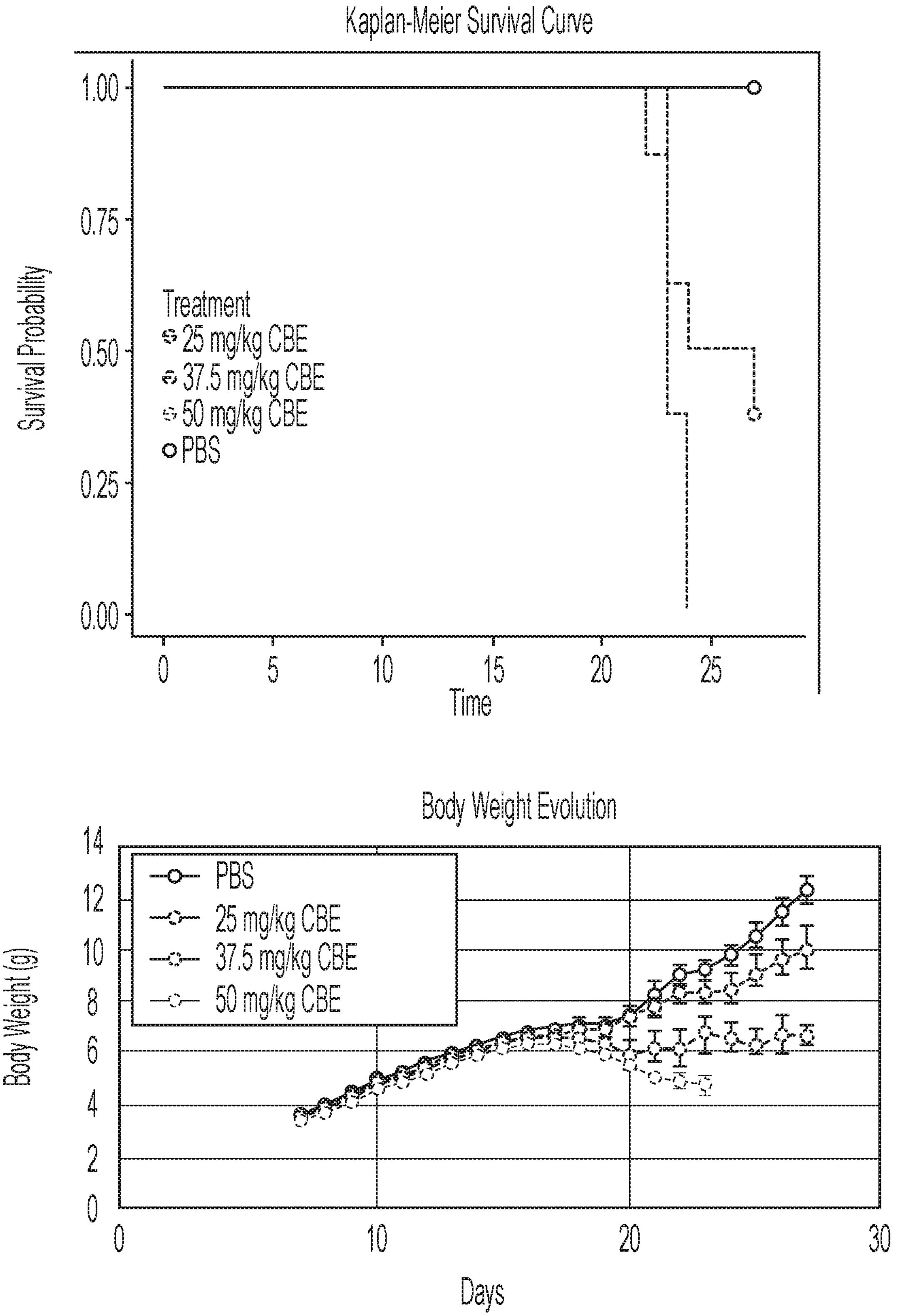
FIG. 9 shows representative data for delivery of an rAAV comprising a transgene encoding a Gcase (e.g., GBA1 or a portion thereof) in a CBE mouse model of Parkinson's disease. Daily IP delivery of PBS vehicle, 25 mg/kg CBE, 37.5 mg/kg CBE, or 50 mg/kg CBE (left to right) initiated at P8. Survival (top left) was checked two times a day and weight (top right) was checked daily. All groups started with n=8. Behavior was assessed by total distance traveled in Open Field (bottom left) at P23 and latency to fall on Rotarod (bottom middle) at P24. Levels of the GCase substrates were analyzed in the cortex of mice in the PBS and 25 mg/kg CBE treatment groups both with (Day 3) and without (Day 1) CBE withdrawal. Aggregate GluSph and GalSph levels (bottom right) are shown as pmol per mg wet weight of the tissue. Means are presented. Error bars are SEM. *p<0.05; p<0.01; *p<0.001, nominal p-values for treatment groups by linear regression.
Figure 9:
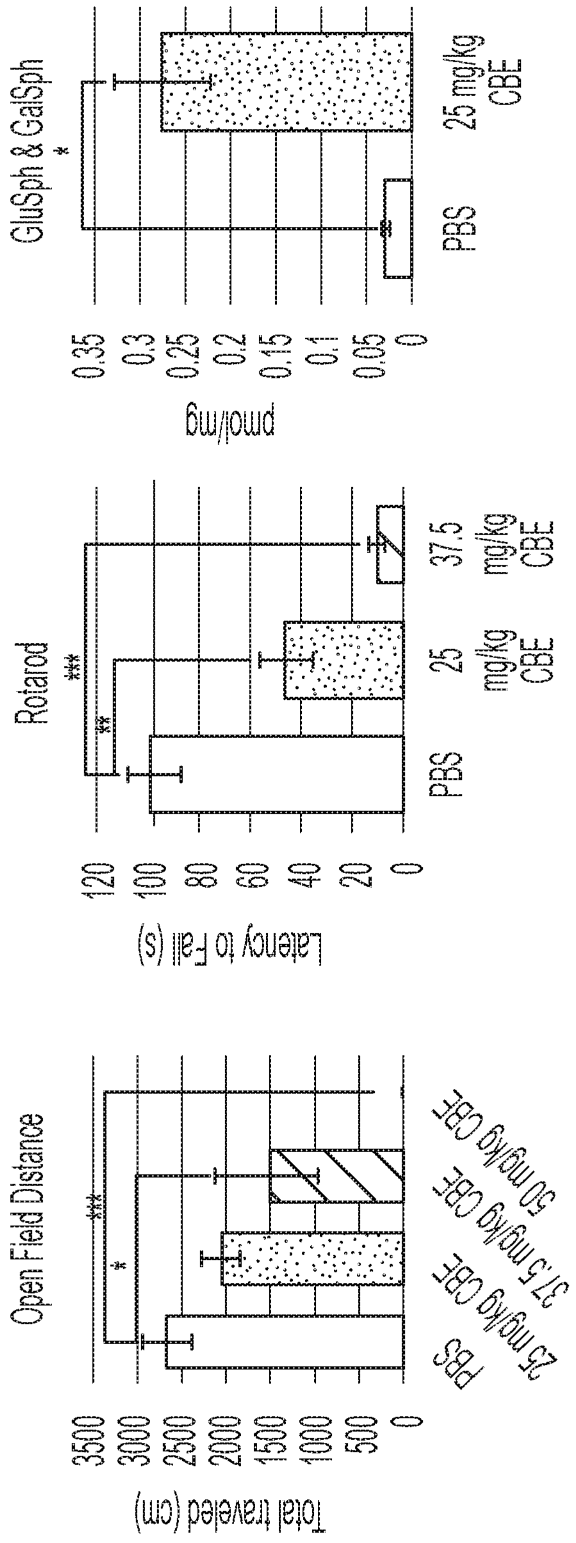

To establish the CBE model of GCase deficiency, juvenile mice were dosed with CBE, a specific inhibitor of GCase. Mice were given CBE by IP injection daily, starting at postnatal day 8 (P8). Three different CBE doses (25 mg/kg, 37.5 mg/kg, 50 mg/kg) and PBS were tested to establish a model that exhibits a behavioral phenotype (FIG. 9). Higher doses of CBE led to lethality in a dose-dependent manner. All mice treated with 50 mg/kg CBE died by P23, and 5 of the 8 mice treated with 37.5 mg/kg CBE died by P27. There was no lethality in mice treated with 25 mg/kg CBE. Whereas CBE-injected mice showed no general motor deficits in the open field assay (traveling the same distance and at the same velocity as mice given PBS), CBE-treated mice exhibited a motor coordination and balance deficit as measured by the rotarod assay.

Mice surviving to the end of the study were sacrificed on the day after their last CBE dose (P27, "Day 1") or after three days of CBE withdrawal (P29, "Day 3"). Lipid analysis was performed on the cortex of mice given 25 mg/kg CBE to evaluate the accumulation of GCase substrates in both the Day 1 and Day 3 cohorts. GluSph and GalSph levels (measured in aggregate in this example) were significantly accumulated in the CBE-treated mice compared to PBS-treated controls, consistent with GCase insufficiency.

Figure 10:
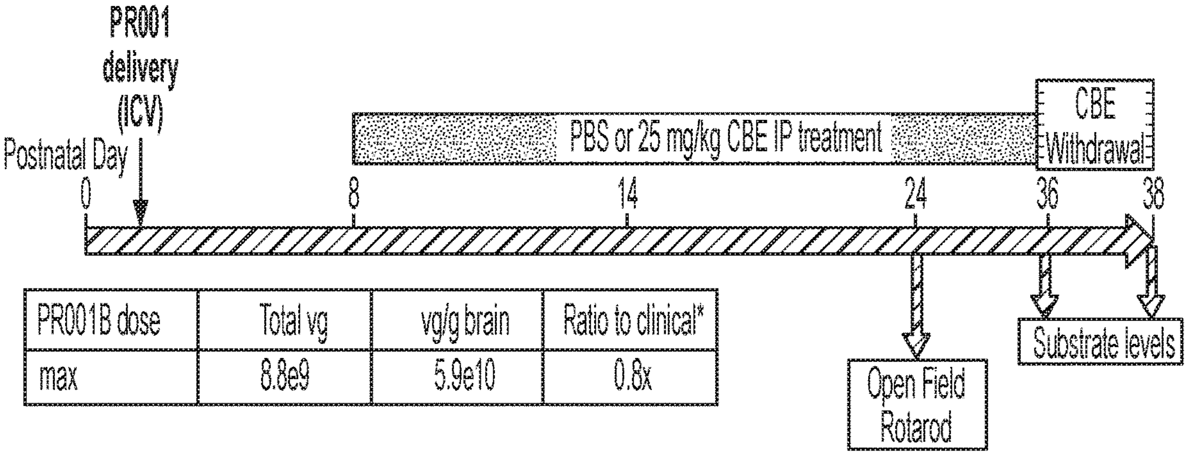
FIG. 10 is a schematic depicting one embodiment of a study design for maximal rAAV dose in a CBE mouse model. Briefly, rAAV was delivered by ICV injection at P3, and daily CBE treatment was initiated at P8. Behavior was assessed in the Open Field and Rotarod assays at P24-25 and substrate levels were measured at P36 and P38.

Based on the study described above, the 25 mg/kg CBE dose was selected since it produced behavioral deficits without impacting survival. To achieve widespread GBA1 distribution throughout the brain and transgene expression during CBE treatment, rAAV or excipient was delivered by intracerebroventricular (ICV) injection at postnatal day 3 (P3) followed by daily IP CBE or PBS treatment initiated at P8 (FIG. 10).

Figure 11:
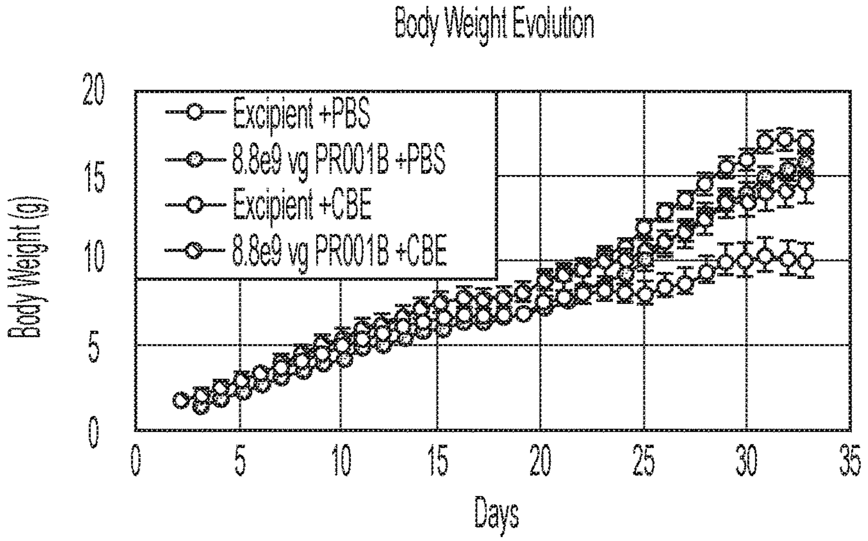
FIG. 11 shows representative data for in-life assessment of maximal rAAV dose in a CBE mouse model. At P3, mice were treated with either excipient or 8.8e9 vg rAAV via ICV delivery. Daily IP delivery of either PBS or 25 mg/kg CBE was initiated at P8. At the end of the study, half the mice were sacrificed one day after their last CBE dose at P36 (Day 1) while the remaining half went through 3 days of CBE withdrawal before sacrifice at P38 (Day 3). All treatment groups (excipient+PBS n=8, rAAV+PBS n=7, excipient+CBE n=8, and rAAV+CBE n=9) were weighed daily (top left), and the weight at P36 was analyzed (top right). Behavior was assessed by total distance traveled in Open Field at P23 (bottom left) and latency to fall on Rotarod at P24 (bottom right), evaluated for each animal as the median across 3 trials. Due to lethality, n=7 for the excipient+CBE group for the behavioral assays, while n=8 for all other groups. Means across animals are presented. Error bars are SEM. *p<0.05; ***p<0.001, nominal p-values for treatment groups by linear regression in the CBE-treated animals.
Figure 11:
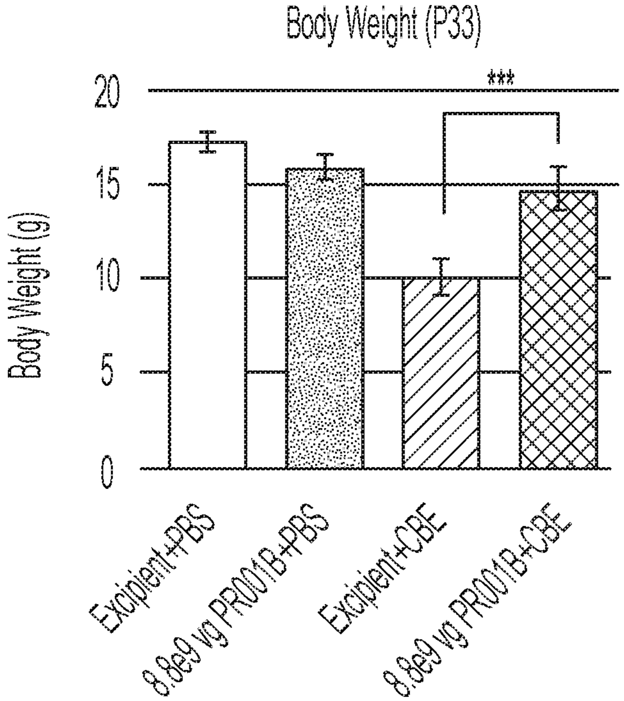
Figure 11:
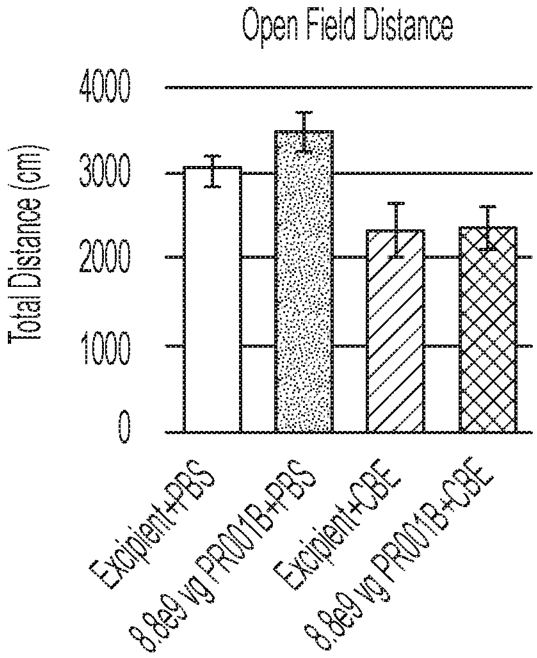
Figure 11:
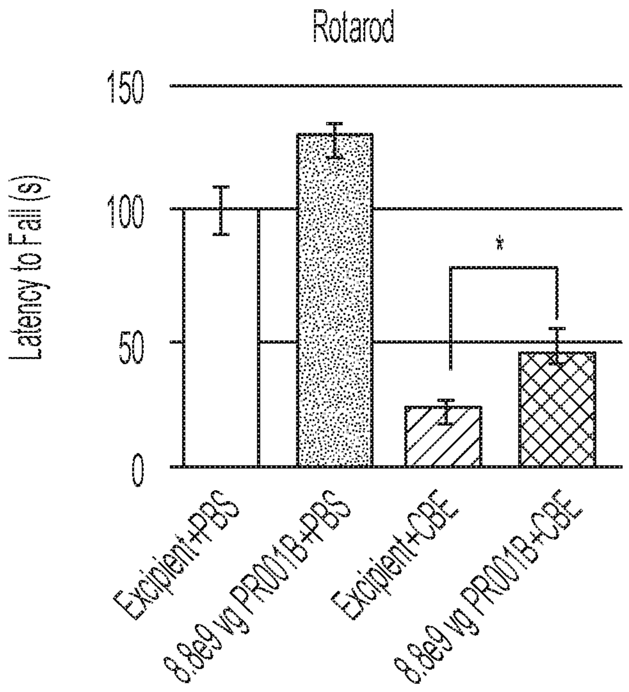

CBE-treated mice that received rAAV performed statistically significantly better on the rotarod than those that received excipient (FIG. 11). Mice in the variant vector treatment group did not differ from excipient treated mice in terms of other behavioral measures, such as the total distance traveled during testing (FIG. 11).

Figure 12:
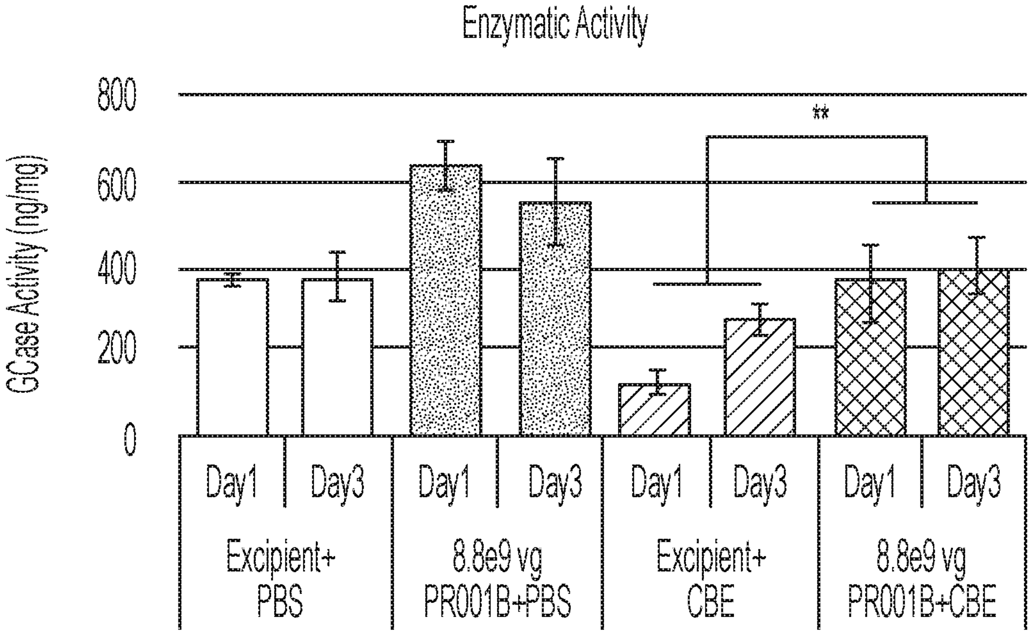
FIG. 12 shows representative data for biochemical assessment of maximal rAAV dose in a CBE mouse model. The cortex of all treatment groups (excipient+PBS n=8, rAAV+PBS n=7, excipient+CBE n=7, and rAAV+CBE n=9) was used to measure GCase activity (top left), GluSph levels (top right), GluCer levels (bottom left), and vector genomes (bottom right) in the groups before (Day 1) or after (Day 3) CBE withdrawal. Biodistribution is shown as vector genomes per 1 μg of genomic DNA. Means are presented. Error bars are SEM. (*)p<0.1; p<0.01; *p<0.001, nominal p-values for treatment groups by linear regression in the CBE-treated animals, with collection days and gender corrected for as covariates.
Figure 12:
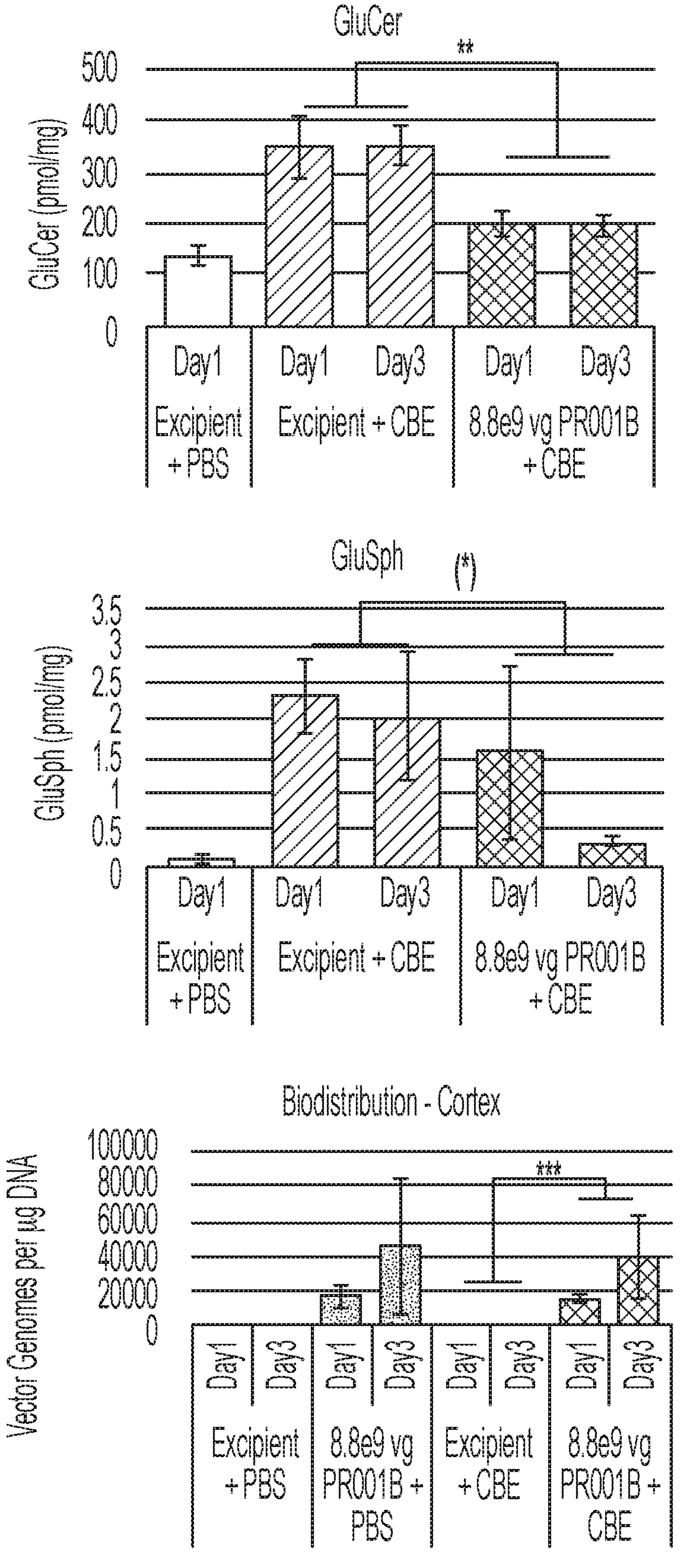

At the completion of the in-life study, half of the mice were sacrificed the day after the last CBE dose (P36, "Day 1") or after three days of CBE withdrawal (P38, "Day 3") for biochemical analysis (FIG. 12). Using a fluorometric enzyme assay performed in biological triplicate, GCase activity was assessed in the cortex. GCase activity was increased in mice that were treated with GBA1 rAAV, while CBE treatment reduced GCase activity. Additionally, mice that received both CBE and GBA1-rAAV had GCase activity levels that were similar to the PBS-treated group, indicating that delivery of rAAV is able to overcome the inhibition of GCase activity induced by CBE treatment. Lipid analysis was performed on the motor cortex of the mice to examine levels of the substrates GluCer and GluSph. Both lipids accumulated in the brains of mice given CBE, and rAAV treatment significantly reduced substrate accumulation.

Figure 13:
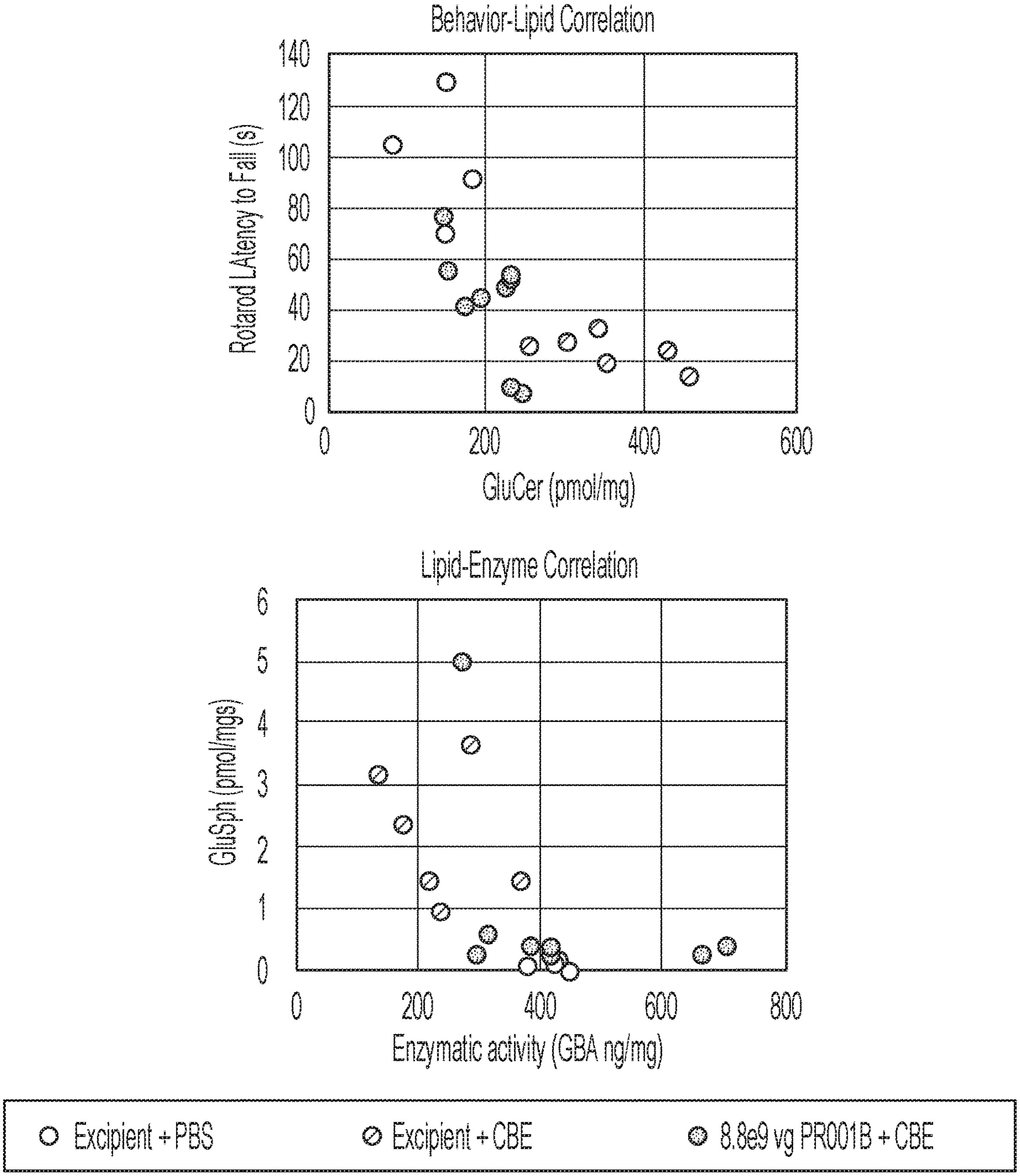
FIG. 13 shows representative data for behavioral and biochemical correlations in a CBE mouse model after administration of excipient+PBS, excipient+CBE, and rAAV+CBE treatment groups. Across treatment groups, performance on Rotarod was negatively correlated with GluCer accumulation (A, p=0.0012 by linear regression), and GluSph accumulation was negatively correlated with increased GCase activity (B, p=0.0086 by linear regression).
Figure 14:
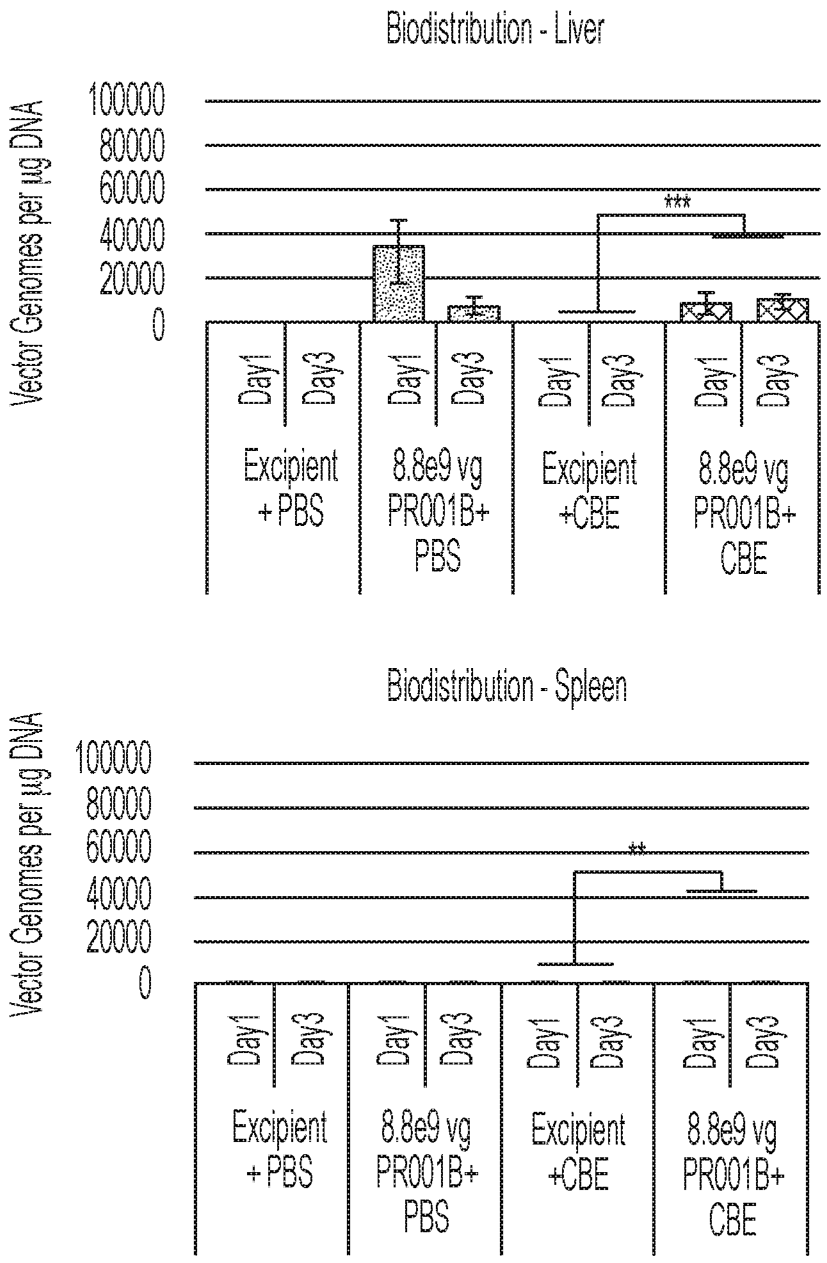
FIG. 14 shows representative data for biodistribution of GBA1 rAAV in a CBE mouse model. Presence of vector genomes was assessed in the liver, spleen, kidney, and gonads for all treatment groups (excipient+PBS n=8, rAAV+PBS n=7, excipient+CBE n=7, and rAAV+CBE n=9). Biodistribution is shown as vector genomes per 1 μg of genomic DNA. Vector genome presence was quantified by quantitative PCR using a vector reference standard curve; genomic DNA concentration was evaluated by A260 optical density measurement. Means are presented. Error bars are SEM. *p<0.05; p<0.01; *p<0.001, nominal p-values for treatment groups by linear regression in the CBE-treated animals, with collection days and gender corrected for as covariates.
Figure 14:
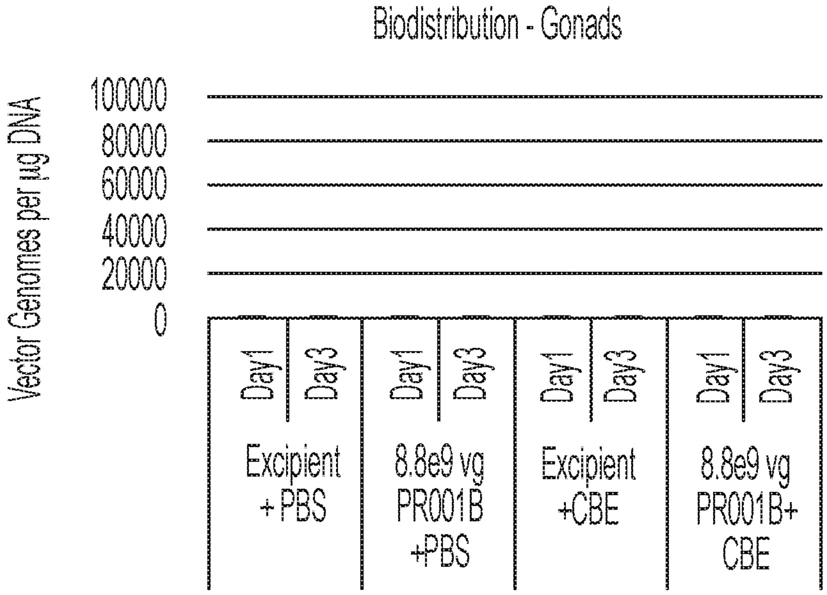
Figure 14:
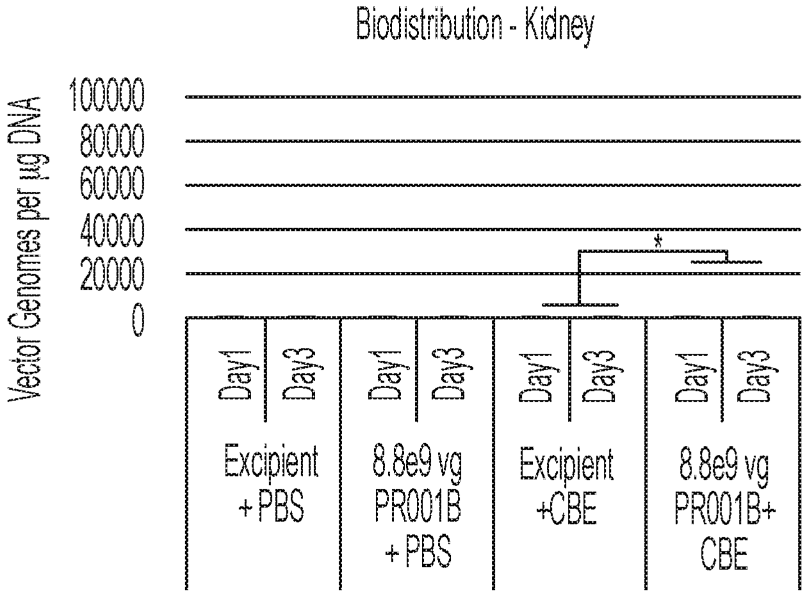

Lipid levels were negatively correlated with both GCase activity and performance on the Rotarod across treatment groups. The increased GCase activity after rAAV administration was associated with substrate reduction and enhanced motor function (FIG. 13). As shown in FIG. 14, preliminary biodistribution was assessed by vector genome presence, as measured by qPCR (with >100 vector genomes per 1 μg genomic DNA defined as positive). Mice that received GBA1-rAAV, both with and without CBE, were positive for rAAV vector genomes in the cortex, indicating that ICV delivery results in rAAV delivery to the cortex. Additionally, vector genomes were detected in the liver, few in spleen, and none in the heart, kidney or gonads. For all measures, there was no statistically significant difference between the Day 1 and Day 3 groups.

A larger study in the CBE model further explored efficacious doses of GBA1-rAAV in the CBE model. Using the 25 mg/kg CBE dose model, excipient or GBA1-rAAV was delivered via ICV at P3, and daily IP PBS or CBE treatment initiated at P8. Given the similarity between the groups with and without CBE withdrawal observed in the previous studies, all mice were sacrificed one day after the final CBE dose (P38-40). The effect of three different rAAV doses was assessed, resulting in the following five groups, with 10 mice (5M/5F) per group:

Excipient ICV+PBS IP

Excipient ICV+25 mg/kg CBE IP 3.2e9 vg (2.13e10 vg/g brain) rAAV ICV+25 mg/kg CBE IP 1.0e10 vg (6.67e10 vg/g brain) rAAV ICV+25 mg/kg CBE IP 3.2e10 vg (2.13e11 vg/g brain) rAAV ICV+25 mg/kg CBE IP.

Figure 15:
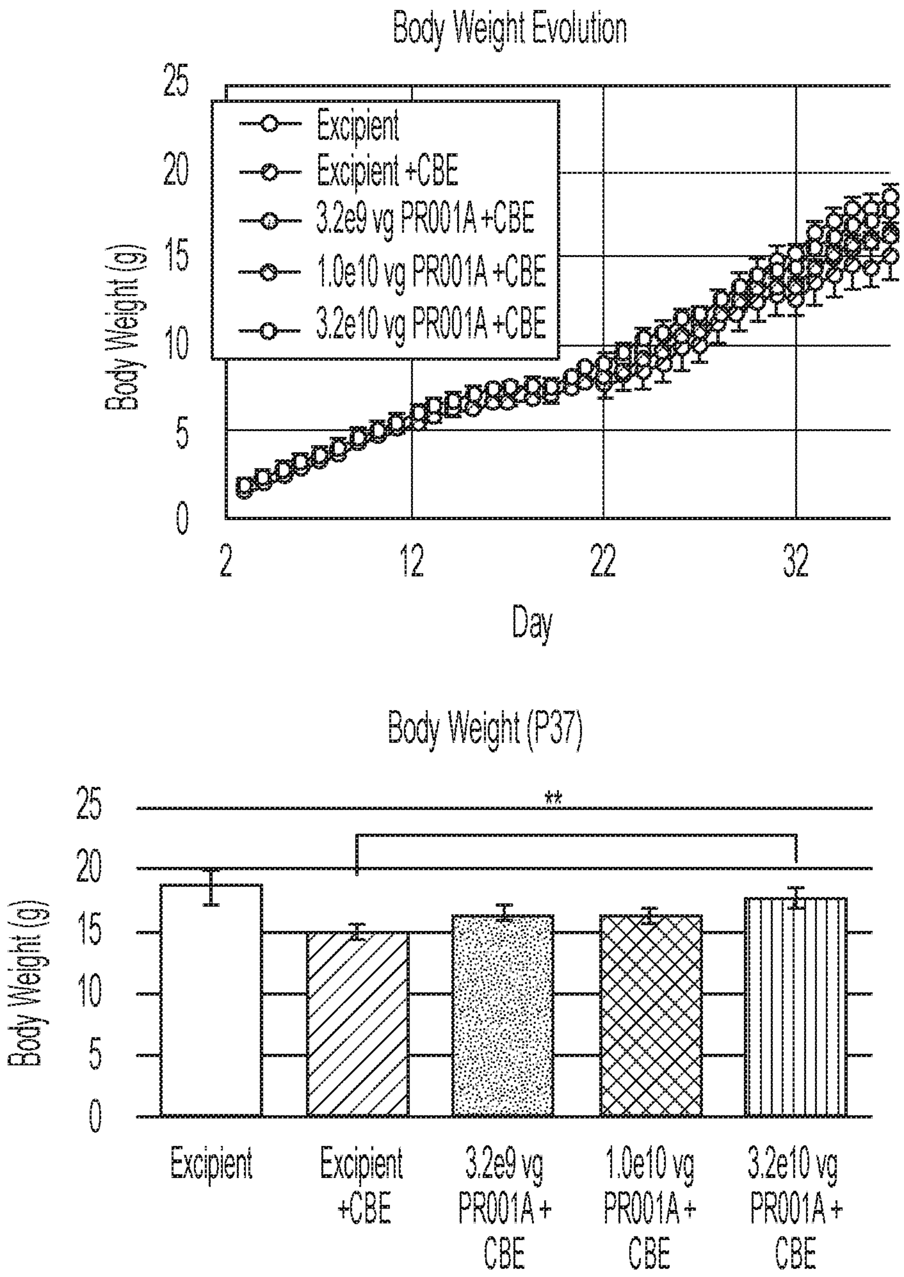
FIG. 15 shows representative data for in-life assessment of rAAV dose ranging in a CBE mouse model. Mice received excipient or one of three different doses of GBA1 rAAV by ICV delivery at P3: 3.2e9 vg, 1.0e10 vg, or 3.2e10 vg. At P8, daily IP treatment of 25 mg/kg CBE was initiated. Mice that received excipient and CBE or excipient and PBS served as controls. All treatment groups started with n=10 (5M/5F) per group. All mice were sacrificed one day after their final CBE dose (P38-P40). All treatment groups were weighed daily, and their weight was analyzed at P36. Motor performance was assessed by latency to fall on Rotarod at P24 and latency to traverse the Tapered Beam at P30. Due to early lethality, the number of mice participating in the behavioral assays was: excipient+PBS n=10, excipient+CBE n=9, and 3.2e9 vg rAAV+CBE n=6, 1.0e10 vg rAAV+CBE n=10, 3.2e10 vg rAAV+CBE n=7. Means are presented. Error bars are SEM; * p<0.05; **p<0.01 for nominal p-values by linear regression in the CBE-treated groups, with gender corrected for as a covariate.
Figure 15:
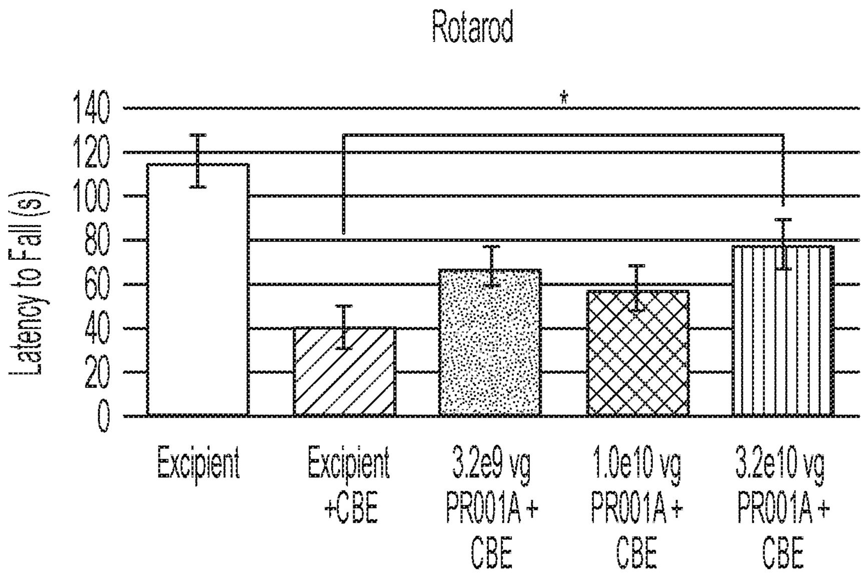
Figure 15:
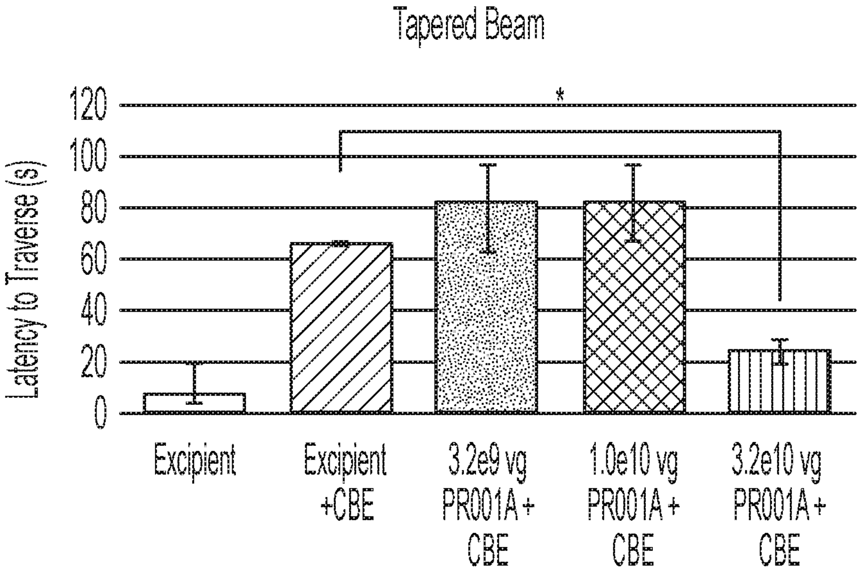

The highest dose of rAAV rescued the CBE treatment-related failure to gain weight at P37. Additionally, this dose resulted in a statistically significant increase in performance on the rotarod and tapered beam compared to the Excipient+CBE treated group (FIG. 15). Lethality was observed in several groups, including both excipient-treated and rAAV-treated groups (Excipient+PBS: 0; Excipient+25 mg/kg CBE: 1; 3.2e9 vg rAAV+25 mg/kg CBE: 4; 1.0e10 vg rAAV+25 mg/kg CBE: 0; 3.2e10 vg rAAV+25 mg/kg CBE: 3).

Figure 16:
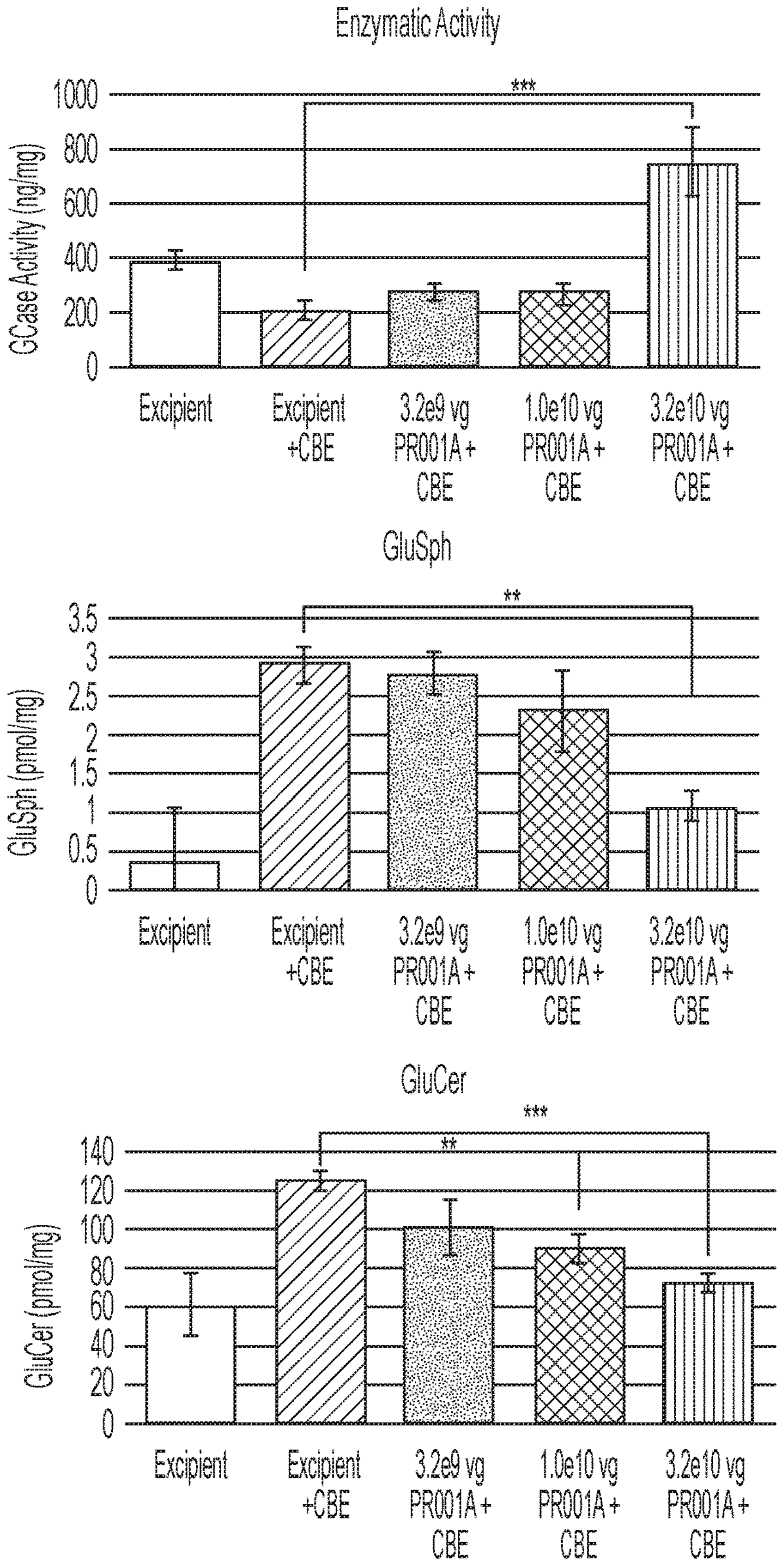
FIG. 16 shows representative data for biochemical assessment of rAAV dose ranging in a CBE mouse model. The cortex of all treatment groups (excipient+PBS n=10, excipient+CBE n=9, and 3.2e9 vg rAAV+CBE n=6, 1.0e10 vg rAAV+CBE n=10, 3.2e10 vg rAAV+CBE n=7) was used to measure GCase activity, GluSph levels, GluCer levels, and vector genomes. GCase activity is shown as ng of GCase per mg of total protein. GluSph and GluCer levels are shown as pmol per mg wet weight of the tissue. Biodistribution is shown as vector genomes per 1 μg of genomic DNA. Vector genome presence was quantified by quantitative PCR using a vector reference standard curve; genomic DNA concentration was evaluated by A260 optical density measurement. Vector genome presence was also measured in the liver (E). Means are presented. Error bars are SEM. p<0.01; *p<0.001 for nominal p-values by linear regression in the CBE-treated groups, with gender corrected for as a covariate.
Figure 16:
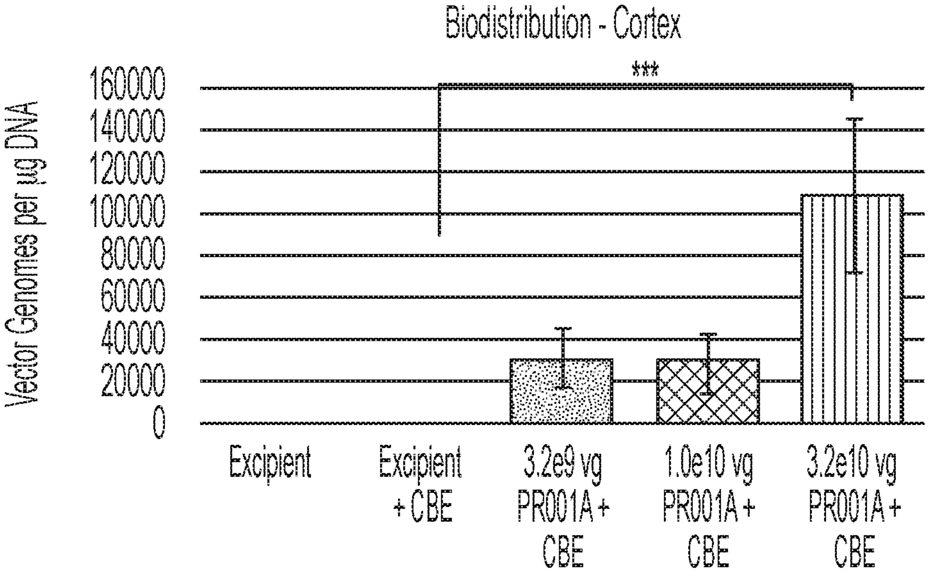
Figure 16:
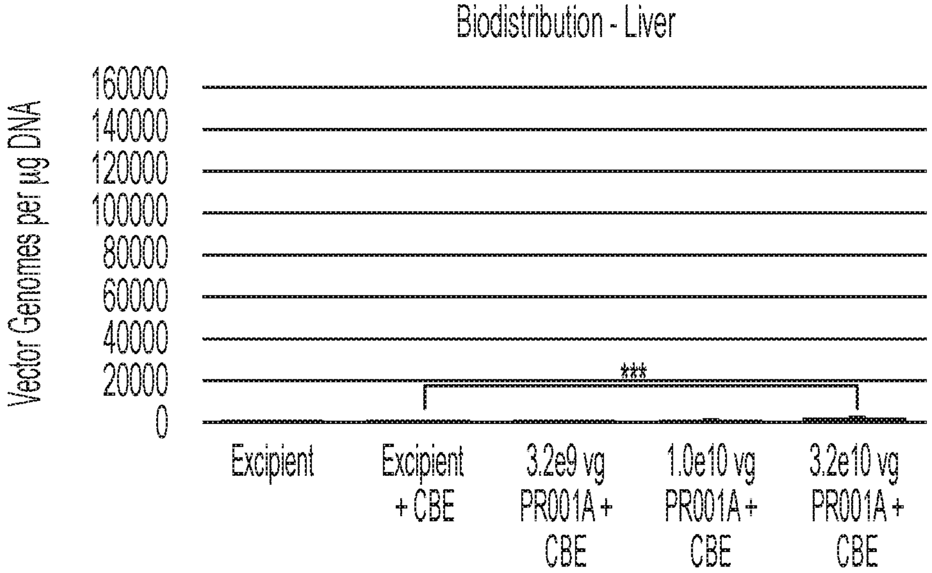

At the completion of the in-life study, mice were sacrificed for biochemical analysis (FIG. 16). GCase activity in the cortex was assessed in biological triplicates by a fluorometric assay. CBE-treated mice showed reduced GCase activity whereas mice that received a high rAAV dose showed a statistically significant increase in GCase activity compared to CBE treatment. CBE-treated mice also had accumulation of GluCer and GluSph, both of which were rescued by administering a high dose of rAAV.

In addition to the established chemical CBE model, GBA1-rAAV is also evaluated in the 4L/PS-NA genetic model, which is homozygous for the V394L GD mutation in Gba1 and is also partially deficient in saposins, which affect GCase localization and activity. These mice exhibit motor strength, coordination, and balance deficits, as evidenced by their performance in the beam walk, rotarod, and wire hang assays. Typically the lifespan of these mice is less than 22 weeks. In an initial study, 3 al of maximal titer virus was delivered by ICV at P23, with a final dose of 2.4e10 vg (6.0e10 vg/g brain). With 6 mice per group, the treatment groups were:

WT+Excipient ICV

4L/PS-NA+Excipient ICV

4L/PS-NA+2.4e10 vg (6.0e10 vg/g brain) rAAV ICV

Figure 17:
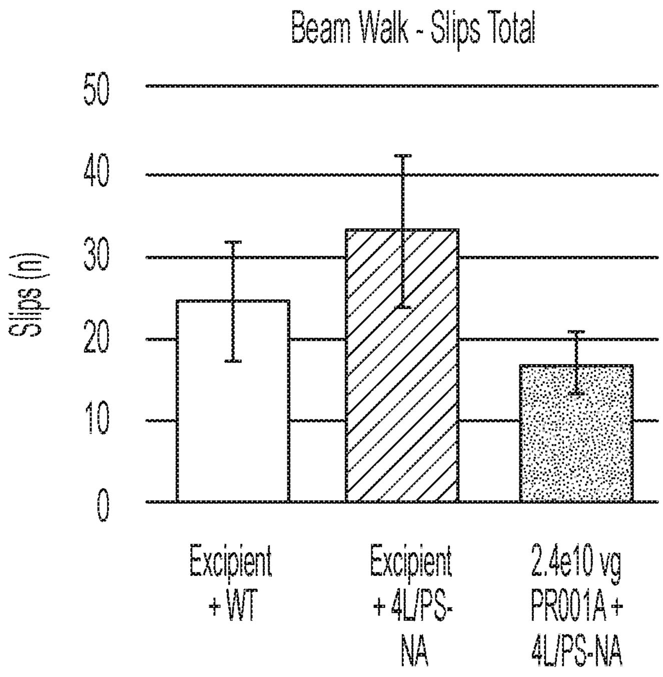
FIG. 17 shows representative data for tapered beam analysis in maximal dose GBA1 rAAV in a genetic mouse model. Motor performance of the treatment groups (WT+excipient, n=5), 4L/PS-NA+excipient (n=6), and 4L/PS-NA+rAAV (n=5)) was assayed by Beam Walk 4 weeks post rAAV administration. The total slips and active time are shown as total over 5 trials on different beams. Speed and slips per speed are shown as the average over 5 trials on different beams. Means are presented. Error bars are SEM.
Figure 17:
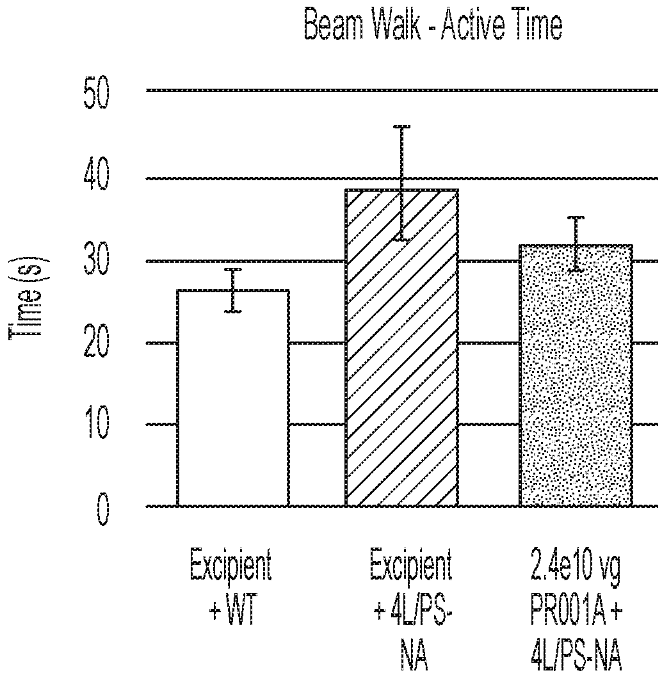
Figure 17:
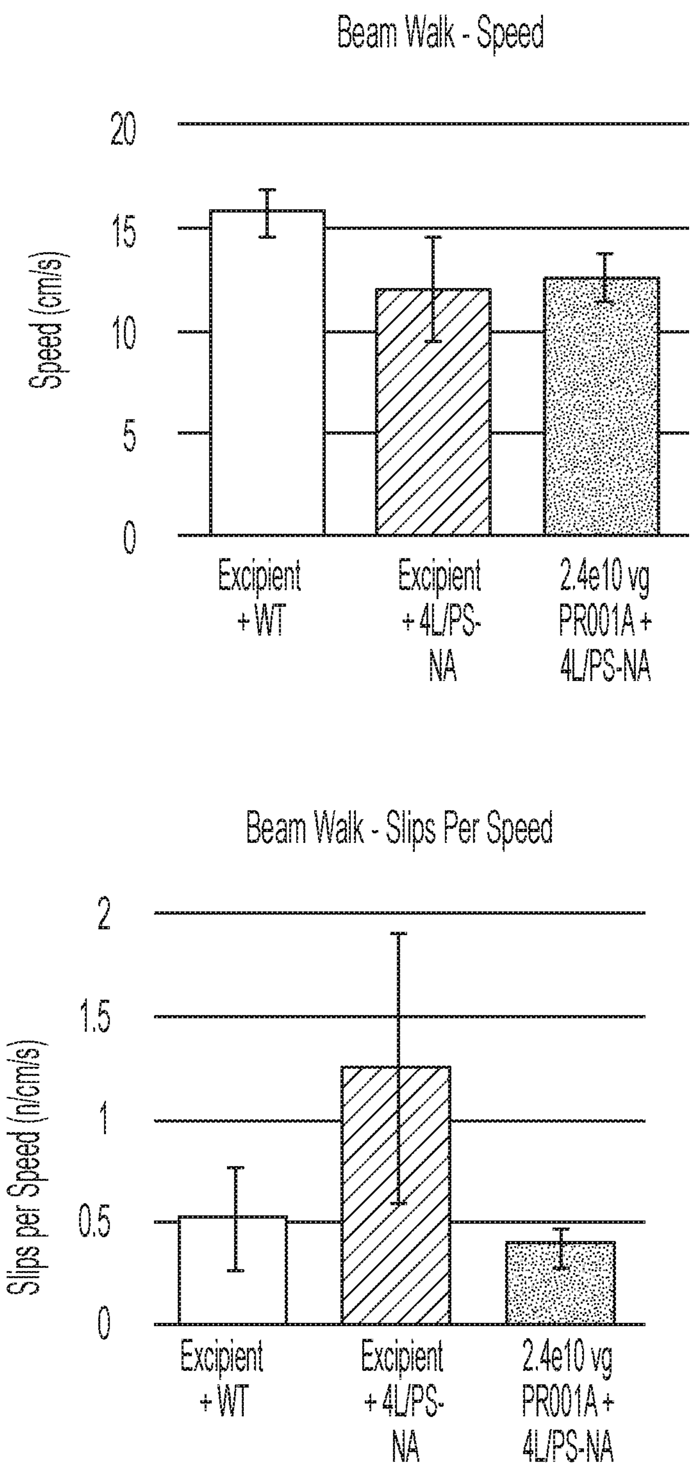

Motor performance by the beam walk test was assessed 4 weeks post-rAAV delivery. The group of mutant mice that received GBA1-rAAV showed a trend towards fewer total slips and fewer slips per speed when compared to mutant mice treated with excipient, restoring motor function to near WT levels (FIG. 17). Since the motor phenotypes become more severe as these mice age, their performance on this and other behavioral tests is assessed at later time points. At the completion of the in-life study, lipid levels, GCase activity, and biodistribution are assessed in these mice.

Additional lower doses of rAAV are currently being tested using the CBE model, corresponding to 0.03×, 0.1×, and 1× the proposed phase 1 high clinical dose. Each group includes 10 mice (5M/5F) per group:

Excipient ICV

Excipient ICV+25 mg/kg CBE IP 3.2e8 vg (2.13e9 vg/g brain) rAAV ICV+25 mg/kg CBE IP 1.0e9 vg (6.67e9 vg/g brain) rAAV ICV+25 mg/kg CBE IP 1.0e10 vg (6.67e10 vg/g brain) rAAV ICV+25 mg/kg CBE IP.

In addition to motor phenotypes, lipid levels and GCase activity are assessed in the cortex. Time course of treatments and analyses are also performed.

A larger dose ranging study was initiated to evaluate efficacy and safety data. 10 4L/PS-NA mice (5M/5F per group) were injected with 10 al of rAAV. Using an allometric brain weight calculation, the doses correlate to 0.15×, 1.5×, 4.4×, and 14.5× the proposed phase 1 high clinical dose. The injection groups consist of:

WT+Excipient ICV

4L/PS-NA+Excipient ICV

4L/PS-NA+4.3e9 vg (1.e10 vg/g brain) rAAV ICV

4L/PS-NA+4.3e10 vg (1.1e11 vg/g/brain) rAAV ICV

4L/PS-NA+1.3e11 vg (3.2e11 vg/g brain) rAAV ICV

4L/PS-NA+4.3e11 vg (1.1e12 vg/g brain) rAAV ICV.

A summary of nonclinical studies in the CBE model are shown in Table 3 below.

TABLE 3

| Summary of Results in CBE Mouse Model | | | | | | | | | |
|---|---|---|---|---|---|---|---|---|---|
| | | | Behavioral Changes | | | | | | |
| Test Material | Study Number | Dose Cohort | Rotarod | Tapered Beam | Open Field | Lipids | Enzyme | BD Brain | BD Liver |
| GBA1-rAAV | PRV-2018-005 Dose-ranging rAAV in CBE Model | 3.2e9 vg (2.13e10 vg/g brain) | NS | NS | NS | NS | NS | + | − |
| | | 1.10e10 vg (6.67e10 vg/g brain) | T | NS | NS | T/S | NS | + | + |
| | | 2.3e10 vg (2.13e11 vg/g brain) | S | S | NS | S | S | + | + |
| variant GBA1-rAAV | PRV-2018-005 Dose-ranging rAAV in CBE Model | 8.8e9 vg (5.9e10 vg/g brain) | S | N/A | NS | S | S | + | + |

Note that positive biodistribution is defined as >100 vg/1 μg genomic DNA.

Abbreviations: BD = biodistribution; NS = nonsignificant; T = trend; S = significant; N/A = not applicable; + = positive; − = negative.

Example 9: In Vitro Analysis of rAAV Vectors

Figure 18:
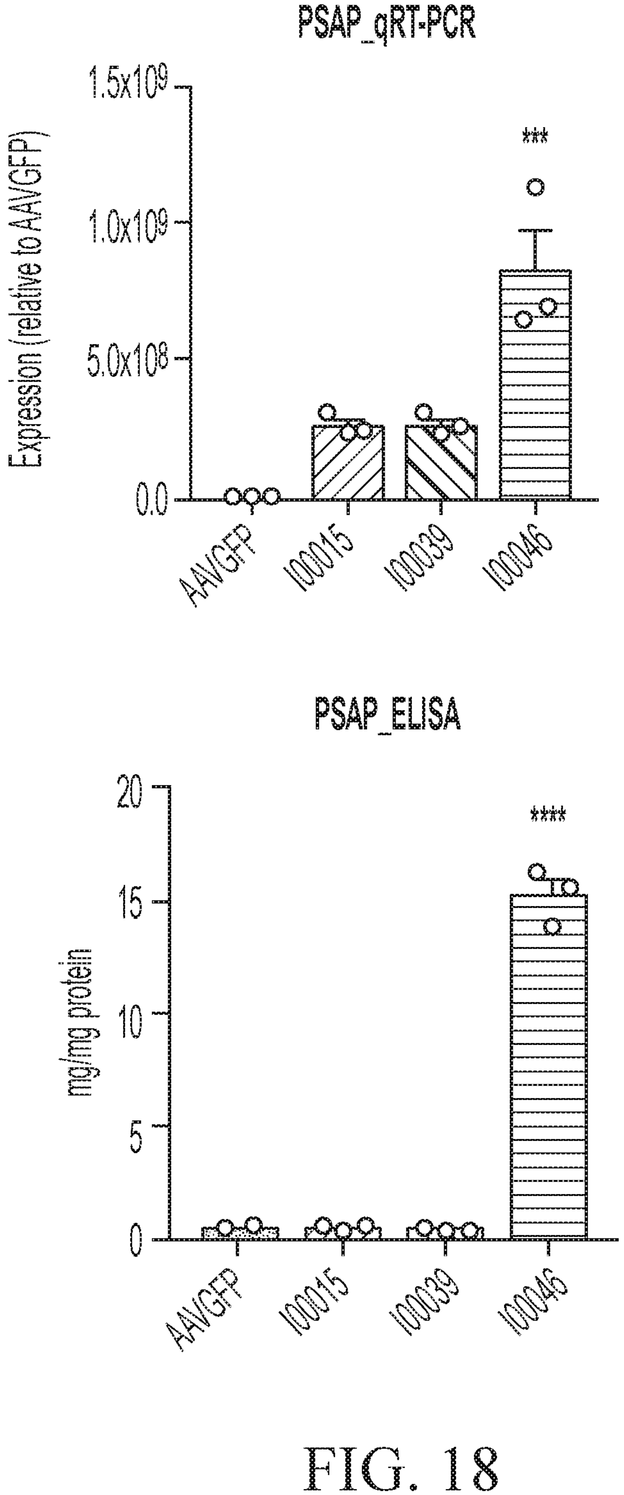
FIG. 18 shows representative data for in vitro expression of rAAV constructs encoding GBA1 in combination with Prosaposin (PSAP), SCARB2, and/or one or more inhibitory nucleic acids. Data indicate transfection of HEK293 cells with each construct resulted in overexpression of the transgenes of interest relative to GFP-transfected cells.
Figure 18:
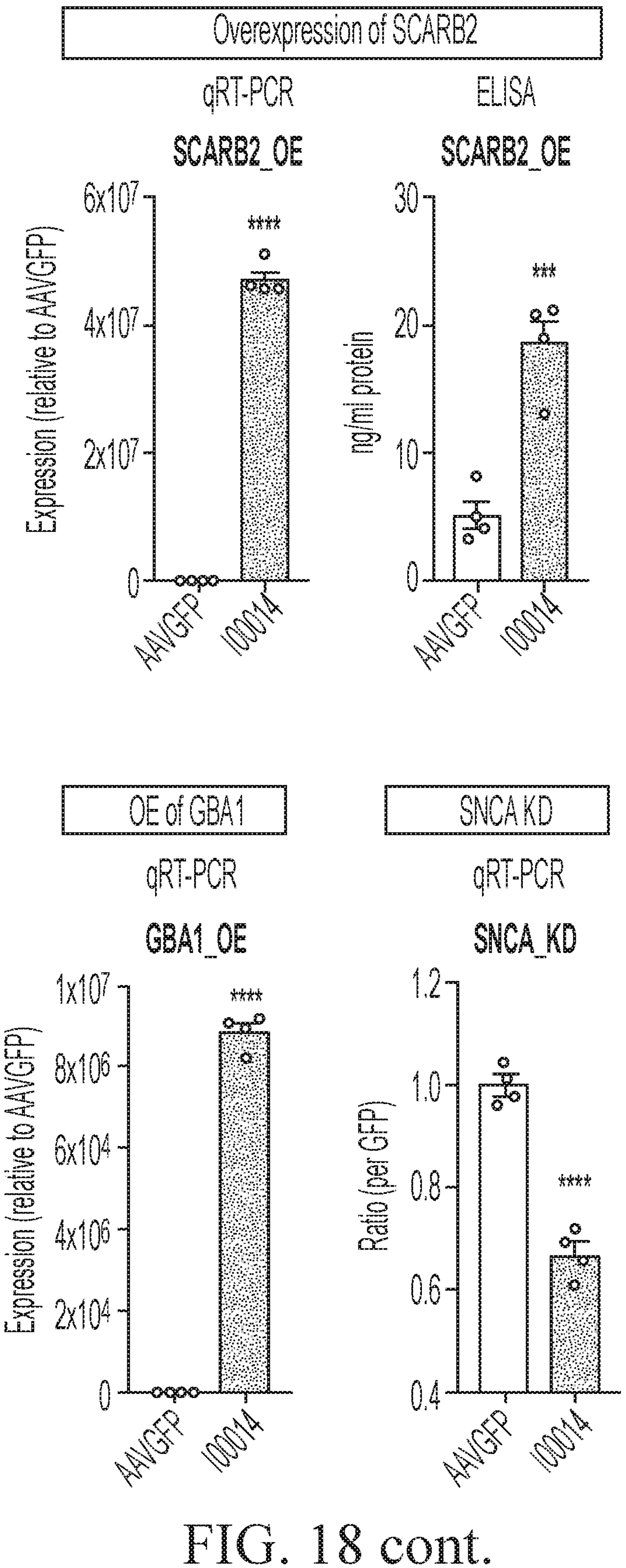

A pilot study was performed to assess in vitro activity of rAAV vectors encoding Prosaposin (PSAP) and SCARB2, alone or in combination with GBA1 and/or one or more inhibitory RNAs. One construct encoding PSAP and progranulin (PGRN) was also tested. Vectors tested include those shown in Table 4. "Opt" refers to a nucleic acid sequence codon optimized for expression in mammalian cells (e.g., human cells). FIG. 18 shows representative data indicating that transfection of HEK293 cells with each of the constructs resulted in overexpression of the corresponding gene product compared to mock transfected cells.

TABLE 4

| ID | Promoter | Inhibitory RNA | Promoter | Transgene |
|---|---|---|---|---|
| I00015 | JL_intronic | SCNA | JetLong | Opt-PSAP_GBA1 |
| I00039 | — | — | JetLong | Opt-PSAP-GRN |
| I00046 | — | — | | Opt-PSAP |
| I00014 | JetLong | SCNA | JetLong | Opt-SCARB2_GBA1 |

Example 10: ITR "D" Sequence Placement and Cell Transduction

Figure 20:
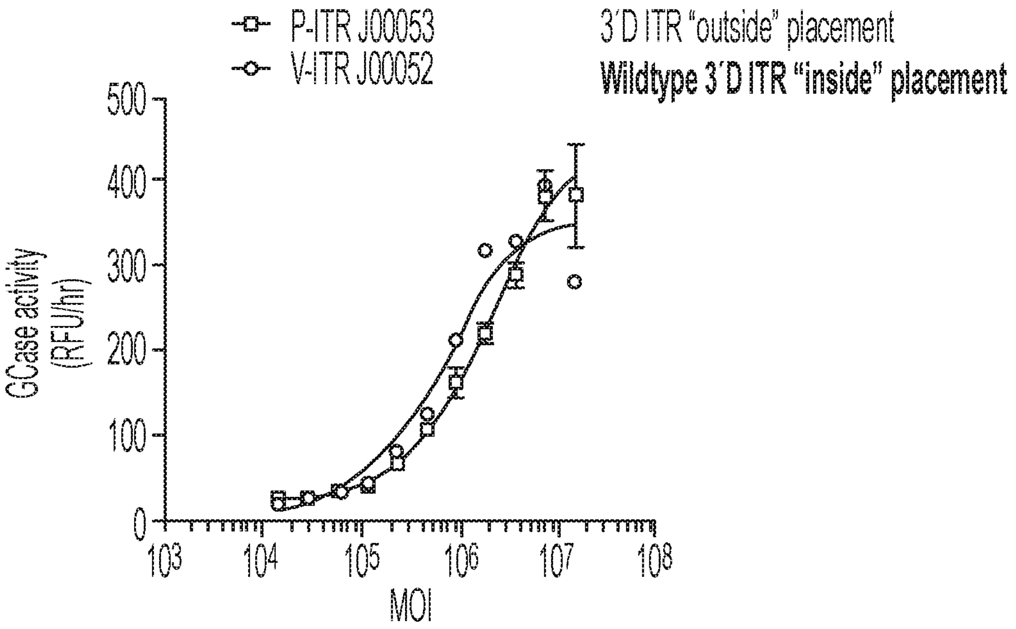
FIG. 20 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type ITRs.

The effect of placement of ITR "D" sequence on cell transduction of rAAV vectors was investigated. HEK 293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 19. Surprisingly, data indicate that rAAVs having the "D" sequence located in the "outside" position retain the ability to be packaged and transduce cells efficiently (FIG. 20).

Example 11: In Vitro Toxicity Studies

Fifty (50) mice were administered GBA1-encoding rAAVs via a 4 al intracerebroventricular (ICV) injection on post-natal day 3. All mice received daily intraperitoneal (IP) injections of conduritol B-epoxide (CBE) or PBS, depending on treatment group, from post-natal day 8 to the end of the study. Animals were euthanized 24 hours after their last IP dose. After euthanasia, target tissues were harvested, drop fixed in chilled 4% paraformaldehyde and stored at 4° C., then sent for histopathological processing and evaluation. There were eight (8) early death animals over the course of the study, which were not sent to or analyzed.

Tissues from the forty-two (42) animals euthanized at 38-40 days were trimmed, processed, and embedded in paraffin blocks. They were then sectioned at ~5 μm, stained with hematoxylin and eosin (H&E) and affixed to slides for evaluation.

There were no histopathologic findings or evidence of toxicity due to treatment with the rAAVs. In the mice treated with conduritol B-epoxide (CBE), there were findings in the central nervous system (CNS) that included glial scars and neuronal necrosis in the cerebral cortex, and neuronal necrosis in the brain stem and thoracic spinal cord. High dose rAAV treatment resulted in a notable reduction in the incidence of these CNS findings, while the low and mid dose virus had a dose dependent reduction in the incidence of glial scars in the cerebral cortex, with equivocal effects on the other CNS findings.

EQUIVALENTS

This Application incorporates by reference the contents of the following documents in their entirety: International PCT Application No. PCT/US2018/054227, filed Oct. 3, 2018; International PCT Application No. PCT/US2018/054223, filed Oct. 3, 2018; Provisional Application Ser. No. 62/567,311, filed Oct. 3, 2017, entitled "GENE THERAPIES FOR LYSOSOMAL DISORDERS"; 62/567,319, filed Oct. 3, 2017, entitled "GENE THERAPIES FOR LYSOSOMAL DISORDERS"; 62/567,301, filed Oct. 3, 2017, entitled "GENE THERAPIES FOR LYSOSOMAL DISORDERS"; 62/567,310, filed Oct. 3, 2017, entitled "GENE THERAPIES FOR LYSOSOMAL DISORDERS"; 62/567,303, filed Oct. 3, 2017, entitled "GENE THERAPIES FOR LYSOSOMAL DISORDERS"; and 62/567,305, filed Oct. 3, 2017, entitled "GENE THERAPIES FOR LYSOSOMAL DISORDERS".

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

SEQUENCES

In some embodiments, an expression cassette encoding one or more gene products (e.g., a first, second and/or third gene product) comprises or consists of (or encodes a peptide having) a sequence set forth in any one of SEQ ID NOs: 1, 2, 3, 4, 5, 6, 7, 8, 9, 10, 11, 12, 13, 14, 15, 16, 17, 18, 19, 20, 21, 22, 23, 24, or 25. In some embodiments, a gene product is encoded by a portion (e.g., fragment) of any one of SEQ ID NOs: 1, 2, 3, 4, 5, 6, 7, 8, 9, 10, 11, 12, 13, 14, 15, 16, 17, 18, 19, 20, 21, 22, 23, 24, or 25.

What is claimed is:

1. An isolated nucleic acid comprising (i) an expression construct comprising a transgene comprising (a) a beta-Glucocerebrosidase (Gcase) protein coding sequence comprising the sequence set forth in SEQ ID NO: 15; and (b) a coding sequence encoding an inhibitory nucleic acid targeting α-Synuclein, wherein the inhibitory nucleic acid is encoded by the sequence set forth in SEQ ID NO: 20; and (ii) two adeno-associated virus (AAV) inverted terminal repeats (ITR) sequences flanking the expression construct.

2. The isolated nucleic acid of claim 1, wherein the transgene is operably linked to a promoter.

3. The isolated nucleic acid of claim 2, wherein the promoter is a chicken beta actin (CBA) promoter.

4. The isolated nucleic acid of claim 2, further comprising a CMV enhancer.

5. The isolated nucleic acid of claim 1, further comprising a Woodchuck Hepatitis Virus Posttranscriptional Regulatory Element (WPRE).

6. The isolated nucleic acid of claim 1, further comprising a Bovine Growth Hormone poly A signal tail.

7. The isolated nucleic acid of claim 1, wherein each ITR sequence is a wild-type AAV2 ITR sequence.

8. The isolated nucleic acid of claim 1, wherein each ITR sequence comprises a "D" region (SEQ ID NO: 27) that is proximal to the expression construct.

9. The isolated nucleic acid of claim 1, wherein at least one of the ITR sequences comprises a "D" region (SEQ ID NO: 27) positioned on the outside of the ITR sequence relative to the expression construct.

10. The isolated nucleic acid of claim 1, wherein the ITR sequence positioned 5' relative to the expression construct comprises a "D" region (SEQ ID NO: 27) that is proximal to the expression construct, and the ITR sequence positioned 3' relative to the expression construct comprises a "D" region (SEQ ID NO: 27) positioned on the outside of the ITR sequence relative to the expression construct.

11. The isolated nucleic acid of claim 1, wherein the nucleic acid sequence of the 5' ITR is nucleotides 1-145 of SEQ ID NO: 1 and the nucleic acid sequence of the 3' ITR is nucleic nucleotides 3867-4011 of SEQ ID NO: 1.

12. The isolated nucleic acid of claim 11, further comprising a TRY region between the 5' ITR and the expression construct, wherein the TRY region has the sequence set forth in SEQ ID NO: 28.

13. The isolated nucleic acid claim 1, wherein the transgene comprises the sequence set forth in nucleotides 1105-1367 of SEQ ID NO: 13.

14. A recombinant adeno-associated virus (rAAV) vector comprising (i) an expression construct comprising a transgene comprising (a) a Gcase protein coding sequence comprising the sequence set forth in SEQ ID NO: 15; and (b) a coding sequence encoding an inhibitory nucleic acid targeting α-Synuclein, wherein the inhibitory nucleic acid is encoded by the sequence set forth in SEQ ID NO: 20; and (ii) two AAV ITR sequences flanking the expression construct.

15. A plasmid comprising the rAAV vector of claim 14.

16. The rAAV vector of claim 14, wherein the promoter is a CBA promoter.

17. The rAAV vector of claim 16, further comprising a CMV enhancer.

18. The rAAV vector of claim 14, further comprising a WPRE.

19. The rAAV vector of claim 14, further comprising a Bovine Growth Hormone poly A signal tail.

20. The rAAV vector of claim 14, wherein each ITR sequence is a wild-type AAV2 ITR sequence.

21. The rAAV vector of claim 14, wherein each ITR sequence comprises a "D" region (SEQ ID NO: 27) that is proximal to the expression construct.

22. The rAAV vector of claim 14, wherein at least one of the ITR sequences comprises a "D" region (SEQ ID NO: 27) positioned on the outside of the ITR sequence relative to the expression construct.

23. The rAAV vector of claim 14, wherein the ITR sequence positioned 5' relative to the expression construct comprises a "D" region (SEQ ID NO: 27) that is proximal to the expression construct, and the ITR sequence positioned 3' relative to the expression construct comprises a "D" region (SEQ ID NO: 27) positioned on the outside of the ITR sequence relative to the expression construct.

24. The rAAV vector of claim 14, wherein the nucleic acid sequence of the 5' ITR is nucleotides 1-145 of SEQ ID NO: 1 and the nucleic acid sequence of the 3' ITR is nucleic nucleotides 3867-4011 of SEQ ID NO: 1.

25. The rAAV vector of claim 24, further comprising a TRY region between the 5' ITR and the expression construct, wherein the TRY region has the sequence set forth in SEQ ID NO: 28.

26. The rAAV vector of claim 14, wherein the transgene comprises the sequence set forth in nucleotides 1105-1367 of SEQ ID NO: 13.

27. The rAAV vector of claim 14, wherein the transgene is operably linked to a promoter.

28. A rAAV comprising:

(i) an AAV capsid protein; and (ii) the rAAV vector of claim 27.

29. The rAAV of claim 28, wherein the AAV capsid protein is AAV9 capsid protein.

30. A method for treating a subject having Lewy Body Dementia associated with a GBA1 mutation, the method comprising administering to the subject the rAAV of claim 29, wherein the administration comprises direct injection to the central nervous system (CNS) of the subject.

31. The method of claim 30, wherein the direct injection is intracerebral injection, intraparenchymal injection, intrathecal injection, intra-cisterna *magna* injection or any combination thereof.

32. The method of claim 30, wherein the direct injection to the CNS of the subject comprises convection enhanced delivery (CED).

33. A method of producing the rAAV of claim 28, the method comprising:

(i) delivering to a cell a first vector encoding one or more AAV rep proteins and/or one or more AAV cap proteins, and the rAAV vector;

(ii) culturing the cells of (i) under conditions allowing for packaging the rAAV; and (iii) harvesting the cultured host cells or the culture medium for collection of the rAAV.

34. A rAAV vector comprising a nucleic acid comprising, in 5' to 3' order:

(a) a 5' AAV ITR;

(b) a CMV enhancer;

(c) a CBA promoter;

(d) a transgene comprising a Gcase protein coding sequence comprising the sequence set forth in SEQ ID NO: 15 and a coding sequence encoding an inhibitory nucleic acid targeting α-Synuclein, wherein the inhibitory nucleic acid is encoded by the sequence set forth in SEQ ID NO: 20;

(e) a WPRE;

(f) a Bovine Growth Hormone poly A signal tail; and (g) a 3' AAV ITR.

35. The rAAV vector of claim 34, wherein the transgene comprises the sequence set forth in nucleotides 1105-1367 of SEQ ID NO: 13.

36. A rAAV comprising:

(i) an AAV capsid protein; and (ii) the rAAV vector of claim 34.

37. The rAAV of claim 36, wherein the AAV capsid protein is AAV9 capsid protein.

38. A Baculovirus vector comprising (i) the sequence set forth in SEQ ID NO: 15, and (ii) a coding sequence encoding an inhibitory nucleic acid targeting α-Synuclein, wherein the inhibitory nucleic acid is encoded by the sequence set forth in SEQ ID NO: 20.

39. A cell comprising:

(i) a first vector encoding one or more AAV rep proteins and/or one or more AAV cap proteins; and (il) a second vector comprising an expression construct comprising a Gcase protein coding sequence comprising the sequence set forth in SEQ ID NO: 15 and a coding sequence encoding an inhibitory nucleic acid targeting α-Synuclein, wherein the inhibitory nucleic acid is encoded by the sequence set forth in SEQ ID NO: 20.

40. The cell of claim 39, wherein the first vector is a plasmid and the second vector is a plasmid.

41. The cell of claim 39, wherein the cell is a mammalian cell.

42. The cell of claim 41, wherein the mammalian cell is a HEK293 cell.

43. The cell of claim 39, wherein the first vector is a Baculovirus vector and the second vector is a Baculovirus vector.

44. The cell of claim 43, wherein the cell is an insect cell.

* * * * *

SEQUENCE LISTING

<160> NUMBER OF SEQ ID NOS: 31

<210> SEQ ID NO 1
<211> LENGTH: 10697
<212> TYPE: DNA
<213> ORGANISM: Artificial Sequence
<220> FEATURE:
<223> OTHER INFORMATION: Synthetic polynucleotide

<400> SEQUENCE: 1

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
cctagttatt aatagtaatc aattacgggg tcattagttc atagcccata tatggagttc    360
cgcgttacat aacttacggt aaatggcccg cctggctgac cgcccaacga cccccgccca    420
ttgacgtcaa taatgacgta tgttcccata gtaacgccaa tagggacttt ccattgacgt    480
caatgggtgg actatttacg gtaaactgcc cacttggcag tacatcaagt gtatcatatg    540
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tattttttaa ttattttgtg cagcgatggg ggcggggggg    780
ggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgttttctg tggctgcgtg aaagccttga ggggctccgg   1140
gagctagagc ctctgctaac catgttcatg ccttcttctt tttcctacag ctcctgggca   1200
acgtgctggt tattgtgctg tctcatcatt ttggcaaaga attcctcgaa gatccgaagg   1260
gaaagtcttc cacgactgtg ggatccgttc gaagatatca ccggttgagc caccatggaa   1320
ttcagcagcc ccagcagaga ggaatgcccc aagcctctga gccgggtgtc aatcatggcc   1380
ggatctctga caggactgct gctgcttcag gccgtgtctt gggcttctgg cgctagacct   1440
tgcatcccca agagcttcgg ctacagcagc gtcgtgtgcg tgtgcaatgc cacctactgc   1500
gacagcttcg accctcctac ctttcctgct ctgggcacct tcagcagata cgagagcacc   1560
agatccggca gacggatgga actgagcatg ggacccatcc aggccaatca cacaggcact   1620
ggcctgctgc tgacactgca gcctgagcag aaattccaga aagtgaaagg cttcggcgga   1680
gccatgacag atgccgccgc tctgaatatc ctggctctgt ctccaccagc tcagaacctg   1740
ctgctcaaga gctacttcag cgaggaaggc atcggctaca acatcatcag agtgcccatg   1800
gccagctgcg acttcagcat caggacctac acctacgccg acacacccga cgatttccag   1860
ctgcacaact tcagcctgcc tgaagaggac accaagctga agatccctct gatccacaga   1920
gccctgcagc tggcacaaag acccgtgtca ctgctggcct ctccatggac atctcccacc   1980
tggctgaaaa caaatggcgc cgtgaatggc aagggcagcc tgaaaggcca acctggcgac   2040
```

atctaccacc agacctgggc cagatacttc gtgaagttcc tggacgccta tgccgagcac 2100
aagctgcagt tttgggccgt gacagccgag aacgaacctt ctgctggact gctgagcggc 2160 taccccttc agtgcctggg ctttacaccc gagcaccagc gggactttat cgcccgtgat 2220
ctgggaccca cactggccaa tagcacccac cataatgtgc ggctgctgat gctggacgac 2280
cagagactgc ttctgcccca ctgggctaaa gtggtgctga cagatcctga ggccgccaaa 2340
tacgtgcacg gaatcgccgt gcactggtat ctggactttc tggcccctgc caaggccaca 2400
ctgggagaga cacacagact gttccccaac accatgctgt tcgccagcga agcctgtgtg 2460
ggcagcaagt tttgggaaca gagcgtgcgg ctcggcagct gggatagagg catgcagtac 2520
agccacagca tcatcaccaa cctgctgtac cacgtcgtcg gctggaccga ctggaatctg 2580
gccctgaatc ctgaaggcgg ccctaactgg gtccgaaact tcgtggacag ccccatcatc 2640
gtggacatca ccaaggacac cttctacaag cagcccatgt tctaccacct gggacacttc 2700
agcaagttca tccccgaggg ctctcagcgc gttggactgg tggcttccca gaagaacgat 2760
ctggacgccg tggctctgat gcaccctgat ggatctgctg tggtggtggt cctgaaccgc 2820
agcagcaaag atgtgcccct gaccatcaag gatcccgccg tgggattcct ggaaacaatc 2880
agccctggct actccatcca cacctacctg tggcgtagac agtgacaatt gttaattaag 2940
tttaaaccct cgaggccgca agcttatcga taatcaacct ctggattaca aaatttgtga 3000
aagattgact ggtattctta actatgttgc tccttttacg ctatgtggat acgctgcttt 3060
aatgcctttg tatcatgcta ttgcttcccg tatggctttc attttctcct ccttgtataa 3120
atcctggttg ctgtctcttt atgaggagtt gtggcccgtt gtcaggcaac gtggcgtggt 3180
gtgcactgtg tttgctgacg caacccccac tggttggggc attgccacca cctgtcagct 3240
cctttccggg actttcgctt tccccctccc tattgccacg gcggaactca tcgccgcctg 3300
ccttgcccgc tgctggacag gggctcggct gttgggcact gacaattccg tggtgttgtc 3360
ggggaaatca tcgtcctttc cttggctgct cgcctgtgtt gccacctgga ttctgcgcgg 3420
gacgtccttc tgctacgtcc cttcggccct caatccagcg gaccttcctt cccgcggcct 3480
gctgccggct ctgcggcctc ttccgcgtct tcgccttcgc cctcagacga gtcggatctc 3540
cctttgggcc gcctccccgc atcgataccg tcgactagag ctcgctgatc agcctcgact 3600
gtgccttcta gttgccagcc atctgttgtt tgcccctccc ccgtgccttc cttgaccctg 3660
gaaggtgcca ctcccactgt cctttcctaa taaaatgagg aaattgcatc gcattgtctg 3720
agtaggtgtc attctattct ggggggtggg gtggggcagg acagcaaggg ggaggattgg 3780
gaagacaata gcaggcatgc tggggagaga tccacgataa caaacagctt ttttggggtg 3840
aacatattga ctgaattccc tgcaggttgg ccactccctc tctgcgcgct cgctcgctca 3900
ctgaggccgc ccgggcaaag cccgggcgtc gggcgacctt tggtcgcccg gcctcagtga 3960
gcgagcgagc gcgcagagag ggagtggcca actccatcac taggggttcc tgcggccgct 4020
cgtacggtct cgaggaattc ctgcaggata acttgccaac ctcattctaa aatgtatata 4080
gaagcccaaa agacaataac aaaaatattc ttgtagaaca aaatgggaaa gaatgttcca 4140
ctaaatatca agatttagag caaagcatga gatgtgtggg gatagacagt gaggctgata 4200
aaatagagta gagctcagaa acagacccat tgatatatgt aagtgaccta tgaaaaaaat 4260
atggcatttt acaatgggaa aatgatggtc tttttctttt ttagaaaaac agggaaatat 4320
atttatatgt aaaaaataaa agggaaccca tatgtcatac catacacaca aaaaaattcc 4380

-continued agtgaattat aagtctaaat ggagaaggca aaactttaaa tcttttagaa aataatatag 4440
aagcatgcag accagcctgg ccaacatgat gaaaccctct ctactaataa taaaatcagt 4500
agaactactc aggactactt tgagtgggaa gtccttttct atgaagactt ctttggccaa 4560
aattaggctc taaatgcaag gagatagtgc atcatgcctg gctgcactta ctgataaatg 4620
atgttatcac catctttaac caaatgcaca ggaacaagtt atggtactga tgtgctggat 4680
tgagaaggag ctctacttcc ttgacaggac acatttgtat caacttaaaa aagcagattt 4740
ttgccagcag aactattcat tcagaggtag gaaacttaga atagatgatg tcactgatta 4800
gcatggcttc cccatctcca cagctgcttc ccacccaggt tgcccacagt tgagtttgtc 4860
cagtgctcag ggctgcccac tctcagtaag aagccccaca ccagcccctc tccaaatatg 4920
ttggctgttc cttccattaa agtgacccca ctttagagca gcaagtggat ttctgtttct 4980
tacagttcag gaaggaggag tcagctgtga gaacctggag cctgagatgc ttctaagtcc 5040
cactgctact ggggtcaggg aagccagact ccagcatcag cagtcaggag cactaagccc 5100
ttgccaacat cctgtttctc agagaaactg cttccattat aatggttgtc ctttttttaag 5160 ctatcaagcc aaacaaccag tgtctaccat tattctcatc acctgaagcc aagggttcta 5220
gcaaaagtca agctgtcttg taatggttga tgtgcctcca gcttctgtct tcagtcactc 5280
cactcttagc ctgctctgaa tcaactctga ccacagttcc ctggagcccc tgccacctgc 5340
tgcccctgcc accttctcca tctgcagtgc tgtgcagcct tctgcactct tgcagagcta 5400
ataggtggag acttgaagga agaggaggaa agtttctcat aatagccttg ctgcaagctc 5460
aaatgggagg tgggcactgt gcccaggagc cttggagcaa aggctgtgcc caacctctga 5520
ctgcatccag gtttggtctt gacagagata agaagccctg gcttttggag ccaaaatcta 5580
ggtcagactt aggcaggatt ctcaaagttt atcagcagaa catgaggcag aagacccttt 5640
ctgctccagc ttcttcaggc tcaaccttca tcagaataga tagaaagaga ggctgtgagg 5700
gttcttaaaa cagaagcaaa tctgactcag agaataaaca acctcctagt aaactacagc 5760
ttagacagag catctggtgg tgagtgtgct cagtgtccta ctcaactgtc tggtatcagc 5820
cctcatgagg acttctcttc tttccctcat agacctccat ctctgttttc cttagcctgc 5880
agaaatctgg atggctattc acagaatgcc tgtgctttca gagttgcatt ttttctctgg 5940
tattctggtt caagcatttg aaggtaggaa aggttctcca agtgcaagaa agccagccct 6000
gagcctcaac tgcctggcta gtgtggtcag taggatgcaa aggctgttga atgccacaag 6060
gccaaacttt aacctgtgta ccacaagcct agcagcagag gcagctctgc tcactggaac 6120
tctctgtctt ctttctcctg agccttttct tttcctgagt tttctagctc tcctcaacct 6180
tacctctgcc ctacccagga caaacccaag agccactgtt tctgtgatgt cctctccagc 6240
cctaattagg catcatgact tcagcctgac cttccatgct cagaagcagt gctaatccac 6300
ttcagatgag ctgctctatg caacacaggc agagcctaca aacctttgca ccagagccct 6360
ccacatatca gtgtttgttc atactcactt caacagcaaa tgtgactgct gagattaaga 6420
ttttacacaa gatggtctgt aatttcacag ttagttttat cccattaggt atgaaagaat 6480
tagcataatt ccccttaaac atgaatgaat cttagatttt ttaataaata gttttggaag 6540
taaagacaga gacatcagga gcacaaggaa tagcctgaga ggacaaacag aacaagaaag 6600
agtctggaaa tacacaggat gttcttggcc tcctcaaagc aagtgcaagc agatagtacc 6660
agcagcccca ggctatcaga gcccagtgaa gagaagtacc atgaaagcca cagctctaac 6720
caccctgttc cagagtgaca gacagtcccc aagacaagcc agcctgagcc agagagagaa 6780

-continued

```
ctgcaagaga aagtttctaa tttaggttct gttagattca gacaagtgca ggtcatcctc   6840
tctccacagc tactcacctc tccagcctaa caaagcctgc agtccacact ccaaccctgg   6900
tgtctcacct cctagcctct cccaacatcc tgctctctga ccatcttctg catctctcat   6960
ctcaccatct cccactgtct acagcctact cttgcaacta ccatctcatt ttctgacatc   7020
ctgtctacat cttctgccat actctgccat ctaccatacc acctcttacc atctaccaca   7080
ccatctttta tctccatccc tctcagaagc ctccaagctg aatcctgctt tatgtgttca   7140
tctcagcccc tgcatggaaa gctgacccca gaggcagaac tattcccaga gagcttggcc   7200
aagaaaaaca aaactaccag cctggccagg ctcaggagta gtaagctgca gtgtctgttg   7260
tgttctagct tcaacagctg caggagttcc actctcaaat gctccacatt tctcacatcc   7320
tcctgattct ggtcactacc catcttcaaa gaacagaata tctcacatca gcatactgtg   7380
aaggactagt catgggtgca gctgctcaga gctgcaaagt cattctggat ggtggagagc   7440
ttacaaacat ttcatgatgc tccccccgct ctgatggctg gagcccaatc cctacacaga   7500
ctcctgctgt atgtgtttc ctttcactct gagccacagc cagagggcag gcattcagtc    7560
tcctcttcag gctggggctg gggcactgag aactcaccca acaccttgct ctcactcctt   7620
ctgcaaaaca agaaagagct ttgtgctgca gtagccatga agaatgaaag gaaggcttta   7680
actaaaaaat gtcagagatt attttcaacc ccttactgtg gatcaccagc aaggaggaaa   7740
cacaacacag agacattttt tcccctcaaa ttatcaaaag aatcactgca tttgttaaag   7800
agagcaactg aatcaggaag cagagttttg aacatatcag aagttaggaa tctgcatcag   7860
agacaaatgc agtcatggtt gtttgctgca taccagccct aatcattaga agcctcatgg   7920
acttcaaaca tcattccctc tgacaagatg ctctagccta actccatgag ataaaataaa   7980
tctgcctttc agagccaaag aagagtccac cagcttcttc tcagtgtgaa caagagctcc   8040
agtcaggtta gtcagtccag tgcagtagag gagaccagtc tgcatcctct aattttcaaa   8100
ggcaagaaga tttgtttacc ctggacacca ggcacaagtg aggtcacaga gctcttagat   8160
atgcagtcct catgagtgag gagactaaag cgcatgccat caagacttca gtgtagagaa   8220
aacctccaaa aaagcctcct cactacttct ggaatagctc agaggccgag gcggcctcgg   8280
cctctgcata aataaaaaaa attagtcagc catggggcgg agaatgggcg gaactgggcg   8340
gagttagggg cgggatgggc ggagttaggg gcgggactat ggttgctgac taattgagat   8400
gcatgctttg catacttctg cctgctgggg agcctgggga ctttccacac ctggttgctg   8460
actaattgag atgcatgctt tgcatacttc tgcctgctgg ggagcctggg gactttccac   8520
accctaactg acacacattc cacagctgca ttaatgaatc ggccaacgcg cggggagagg   8580
cggtttgcgt attgggcgct cttccgcttc ctcgctcact gactcgctgc gctcggtcgt   8640
tcggctgcgg cgagcggtat cagctcactc aaaggcggta atacggttat ccacagaatc   8700
aggggataac gcaggaaaga acatgtgagc aaaaggccag caaaaggcca ggaaccgtaa   8760
aaaggccgcg ttgctggcgt ttttccatag gctccgcccc cctgacgagc atcacaaaaa   8820
tcgacgctca agtcagaggt ggcgaaaccc gacaggacta taaagatacc aggcgtttcc   8880
ccctggaagc tccctcgtgc gctctcctgt tccgaccctg ccgcttaccg gatacctgtc   8940
cgcctttctc ccttcgggaa gcgtggcgct ttctcatagc tcacgctgta ggtatctcag   9000
ttcggtgtag gtcgttcgct ccaagctggg ctgtgtgcac gaaccccccg ttcagcccga   9060
ccgctgcgcc ttatccggta actatcgtct tgagtccaac ccggtaagac acgacttatc   9120
```

gccactggca gcagccactg gtaacaggat tagcagagcg aggtatgtag gcggtgctac 9180
agagttcttg aagtggtggc ctaactacgg ctacactaga agaacagtat ttggtatctg 9240
cgctctgctg aagccagtta ccttcggaaa aagagttggt agctcttgat ccggcaaaca 9300
aaccaccgct ggtagcggtg gtttttttgt ttgcaagcag cagattacgc gcagaaaaaa 9360
aggatctcaa gaagatcctt tgatcttttc tacggggtct gacgctcagt ggaacgaaaa 9420
ctcacgttaa gggattttgg tcatgagatt atcaaaaagg atcttcacct agatcctttt 9480
aaattaaaaa tgaagtttta aatcaatcta aagtatatat gagtaaactt ggtctgacag 9540
ttaccaatgc ttaatcagtg aggcacctat ctcagcgatc tgtctatttc gttcatccat 9600
agttgcctga ctcctgcaaa ccacgttgtg tctcaaaatc tctgatgtta cattgcacaa 9660
gataaaaata tatcatcatg aacaataaaa ctgtctgctt acataaacag taatacaagg 9720
ggtgttatga gccatattca acgggaaacg tcttgctcga ggccgcgatt aaattccaac 9780
atggatgctg atttatatgg gtataaatgg gctcgcgata atgtcgggca atcaggtgcg 9840
acaatctatc gattgtatgg gaagcccgat gcgccagagt tgtttctgaa acatggcaaa 9900
ggtagcgttg ccaatgatgt tacagatgag atggtcagac taaactggct gacggaattt 9960
atgcctcttc cgaccatcaa gcattttatc cgtactcctg atgatgcatg gttactcacc 10020
actgcgatcc ccgggaaaac agcattccag gtattagaag aatatcctga ttcaggtgaa 10080
aatattgttg atgcgctggc agtgttcctg cgccggttgc attcgattcc tgtttgtaat 10140
tgtcctttta acagcgatcg cgtatttcgt ctcgctcagg cgcaatcacg aatgaataac 10200
ggtttggttg atgcgagtga ttttgatgac gagcgtaatg gctggcctgt tgaacaagtc 10260
tggaaagaaa tgcataagct tttgccattc tcaccggatt cagtcgtcac tcatggtgat 10320
ttctcacttg ataaccttat ttttgacgag gggaaattaa taggttgtat tgatgttgga 10380
cgagtcggaa tcgcagaccg ataccaggat cttgccatcc tatggaactg cctcggtgag 10440
ttttctcctt cattacagaa acggcttttt caaaaatatg gtattgataa tcctgatatg 10500
aataaattgc agtttcattt gatgctcgat gagtttttct aagggcggcc tgccaccata 10560
cccacgccga aacaagcgct catgagcccg aagtggcgag cccgatcttc cccatcggtg 10620
atgtcggcga tataggcgcc agcaaccgca cctgtggcgc cggtgatgag ggcgcgccaa 10680
gtcgacgtcc ggcagtc 10697

<210> SEQ ID NO 2
<211> LENGTH: 11355
<212> TYPE: DNA
<213> ORGANISM: Artificial Sequence
<220> FEATURE:
<223> OTHER INFORMATION: Synthetic polynucleotide

<400> SEQUENCE: 2
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480

-continued

```
agtcactgac tgtctatgcc tgggaaaggg tgggcaggag atggggcagt gcaggaaaag    540
tggcactatg aaccctgcag ccctaggaat gcatctagac aattgtacta accttcttct    600
ctttcctctc ctgacagtcc ggaaagccac catgggccgc tgctgcttct acaccgccgg    660
caccctgagc ctgctgctgc tggtgaccag cgtgaccctg ctggtggccc gcgtgttcca    720
gaaggccgtg gaccagagca tcgagaagaa gatcgtgctg cgcaacggca ccgaggcctt    780
cgacagctgg gagaagcccc ccctgcccgt gtacacccag ttctacttct tcaacgtgac    840
caaccccgag gagatcctgc gcggcgagac cccccgcgtg gaggaggtgg gcccctacac    900
ctaccgcgag ctgcgcaaca aggccaacat ccagttcggc gacaacggca ccaccatcag    960
cgccgtgagc aacaaggcct acgtgttcga gcgcgaccag agcgtgggcg accccaagat   1020
cgacctgatc cgcaccctga acatccccgt gctgaccgtg atcgagtgga gccaggtgca   1080
cttcctgcgc gagatcatcg aggccatgct gaaggcctac cagcagaagc tgttcgtgac   1140
ccacaccgtg gacgagctgc tgtggggcta caaggacgag atcctgagcc tgatccacgt   1200
gttccgcccc gacatcagcc cctacttcgg cctgttctac gagaagaacg gcaccaacga   1260
cggcgactac gtgttcctga ccggcgagga cagctacctg aacttcacca agatcgtgga   1320
gtggaacggc aagaccagcc tggactggtg gatcaccgac aagtgcaaca tgatcaacgg   1380
caccgacggc gacagcttcc acccccctga tcaccaaggac gaggtgctgt acgtgttccc   1440
cagcgacttc tgccgcagcg tgtacatcac cttcagcgac tacgagagcg tgcagggcct   1500
gcccgccttc cgctacaagg tgcccgccga gatcctggcc aacaccagcg acaacgccgg   1560
cttctgcatc cccgagggca actgcctggg cagcggcgtg ctgaacgtga gcatctgcaa   1620
gaacggcgcc cccatcatca tgagcttccc ccacttctac caggccgacg agcgcttcgt   1680
gagcgccatc gagggcatgc accccaacca ggaggaccac gagaccttcg tggacatcaa   1740
cccccctgacc ggcatcatcc tgaaggccgc caagcgcttc cagatcaaca tctacgtgaa   1800
gaagctggac gacttcgtgg agaccggcga catccgcacc atggtgttcc ccgtgatgta   1860
cctgaacgag agcgtgcaca tcgacaagga gaccgccagc cgcctgaaga gcatgatcaa   1920
caccaccctg atcatcacca acatccccta catcatcatg gccctgggcg tgttcttcgg   1980
cctggtgttc acctggctgg cctgcaaggg ccagggcagc atggacgagg gcaccgccga   2040
cgagcgcgcc cccctgatcc gcacctgatt gtggccgaac cgccgaactc agaggccggc   2100
cccagaaaac ccgagcgagt agggggcggc gcgcaggagg gaggagaact gggggcgcgg   2160
gaggctggtg ggtgtggggg gtggagatgt agaagatgtg acgccgcggc ccggcgggtg   2220
ccagattagc ggacgcggtg cccgcggttg caacgggatc ccgggcgctg cagcttggga   2280
ggcggctctc cccaggcggc gtccgcggag acacccatcc gtgaacccca ggtcccgggc   2340
cgccggctcg ccgcgcacca ggggccggcg gacagaagag cggccgagcg gctcgaggct   2400
gggggaccgc gggcgcggcc gcgcgctgcc gggcgggagg ctgggggggcc ggggccgggg   2460
ccgtgccccg gagcgggtcg gaggccgggg ccggggccgg gggacggcgg ctccccgcgc   2520
ggctccagcg gctcggggat cccggccggg ccccgcaggg accatgatgg aattcagcag   2580
ccccagcaga gaggaatgcc ccaagcctct gagccgggtg tcaatcatgg ccggatctct   2640
gacaggactg ctgctgcttc aggccgtgtc ttgggcttct ggcgctagac cttgcatccc   2700
caagagcttc ggctacagca gcgtcgtgtg cgtgtgcaat gccacctact gcgacagctt   2760
cgaccctcct acctttcctg ctctgggcac cttcagcaga tacgagagca ccagatccgg   2820
```

-continued

```
cagacggatg gaactgagca tgggacccat ccaggccaat cacacaggca ctggcctgct   2880
gctgacactg cagcctgagc agaaattcca gaaagtgaaa ggcttcggcg gagccatgac   2940
agatgccgcc gctctgaata tcctggctct gtctccacca gctcagaacc tgctgctcaa   3000
gagctacttc agcgaggaag gcatcggcta caacatcatc agagtgccca tggccagctg   3060
cgacttcagc atcaggacct acacctacgc cgacacaccc gacgatttcc agctgcacaa   3120
cttcagcctg cctgaagagg acaccaagct gaagatccct ctgatccaca gagccctgca   3180
gctggcacaa agacccgtgt cactgctggc ctctccatgg acatctccca cctggctgaa   3240
aacaaatggc gccgtgaatg gcaagggcag cctgaaaggc caacctggcg acatctacca   3300
ccagacctgg gccagatact tcgtgaagtt cctggacgcc tatgccgagc acaagctgca   3360
gttttgggcc gtgacagccg agaacgaacc ttctgctgga ctgctgagcg gctacccctt   3420
tcagtgcctg ggctttacac ccgagcacca gcgggacttt atcgcccgtg atctgggacc   3480
cacactggcc aatagcaccc accataatgt gcggctgctg atgctggacg accagagact   3540
gcttctgccc cactgggcta aagtggtgct gacagatcct gaggccgcca aatacgtgca   3600
cggaatcgcc gtgcactggt atctggactt tctggcccct gccaaggcca cactgggaga   3660
gacacacaga ctgttcccca acaccatgct gttcgccagc gaagcctgtg tgggcagcaa   3720
gttttgggaa cagagcgtgc ggctcggcag ctgggataga ggcatgcagt acagccacag   3780
catcatcacc aacctgctgt accacgtcgt cggctggacc gactggaatc tggccctgaa   3840
tcctgaaggc ggccctaact gggtccgaaa cttcgtggac agccccatca tcgtggacat   3900
caccaaggac accttctaca agcagcccat gttctaccac ctgggacact tcagcaagtt   3960
catccccgag ggctctcagc gcgttggact ggtggcttcc cagaagaacg atctggacgc   4020
cgtggctctg atgcaccctg atggatctgc tgtggtggtg gtcctgaacc gcagcagcaa   4080
agatgtgccc ctgaccatca aggatcccgc cgtgggattc ctggaaacaa tcagccctgg   4140
ctactccatc cacacctacc tgtggcgtag acagtgacaa ttgttaatta agtttaaacc   4200
ctcgaggccg caagccgcat cgataccgtc gactagagct cgctgatcag cctcgactgt   4260
gccttctagt tgccagccat ctgttgtttg cccctccccc gtgccttcct tgaccctgga   4320
aggtgccact cccactgtcc tttcctaata aaatgaggaa attgcatcgc attgtctgag   4380
taggtgtcat tctattctgg ggggtggggt ggggcaggac agcaaggggg aggattggga   4440
agacaatagc aggcatgctg gggagagatc cacgataaca aacagctttt ttggggtgaa   4500
catattgact gaattccctg caggttggcc actccctctc tgcgcgctcg ctcgctcact   4560
gaggccgccc gggcaaagcc cgggcgtcgg gcgacctttg gtcgcccggc ctcagtgagc   4620
gagcgagcgc gcagagaggg agtggccaac tccatcacta ggggttcctg cggccgctcg   4680
tacggtctcg aggaattcct gcaggataac ttgccaacct cattctaaaa tgtatataga   4740
agcccaaaag acaataacaa aaatattctt gtagaacaaa atgggaaaga atgttccact   4800
aaatatcaag atttagagca aagcatgaga tgtgtgggga tagacagtga ggctgataaa   4860
atagagtaga gctcagaaac agacccattg atatatgtaa gtgacctatg aaaaaaatat   4920
ggcattttac aatgggaaaa tgatggtctt tttctttttt agaaaaacag ggaaatatat   4980
ttatatgtaa aaaataaaag ggaacccata tgtcatacca tacacacaaa aaaattccag   5040
tgaattataa gtctaaatgg agaaggcaaa actttaaatc ttttagaaaa taatatagaa   5100
gcatgcagac cagcctggcc aacatgatga aaccctctct actaataata aaatcagtag   5160
aactactcag gactactttg agtgggaagt ccttttctat gaagacttct ttggccaaaa   5220
```

```
ttaggctcta aatgcaagga gatagtgcat catgcctggc tgcacttact gataaatgat   5280
gttatcacca tctttaacca aatgcacagg aacaagttat ggtactgatg tgctggattg   5340
agaaggagct ctacttcctt gacaggacac atttgtatca acttaaaaaa gcagattttt   5400
gccagcagaa ctattcattc agaggtagga aacttagaat agatgatgtc actgattagc   5460
atggcttccc catctccaca gctgcttccc acccaggttg cccacagttg agtttgtcca   5520
gtgctcaggg ctgcccactc tcagtaagaa gccccacacc agcccctctc caaatatgtt   5580
ggctgttcct tccattaaag tgaccccact ttagagcagc aagtggattt ctgtttctta   5640
cagttcagga aggaggagtc agctgtgaga acctggagcc tgagatgctt ctaagtccca   5700
ctgctactgg ggtcagggaa gccagactcc agcatcagca gtcaggagca ctaagccctt   5760
gccaacatcc tgtttctcag agaaactgct tccattataa tggttgtcct tttttaagct   5820
atcaagccaa acaaccagtg tctaccatta ttctcatcac ctgaagccaa gggttctagc   5880
aaaagtcaag ctgtcttgta atggttgatg tgcctccagc ttctgtcttc agtcactcca   5940
ctcttagcct gctctgaatc aactctgacc acagttccct ggagcccctg ccacctgctg   6000
cccctgccac cttctccatc tgcagtgctg tgcagccttc tgcactcttg cagagctaat   6060
aggtggagac ttgaaggaag aggaggaaag tttctcataa tagccttgct gcaagctcaa   6120
atgggaggtg ggcactgtgc ccaggagcct tggagcaaag gctgtgccca acctctgact   6180
gcatccaggt ttggtcttga cagagataag aagccctggc ttttggagcc aaaatctagg   6240
tcagacttag gcaggattct caaagtttat cagcagaaca tgaggcagaa gaccctttct   6300
gctccagctt cttcaggctc aaccttcatc agaatagata gaaagagagg ctgtgagggt   6360
tcttaaaaca gaagcaaatc tgactcagag aataaacaac ctcctagtaa actacagctt   6420
agacagagca tctggtggtg agtgtgctca gtgtcctact caactgtctg gtatcagccc   6480
tcatgaggac ttctcttctt tccctcatag acctccatct ctgttttcct tagcctgcag   6540
aaatctggat ggctattcac agaatgcctg tgctttcaga gttgcatttt ttctctggta   6600
ttctggttca agcatttgaa ggtaggaaag gttctccaag tgcaagaaag ccagccctga   6660
gcctcaactg cctggctagt gtggtcagta ggatgcaaag gctgttgaat gccacaaggc   6720
caaactttaa cctgtgtacc acaagcctag cagcagaggc agctctgctc actggaactc   6780
tctgtcttct ttctcctgag ccttttcttt tcctgagttt tctagctctc ctcaacctta   6840
cctctgccct acccaggaca aacccaagag ccactgtttc tgtgatgtcc tctccagccc   6900
taattaggca tcatgacttc agcctgacct tccatgctca gaagcagtgc taatccactt   6960
cagatgagct gctctatgca acacaggcag agcctacaaa cctttgcacc agagccctcc   7020
acatatcagt gtttgttcat actcacttca acagcaaatg tgactgctga gattaagatt   7080
ttacacaaga tggtctgtaa tttcacagtt agttttatcc cattaggtat gaaagaatta   7140
gcataattcc ccttaaacat gaatgaatct tagatttttt aataaatagt tttggaagta   7200
aagacagaga catcaggagc acaaggaata gcctgagagg acaaacagaa caagaaagag   7260
tctggaaata cacaggatgt tcttggcctc ctcaaagcaa gtgcaagcag atagtaccag   7320
cagccccagg ctatcagagc ccagtgaaga gaagtaccat gaaagccaca gctctaacca   7380
ccctgttcca gagtgacaga cagtccccaa gacaagccag cctgagccag agagagaact   7440
gcaagagaaa gtttctaatt taggttctgt tagattcaga caagtgcagg tcatcctctc   7500
tccacagcta ctcacctctc cagcctaaca aagcctgcag tccacactcc aaccctggtg   7560
```

-continued

```
tctcacctcc tagcctctcc caacatcctg ctctctgacc atcttctgca tctctcatct   7620
caccatctcc cactgtctac agcctactct tgcaactacc atctcatttt ctgacatcct   7680
gtctacatct tctgccatac tctgccatct accataccac ctcttaccat ctaccacacc   7740
atcttttatc tccatccctc tcagaagcct ccaagctgaa tcctgcttta tgtgttcatc   7800
tcagcccctg catggaaagc tgaccccaga ggcagaacta ttcccagaga gcttggccaa   7860
gaaaaacaaa actaccagcc tggccaggct caggagtagt aagctgcagt gtctgttgtg   7920
ttctagcttc aacagctgca ggagttccac tctcaaatgc tccacatttc tcacatcctc   7980
ctgattctgg tcactaccca tcttcaaaga acagaatatc tcacatcagc atactgtgaa   8040
ggactagtca tgggtgcagc tgctcagagc tgcaaagtca ttctggatgg tggagagctt   8100
acaaacattt catgatgctc cccccgctct gatggctgga gcccaatccc tacacagact   8160
cctgctgtat gtgttttcct ttcactctga gccacagcca gagggcaggc attcagtctc   8220
ctcttcaggc tggggctggg gcactgagaa ctcacccaac accttgctct cactccttct   8280
gcaaaacaag aaagagcttt gtgctgcagt agccatgaag aatgaaagga aggctttaac   8340
taaaaaatgt cagagattat tttcaacccc ttactgtgga tcaccagcaa ggaggaaaca   8400
caacacagag acatttttc ccctcaaatt atcaaaagaa tcactgcatt tgttaaagag   8460
agcaactgaa tcaggaagca gagttttgaa catatcagaa gttaggaatc tgcatcagag   8520
acaaatgcag tcatggttgt ttgctgcata ccagccctaa tcattagaag cctcatggac   8580
ttcaaacatc attccctctg acaagatgct ctagcctaac tccatgagat aaaataaatc   8640
tgcctttcag agccaaagaa gagtccacca gcttcttctc agtgtgaaca agagctccag   8700
tcaggttagt cagtccagtg cagtagagga gaccagtctg catcctctaa ttttcaaagg   8760
caagaagatt tgtttaccct ggacaccagg cacaagtgag gtcacagagc tcttagatat   8820
gcagtcctca tgagtgagga gactaaagcg catgccatca agacttcagt gtagagaaaa   8880
cctccaaaaa agcctcctca ctacttctgg aatagctcag aggccgaggc ggcctcggcc   8940
tctgcataaa taaaaaaaat tagtcagcca tggggcggag aatgggcgga actgggcgga   9000
gttaggggcg ggatgggcgg agttaggggc gggactatgg ttgctgacta attgagatgc   9060
atgctttgca tacttctgcc tgctggggag cctggggact ttccacacct ggttgctgac   9120
taattgagat gcatgctttg catacttctg cctgctgggg agcctgggga ctttccacac   9180
cctaactgac acacattcca cagctgcatt aatgaatcgg ccaacgcgcg gggagaggcg   9240
gtttgcgtat tgggcgctct tccgcttcct cgctcactga ctcgctgcgc tcggtcgttc   9300
ggctgcggcg agcggtatca gctcactcaa aggcggtaat acggttatcc acagaatcag   9360
gggataacgc aggaaagaac atgtgagcaa aaggccagca aaaggccagg aaccgtaaaa   9420
aggccgcgtt gctggcgttt ttccataggc tccgcccccc tgacgagcat cacaaaaatc   9480
gacgctcaag tcagaggtgg cgaaacccga caggactata aagataccag gcgtttcccc   9540
ctggaagctc cctcgtgcgc tctcctgttc cgaccctgcc gcttaccgga tacctgtccg   9600
cctttctccc ttcgggaagc gtggcgcttt ctcatagctc acgctgtagg tatctcagtt   9660
cggtgtaggt cgttcgctcc aagctgggct gtgtgcacga accccccgtt cagcccgacc   9720
gctgcgcctt atccggtaac tatcgtcttg agtccaaccc ggtaagacac gacttatcgc   9780
cactggcagc agccactggt aacaggatta gcagagcgag gtatgtaggc ggtgctacag   9840
agttcttgaa gtggtggcct aactacggct acactagaag aacagtattt ggtatctgcg   9900
ctctgctgaa gccagttacc ttcggaaaaa gagttggtag ctcttgatcc ggcaaacaaa   9960
```

ccaccgctgg tagcggtggt ttttttgttt gcaagcagca gattacgcgc agaaaaaaag 10020
gatctcaaga agatcctttg atcttttcta cggggtctga cgctcagtgg aacgaaaact 10080
cacgttaagg gattttggtc atgagattat caaaaaggat cttcacctag atccttttaa 10140
attaaaaatg aagttttaaa tcaatctaaa gtatatatga gtaaacttgg tctgacagtt 10200
accaatgctt aatcagtgag gcacctatct cagcgatctg tctatttcgt tcatccatag 10260
ttgcctgact cctgcaaacc acgttgtgtc tcaaaatctc tgatgttaca ttgcacaaga 10320
taaaaatata tcatcatgaa caataaaact gtctgcttac ataaacagta atacaagggg 10380
tgttatgagc catattcaac gggaaacgtc ttgctcgagg ccgcgattaa attccaacat 10440
ggatgctgat ttatatgggt ataaatgggc tcgcgataat gtcgggcaat caggtgcgac 10500
aatctatcga ttgtatggga agcccgatgc gccagagttg tttctgaaac atggcaaagg 10560
tagcgttgcc aatgatgtta cagatgagat ggtcagacta aactggctga cggaatttat 10620
gcctcttccg accatcaagc attttatccg tactcctgat gatgcatggt tactcaccac 10680
tgcgatcccc gggaaaacag cattccaggt attagaagaa tatcctgatt caggtgaaaa 10740
tattgttgat gcgctggcag tgttcctgcg ccggttgcat tcgattcctg tttgtaattg 10800
tccttttaac agcgatcgcg tatttcgtct cgctcaggcg caatcacgaa tgaataacgg 10860
tttggttgat gcgagtgatt ttgatgacga gcgtaatggc tggcctgttg aacaagtctg 10920
gaaagaaatg cataagcttt tgccattctc accggattca gtcgtcactc atggtgattt 10980
ctcacttgat aaccttattt ttgacgaggg gaaattaata ggttgtattg atgttggacg 11040
agtcggaatc gcagaccgat accaggatct tgccatccta tggaactgcc tcggtgagtt 11100
ttctccttca ttacagaaac ggctttttca aaaatatggt attgataatc ctgatatgaa 11160
taaattgcag tttcatttga tgctcgatga gtttttctaa gggcggcctg ccaccatacc 11220
cacgccgaaa caagcgctca tgagcccgaa gtggcgagcc cgatcttccc catcggtgat 11280
gtcggcgata taggcgccag caaccgcacc tgtggcgccg gtgatgaggg cgcgccaagt 11340
cgacgtccgg cagtc 11355

<210> SEQ ID NO 3
<211> LENGTH: 11420
<212> TYPE: DNA
<213> ORGANISM: Artificial Sequence
<220> FEATURE:
<223> OTHER INFORMATION: Synthetic polynucleotide

<400> SEQUENCE: 3
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctgcag ccctaggaat gcatctagac aattgtacta accttcttct 600

-continued

```
ctttcctctc ctgacagtcc ggaaagccac catggaattc agcagcccca gcagagagga    660
atgccccaag cctctgagcc gggtgtcaat catggccgga tctctgacag gactgctgct    720
gcttcaggcc gtgtcttggg cttctggcgc tagaccttgc atccccaaga gcttcggcta    780
cagcagcgtc gtgtgcgtgt gcaatgccac ctactgcgac agcttcgacc ctcctacctt    840
tcctgctctg ggcaccttca gcagatacga gagcaccaga tccggcagac ggatggaact    900
gagcatggga cccatccagg ccaatcacac aggcactggc ctgctgctga cactgcagcc    960
tgagcagaaa ttccagaaag tgaaaggctt cggcggagcc atgacagatg ccgccgctct   1020
gaatatcctg gctctgtctc caccagctca gaacctgctg ctcaagagct acttcagcga   1080
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga aacaatcagc cctggctact ccatccacac   2220
ctacctgtgg cgtagacagt gacaattgtt aattaagttt catcgatacc gtcgactaga   2280
gctcgctgat cagcctcgac tgtgccttct agttgccagc catctgttgt ttgcccctcc   2340
cccgtgcctt ccttgaccct ggaaggtgcc actcccactg tcctttccta ataaaatgag   2400
gaaattgcat cgcattgtct gagtaggtgt cattctattc tggggggtgg ggtggggcag   2460
gacagcaagg gggaggattg ggaagacaat agcaggcatg ctggggagag atccacgata   2520
acaaacagct tttttggggg ggcggagtta gggcggagcc aatcagcgtg cgccgttccg   2580
aaagttgcct tttatggctg ggcggagaat gggcggtgaa cgccgatgat tatataagga   2640
cgcgccgggt gtggcacagc tagttccgtc gcagccggga tttgggtcgc ggttcttgtt   2700
tgtggatccc tgtgatcgtc acttggtaag tcactgactg tctatgcctg ggaaagggtg   2760
ggcaggagat ggggcagtgc aggaaaagtg gcactatgaa ccctgcagcc ctaggaatgc   2820
atctagacaa ttgtactaac cttcttctct ttcctctcct gacagtccgg aaagccacca   2880
tgggccgctg ctgcttctac accgccggca ccctgagcct gctgctgctg gtgaccagcg   2940
tgaccctgct ggtggcccgc gtgttccaga aggccgtgga ccagagcatc gagaagaaga   3000
```

```
tcgtgctgcg caacggcacc gaggccttcg acagctggga gaagcccccc ctgcccgtgt   3060
acacccagtt ctacttcttc aacgtgacca accccgagga gatcctgcgc ggcgagaccc   3120
cccgcgtgga ggaggtgggc ccctacacct accgcgagct gcgcaacaag gccaacatcc   3180
agttcggcga caacggcacc accatcagcg ccgtgagcaa caaggcctac gtgttcgagc   3240
gcgaccagag cgtgggcgac cccaagatcg acctgatccg caccctgaac atccccgtgc   3300
tgaccgtgat cgagtggagc caggtgcact tcctgcgcga gatcatcgag gccatgctga   3360
aggcctacca gcagaagctg ttcgtgaccc acaccgtgga cgagctgctg tggggctaca   3420
aggacgagat cctgagcctg atccacgtgt tccgccccga catcagcccc tacttcggcc   3480
tgttctacga gaagaacggc accaacgacg gcgactacgt gttcctgacc ggcgaggaca   3540
gctacctgaa cttcaccaag atcgtggagt ggaacggcaa gaccagcctg gactggtgga   3600
tcaccgacaa gtgcaacatg atcaacggca ccgacggcga cagcttccac cccctgatca   3660
ccaaggacga ggtgctgtac gtgttcccca gcgacttctg ccgcagcgtg tacatcacct   3720
tcagcgacta cgagagcgtg cagggcctgc ccgccttccg ctacaaggtg cccgccgaga   3780
tcctggccaa caccagcgac aacgccggct tctgcatccc cgagggcaac tgcctgggca   3840
gcggcgtgct gaacgtgagc atctgcaaga acggcgcccc catcatcatg agcttccccc   3900
acttctacca ggccgacgag cgcttcgtga gcgccatcga gggcatgcac cccaaccagg   3960
aggaccacga gaccttcgtg gacatcaacc ccctgaccgg catcatcctg aaggccgcca   4020
agcgcttcca gatcaacatc tacgtgaaga agctggacga cttcgtggag accggcgaca   4080
tccgcaccat ggtgttcccc gtgatgtacc tgaacgagag cgtgcacatc gacaaggaga   4140
ccgccagccg cctgaagagc atgatcaaca ccaccctgat catcaccaac atcccctaca   4200
tcatcatggc cctgggcgtg ttcttcggcc tggtgttcac ctggctggcc tgcaagggcc   4260
agggcagcat ggacgagggc accgccgacg agcgcgcccc cctgatccgc acctgaccca   4320
ggggactcaa tcagcctcga agacatgata agatacattg atgagtttgg acaaaccaca   4380
acaagaatgc agtgaaaaaa atgctttatt tgtgaaattt gtgatgctat tgctttattt   4440
gtaaccatta taagctgcaa taaacaagtt aacaacaaca attgcattca ttttatgttt   4500
caggttcagg gggagatgtg ggaggttttt taaagcaagt aaaacctcta caaatgtggt   4560
atgaacatat tgactgaatt ccctgcaggt tggccactcc ctctctgcgc gctcgctcgc   4620
tcactgaggc cgcccgggca aagcccgggc gtcgggcgac ctttggtcgc ccggcctcag   4680
tgagcgagcg agcgcgcaga gagggagtgg ccaactccat cactaggggt tcctgcggcc   4740
gctcgtacgg tctcgaggaa ttcctgcagg ataacttgcc aacctcattc taaaatgtat   4800
atagaagccc aaaagacaat aacaaaaata ttcttgtaga acaaaatggg aaagaatgtt   4860
ccactaaata tcaagattta gagcaaagca tgagatgtgt ggggatagac agtgaggctg   4920
ataaaataga gtagagctca gaaacagacc cattgatata tgtaagtgac ctatgaaaaa   4980
aatatggcat tttacaatgg gaaaatgatg gtctttttct tttttagaaa aacagggaaa   5040
tatatttata tgtaaaaaat aaaagggaac ccatatgtca taccatacac acaaaaaaat   5100
tccagtgaat tataagtcta aatggagaag gcaaaacttt aaatctttta gaaaataata   5160
tagaagcatg cagaccagcc tggccaacat gatgaaaccc tctctactaa taataaaatc   5220
agtagaacta ctcaggacta ctttgagtgg gaagtccttt tctatgaaga cttctttggc   5280
caaaattagg ctctaaatgc aaggagatag tgcatcatgc ctggctgcac ttactgataa   5340
```

-continued

```
atgatgttat caccatcttt aaccaaatgc acaggaacaa gttatggtac tgatgtgctg   5400
gattgagaag gagctctact tccttgacag gacacatttg tatcaactta aaaaagcaga   5460
tttttgccag cagaactatt cattcagagg taggaaactt agaatagatg atgtcactga   5520
ttagcatggc ttccccatct ccacagctgc ttcccaccca ggttgcccac agttgagttt   5580
gtccagtgct cagggctgcc cactctcagt aagaagcccc acaccagccc ctctccaaat   5640
atgttggctg ttccttccat taaagtgacc ccactttaga gcagcaagtg gatttctgtt   5700
tcttacagtt caggaaggag gagtcagctg tgagaacctg gagcctgaga tgcttctaag   5760
tcccactgct actggggtca gggaagccag actccagcat cagcagtcag gagcactaag   5820
cccttgccaa catcctgttt ctcagagaaa ctgcttccat tataatggtt gtcctttttt   5880
aagctatcaa gccaaacaac cagtgtctac cattattctc atcacctgaa gccaagggtt   5940
ctagcaaaag tcaagctgtc ttgtaatggt tgatgtgcct ccagcttctg tcttcagtca   6000
ctccactctt agcctgctct gaatcaactc tgaccacagt tccctggagc cctgccacc    6060
tgctgcccct gccaccttct ccatctgcag tgctgtgcag ccttctgcac tcttgcagag   6120
ctaataggtg gagacttgaa ggaagaggag gaaagtttct cataatagcc ttgctgcaag   6180
ctcaaatggg aggtgggcac tgtgcccagg agccttggag caaaggctgt gcccaacctc   6240
tgactgcatc caggtttggt cttgacagag ataagaagcc ctggcttttg gagccaaaat   6300
ctaggtcaga cttaggcagg attctcaaag tttatcagca gaacatgagg cagaagaccc   6360
tttctgctcc agcttcttca ggctcaacct tcatcagaat agatagaaag agaggctgtg   6420
agggttctta aaacagaagc aaatctgact cagagaataa acaacctcct agtaaactac   6480
agcttagaca gagcatctgg tggtgagtgt gctcagtgtc ctactcaact gtctggtatc   6540
agccctcatg aggacttctc ttctttccct catagacctc catctctgtt ttccttagcc   6600
tgcagaaatc tggatggcta ttcacagaat gcctgtgctt tcagagttgc atttttttctc  6660
tggtattctg gttcaagcat ttgaaggtag gaaaggttct ccaagtgcaa gaaagccagc   6720
cctgagcctc aactgcctgg ctagtgtggt cagtaggatg caaaggctgt tgaatgccac   6780
aaggccaaac tttaacctgt gtaccacaag cctagcagca gaggcagctc tgctcactgg   6840
aactctctgt cttctttctc ctgagccttt tcttttcctg agttttctag ctctcctcaa   6900
ccttacctct gccctaccca ggacaaaccc aagagccact gtttctgtga tgtcctctcc   6960
agccctaatt aggcatcatg acttcagcct gaccttccat gctcagaagc agtgctaatc   7020
cacttcagat gagctgctct atgcaacaca ggcagagcct acaaaccttt gcaccagagc   7080
cctccacata tcagtgtttg ttcatactca cttcaacagc aaatgtgact gctgagatta   7140
agatttaca caagatggtc tgtaatttca cagttagttt tatcccatta ggtatgaaag    7200
aattagcata attcccctta aacatgaatg aatcttagat tttttaataa atagttttgg   7260
aagtaaagac agagacatca ggagcacaag gaatagcctg agaggacaaa cagaacaaga   7320
aagagtctgg aaatacacag gatgttcttg gcctcctcaa agcaagtgca agcagatagt   7380
accagcagcc ccaggctatc agagcccagt gaagagaagt accatgaaag ccacagctct   7440
aaccaccctg ttccagagtg acagacagtc cccaagacaa gccagcctga gccagagaga   7500
gaactgcaag agaaagtttc taatttaggt tctgttagat tcagacaagt gcaggtcatc   7560
ctctctccac agctactcac ctctccagcc taacaaagcc tgcagtccac actccaaccc   7620
tggtgtctca cctcctagcc tctcccaaca tcctgctctc tgaccatctt ctgcatctct   7680
catctcacca tctcccactg tctacagcct actcttgcaa ctaccatctc attttctgac   7740
```

```
atcctgtcta catcttctgc catactctgc catctaccat accacctctt accatctacc   7800
acaccatctt ttatctccat ccctctcaga agcctccaag ctgaatcctg ctttatgtgt   7860
tcatctcagc ccctgcatgg aaagctgacc ccagaggcag aactattccc agagagcttg   7920
gccaagaaaa acaaaactac cagcctggcc aggctcagga gtagtaagct gcagtgtctg   7980
ttgtgttcta gcttcaacag ctgcaggagt tccactctca aatgctccac atttctcaca   8040
tcctcctgat tctggtcact acccatcttc aaagaacaga atatctcaca tcagcatact   8100
gtgaaggact agtcatgggt gcagctgctc agagctgcaa agtcattctg gatggtggag   8160
agcttacaaa catttcatga tgctccccc gctctgatgg ctggagccca atccctacac   8220
agactcctgc tgtatgtgtt ttcctttcac tctgagccac agccagaggg caggcattca   8280
gtctcctctt caggctgggg ctggggcact gagaactcac ccaacacctt gctctcactc   8340
cttctgcaaa acaagaaaga gctttgtgct gcagtagcca tgaagaatga aaggaaggct   8400
ttaactaaaa aatgtcagag attattttca accccttact gtggatcacc agcaaggagg   8460
aaacacaaca cagagacatt ttttcccctc aaattatcaa aagaatcact gcatttgtta   8520
aagagagcaa ctgaatcagg aagcagagtt ttgaacatat cagaagttag gaatctgcat   8580
cagagacaaa tgcagtcatg gttgtttgct gcataccagc cctaatcatt agaagcctca   8640
tggacttcaa acatcattcc ctctgacaag atgctctagc ctaactccat gagataaaat   8700
aaatctgcct ttcagagcca aagaagagtc caccagcttc ttctcagtgt gaacaagagc   8760
tccagtcagg ttagtcagtc cagtgcagta gaggagacca gtctgcatcc tctaattttc   8820
aaaggcaaga agatttgttt accctggaca ccaggcacaa gtgaggtcac agagctctta   8880
gatatgcagt cctcatgagt gaggagacta aagcgcatgc catcaagact tcagtgtaga   8940
gaaaacctcc aaaaaagcct cctcactact tctggaatag ctcagaggcc gaggcggcct   9000
cggcctctgc ataaataaaa aaaattagtc agccatgggg cggagaatgg gcggaactgg   9060
gcggagttag gggcgggatg ggcggagtta ggggcgggac tatggttgct gactaattga   9120
gatgcatgct ttgcatactt ctgcctgctg gggagcctgg ggactttcca cacctggttg   9180
ctgactaatt gagatgcatg ctttgcatac ttctgcctgc tggggagcct ggggactttc   9240
cacaccctaa ctgacacaca ttccacagct gcattaatga atcggccaac gcgcggggag   9300
aggcggtttg cgtattgggc gctcttccgc ttcctcgctc actgactcgc tgcgctcggt   9360
cgttcggctg cggcgagcgg tatcagctca ctcaaaggcg gtaatacggt tatccacaga   9420
atcaggggat aacgcaggaa agaacatgtg agcaaaaggc cagcaaaagg ccaggaaccg   9480
taaaaaggcc gcgttgctgg cgtttttcca taggctccgc ccccctgacg agcatcacaa   9540
aaatcgacgc tcaagtcaga ggtggcgaaa cccgacagga ctataaagat accaggcgtt   9600
tccccctgga agctccctcg tgcgctctcc tgttccgacc ctgccgctta ccggatacct   9660
gtccgccttt ctcccttcgg gaagcgtggc gctttctcat agctcacgct gtaggtatct   9720
cagttcggtg taggtcgttc gctccaagct gggctgtgtg cacgaacccc ccgttcagcc   9780
cgaccgctgc gccttatccg gtaactatcg tcttgagtcc aacccggtaa gacacgactt   9840
atcgccactg gcagcagcca ctggtaacag gattagcaga gcgaggtatg taggcggtgc   9900
tacagagttc ttgaagtggt ggcctaacta cggctacact agaagaacag tatttggtat   9960
ctgcgctctg ctgaagccag ttaccttcgg aaaaagagtt ggtagctctt gatccggcaa  10020
acaaaccacc gctggtagcg gtggtttttt tgtttgcaag cagcagatta cgcgcagaaa  10080
```

aaaaggatct caagaagatc ctttgatctt ttctacgggg tctgacgctc agtggaacga 10140
aaactcacgt taagggattt tggtcatgag attatcaaaa aggatcttca cctagatcct 10200
tttaaattaa aaatgaagtt ttaaatcaat ctaaagtata tatgagtaaa cttggtctga 10260
cagttaccaa tgcttaatca gtgaggcacc tatctcagcg atctgtctat ttcgttcatc 10320
catagttgcc tgactcctgc aaaccacgtt gtgtctcaaa atctctgatg ttacattgca 10380
caagataaaa atatatcatc atgaacaata aaactgtctg cttacataaa cagtaataca 10440
aggggtgtta tgagccatat tcaacgggaa acgtcttgct cgaggccgcg attaaattcc 10500
aacatggatg ctgatttata tgggtataaa tgggctcgcg ataatgtcgg gcaatcaggt 10560
gcgacaatct atcgattgta tgggaagccc gatgcgccag agttgtttct gaaacatggc 10620
aaaggtagcg ttgccaatga tgttacagat gagatggtca gactaaactg gctgacggaa 10680
tttatgcctc ttccgaccat caagcatttt atccgtactc ctgatgatgc atggttactc 10740
accactgcga tccccgggaa aacagcattc caggtattag aagaatatcc tgattcaggt 10800
gaaaatattg ttgatgcgct ggcagtgttc ctgcgccggt tgcattcgat tcctgtttgt 10860
aattgtcctt ttaacagcga tcgcgtattt cgtctcgctc aggcgcaatc acgaatgaat 10920
aacggtttgg ttgatgcgag tgattttgat gacgagcgta atggctggcc tgttgaacaa 10980
gtctggaaag aaatgcataa gcttttgcca ttctcaccgg attcagtcgt cactcatggt 11040
gatttctcac ttgataacct tatttttgac gaggggaaat taataggttg tattgatgtt 11100
ggacgagtcg gaatcgcaga ccgataccag gatcttgcca tcctatggaa ctgcctcggt 11160
gagttttctc cttcattaca gaaacggctt tttcaaaaat atggtattga taatcctgat 11220
atgaataaat tgcagtttca tttgatgctc gatgagtttt tctaagggcg gcctgccacc 11280
atacccacgc cgaaacaagc gctcatgagc ccgaagtggc gagcccgatc ttccccatcg 11340
gtgatgtcgg cgatataggc gccagcaacc gcacctgtgg cgccggtgat gagggcgcgc 11400
caagtcgacg tccggcagtc 11420

<210> SEQ ID NO 4
<211> LENGTH: 11171
<212> TYPE: DNA
<213> ORGANISM: Artificial Sequence
<220> FEATURE:
<223> OTHER INFORMATION: Synthetic polynucleotide

<400> SEQUENCE: 4
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctcctg gtggcgaggg gagggggtg gtcctcgaac gccttgcaga 600
actggcctgg atacagagtg gaccggctgg ccccatctgg aagacttcga gatacactgt 660
tgtcttactg cgctcaacag tgtatctcga agtcttccaa atggtgccag ccatcgcagc 720

```
ggggtgcagg aaatgggggc agccccccctt tttggctatc cttccacgtg ttcttttttg    780
tatcttttgt gtttcctaga aaacatctca gtcaccaccg cagccctagg aatgcatcta    840
gacaattgta ctaaccttct tctctttcct ctcctgacag tccggaaagc caccatgggc    900
cgctgctgct tctacaccgc cggcaccctg agcctgctgc tgctggtgac cagcgtgacc    960
ctgctggtgg cccgcgtgtt ccagaaggcc gtggaccaga gcatcgagaa gaagatcgtg   1020
ctgcgcaacg gcaccgaggc cttcgacagc tgggagaagc ccccccctgcc cgtgtacacc   1080
cagttctact tcttcaacgt gaccaacccc gaggagatcc tgcgcggcga gacccccccgc   1140
gtggaggagg tgggccccta cacctaccgc gagctgcgca acaaggccaa catccagttc   1200
ggcgacaacg gcaccaccat cagcgccgtg agcaacaagg cctacgtgtt cgagcgcgac   1260
cagagcgtgg gcgaccccaa gatcgacctg atccgcaccc tgaacatccc cgtgctgacc   1320
gtgatcgagt ggagccaggt gcacttcctg cgcgagatca tcgaggccat gctgaaggcc   1380
taccagcaga agctgttcgt gacccacacc gtggacgagc tgctgtgggg ctacaaggac   1440
gagatcctga gcctgatcca cgtgttccgc cccgacatca gcccctactt cggcctgttc   1500
tacgagaaga acggcaccaa cgacggcgac tacgtgttcc tgaccggcga ggacagctac   1560
ctgaacttca ccaagatcgt ggagtggaac ggcaagacca gcctggactg gtggatcacc   1620
gacaagtgca acatgatcaa cggcaccgac ggcgacagct tccacccccct gatcaccaag   1680
gacgaggtgc tgtacgtgtt ccccagcgac ttctgccgca gcgtgtacat caccttcagc   1740
gactacgaga gcgtgcaggg cctgcccgcc ttccgctaca aggtgcccgc cgagatcctg   1800
gccaacacca gcgacaacgc cggcttctgc atccccgagg gcaactgcct gggcagcggc   1860
gtgctgaacg tgagcatctg caagaacggc gcccccatca tcatgagctt cccccacttc   1920
taccaggccg acgagcgctt cgtgagcgcc atcgagggca tgcaccccaa ccaggaggac   1980
cacgagacct tcgtggacat caacccccctg accggcatca tcctgaaggc cgccaagcgc   2040
ttccagatca acatctacgt gaagaagctg gacgacttcg tggagaccgg cgacatccgc   2100
accatggtgt tccccgtgat gtacctgaac gagagcgtgc acatcgacaa ggagaccgcc   2160
agccgcctga agagcatgat caacaccacc ctgatcatca ccaacatccc ctacatcatc   2220
atggccctgg gcgtgttctt cggcctggtg ttcacctggc tggcctgcaa gggccagggc   2280
agcatggacg agggcaccgc cgacgagcgc gcccccctga tccgcaccga gggcagagga   2340
agtcttctga catgcggaga cgtggaagag aatcccggcc ctatggaatt cagcagcccc   2400
agcagagagg aatgccccaa gcctctgagc cgggtgtcaa tcatggccgg atctctgaca   2460
ggactgctgc tgcttcaggc cgtgtcttgg gcttctggcg ctagaccttg catccccaag   2520
agcttcggct acagcagcgt cgtgtgcgtg tgcaatgcca cctactgcga cagcttcgac   2580
cctcctacct ttcctgctct gggcaccttc agcagatacg agagcaccag atccggcaga   2640
cggatggaac tgagcatggg acccatccag gccaatcaca caggcactgg cctgctgctg   2700
acactgcagc ctgagcagaa attccagaaa gtgaaaggct tcggcggagc catgacagat   2760
gccgccgctc tgaatatcct ggctctgtct ccaccagctc agaacctgct gctcaagagc   2820
tacttcagcg aggaaggcat cggctacaac atcatcagag tgcccatggc cagctgcgac   2880
ttcagcatca ggacctacac ctacgccgac acacccgacg atttccagct gcacaacttc   2940
agcctgcctg aagaggacac caagctgaag atccctctga tccacagagc cctgcagctg   3000
gcacaaagac ccgtgtcact gctggcctct ccatggacat ctcccacctg gctgaaaaca   3060
```

-continued

```
aatggcgccg tgaatggcaa gggcagcctg aaaggccaac ctggcgacat ctaccaccag   3120
acctgggcca gatacttcgt gaagttcctg gacgcctatg ccgagcacaa gctgcagttt   3180
tgggccgtga cagccgagaa cgaaccttct gctggactgc tgagcggcta ccccttttcag   3240
tgcctgggct ttacacccga gcaccagcgg gactttatcg cccgtgatct gggacccaca   3300
ctggccaata gcacccacca taatgtgcgg ctgctgatgc tggacgacca gagactgctt   3360
ctgccccact gggctaaagt ggtgctgaca gatcctgagg ccgccaaata cgtgcacgga   3420
atcgccgtgc actggtatct ggactttctg gcccctgcca aggccacact gggagagaca   3480
cacagactgt tccccaacac catgctgttc gccagcgaag cctgtgtggg cagcaagttt   3540
tgggaacaga gcgtgcggct cggcagctgg gatagaggca tgcagtacag ccacagcatc   3600
atcaccaacc tgctgtacca cgtcgtcggc tggaccgact ggaatctggc cctgaatcct   3660
gaaggcggcc ctaactgggt ccgaaacttc gtggacagcc ccatcatcgt ggacatcacc   3720
aaggacacct tctacaagca gcccatgttc taccacctgg gacacttcag caagttcatc   3780
cccgagggct ctcagcgcgt tggactggtg gcttcccaga agaacgatct ggacgccgtg   3840
gctctgatgc accctgatgg atctgctgtg gtggtggtcc tgaaccgcag cagcaaagat   3900
gtgcccctga ccatcaagga tcccgccgtg ggattcctgg aaacaatcag ccctggctac   3960
tccatccaca cctacctgtg gcgtagacag tgacaattgt taattaagtt taaaccctcg   4020
aggccgcaag ccgcatcgat accgtcgact agagctcgct gatcagcctc gactgtgcct   4080
tctagttgcc agccatctgt tgtttgcccc tcccccgtgc cttccttgac cctggaaggt   4140
gccactccca ctgtcctttc ctaataaaat gaggaaattg catcgcattg tctgagtagg   4200
tgtcattcta ttctgggggg tggggtgggg caggacagca agggggagga ttgggaagac   4260
aatagcaggc atgctgggga gagatccacg ataacaaaca gctttttgg ggtgaacata   4320
ttgactgaat tccctgcagg ttggccactc cctctctgcg cgctcgctcg ctcactgagg   4380
ccgcccgggc aaagcccggg cgtcgggcga cctttggtcg cccggcctca gtgagcgagc   4440
gagcgcgcag agagggagtg gccaactcca tcactagggg ttcctgcggc cgctcgtacg   4500
gtctcgagga attcctgcag gataacttgc caacctcatt ctaaaatgta tatagaagcc   4560
caaaagacaa taacaaaaat attcttgtag aacaaaatgg gaaagaatgt tccactaaat   4620
atcaagattt agagcaaagc atgagatgtg tggggataga cagtgaggct gataaaatag   4680
agtagagctc agaaacagac ccattgatat atgtaagtga cctatgaaaa aaatatggca   4740
ttttacaatg ggaaaatgat ggtctttttc tttttagaa aaacagggaa atatatttat   4800
atgtaaaaaa taaaagggaa cccatatgtc ataccataca cacaaaaaaa ttccagtgaa   4860
ttataagtct aaatggagaa ggcaaaactt taaatctttt agaaaataat atagaagcat   4920
gcagaccagc ctggccaaca tgatgaaacc ctctctacta ataataaaat cagtagaact   4980
actcaggact actttgagtg ggaagtcctt ttctatgaag acttctttgg ccaaaattag   5040
gctctaaatg caaggagata gtgcatcatg cctggctgca cttactgata aatgatgtta   5100
tcaccatctt taaccaaatg cacaggaaca agttatggta ctgatgtgct ggattgagaa   5160
ggagctctac ttccttgaca ggacacattt gtatcaactt aaaaaagcag atttttgcca   5220
gcagaactat tcattcagag gtaggaaact tagaatagat gatgtcactg attagcatgg   5280
cttccccatc tccacagctg cttcccaccc aggttgccca cagttgagtt tgtccagtgc   5340
tcagggctgc ccactctcag taagaagccc cacaccagcc cctctccaaa tatgttggct   5400
gttccttcca ttaaagtgac cccactttag agcagcaagt ggatttctgt ttcttacagt   5460
```

-continued

```
tcaggaagga ggagtcagct gtgagaacct ggagcctgag atgcttctaa gtcccactgc   5520
tactggggtc agggaagcca gactccagca tcagcagtca ggagcactaa gcccttgcca   5580
acatcctgtt tctcagagaa actgcttcca ttataatggt tgtccttttt taagctatca   5640
agccaaacaa ccagtgtcta ccattattct catcacctga agccaagggt tctagcaaaa   5700
gtcaagctgt cttgtaatgg ttgatgtgcc tccagcttct gtcttcagtc actccactct   5760
tagcctgctc tgaatcaact ctgaccacag ttccctggag cccctgccac ctgctgcccc   5820
tgccaccttc tccatctgca gtgctgtgca gccttctgca ctcttgcaga gctaataggt   5880
ggagacttga aggaagagga ggaaagtttc tcataatagc cttgctgcaa gctcaaatgg   5940
gaggtgggca ctgtgcccag gagccttgga gcaaaggctg tgcccaacct ctgactgcat   6000
ccaggtttgg tcttgacaga gataagaagc cctggctttt ggagccaaaa tctaggtcag   6060
acttaggcag gattctcaaa gtttatcagc agaacatgag gcagaagacc ctttctgctc   6120
cagcttcttc aggctcaacc ttcatcagaa tagatagaaa gagaggctgt gagggttctt   6180
aaaacagaag caaatctgac tcagagaata aacaacctcc tagtaaacta cagcttagac   6240
agagcatctg gtggtgagtg tgctcagtgt cctactcaac tgtctggtat cagccctcat   6300
gaggacttct cttctttccc tcatagacct ccatctctgt tttccttagc ctgcagaaat   6360
ctggatggct attcacagaa tgcctgtgct ttcagagttg catttttttct ctggtattct   6420
ggttcaagca tttgaaggta ggaaaggttc tccaagtgca agaaagccag ccctgagcct   6480
caactgcctg gctagtgtgg tcagtaggat gcaaaggctg ttgaatgcca caaggccaaa   6540
ctttaacctg tgtaccacaa gcctagcagc agaggcagct ctgctcactg gaactctctg   6600
tcttctttct cctgagcctt ttcttttcct gagttttcta gctctcctca accttacctc   6660
tgccctaccc aggacaaacc caagagccac tgtttctgtg atgtcctctc cagccctaat   6720
taggcatcat gacttcagcc tgaccttcca tgctcagaag cagtgctaat ccacttcaga   6780
tgagctgctc tatgcaacac aggcagagcc tacaaacctt tgcaccagag ccctccacat   6840
atcagtgttt gttcatactc acttcaacag caaatgtgac tgctgagatt aagattttac   6900
acaagatggt ctgtaatttc acagttagtt ttatcccatt aggtatgaaa gaattagcat   6960
aattcccctt aaacatgaat gaatcttaga ttttttaata aatagttttg gaagtaaaga   7020
cagagacatc aggagcacaa ggaatagcct gagaggacaa acagaacaag aaagagtctg   7080
gaaatacaca ggatgttctt ggcctcctca aagcaagtgc aagcagatag taccagcagc   7140
cccaggctat cagagcccag tgaagagaag taccatgaaa gccacagctc taaccaccct   7200
gttccagagt gacagacagt ccccaagaca agccagcctg agccagagag agaactgcaa   7260
gagaaagttt ctaatttagg ttctgttaga ttcagacaag tgcaggtcat cctctctcca   7320
cagctactca cctctccagc ctaacaaagc ctgcagtcca cactccaacc ctggtgtctc   7380
acctcctagc ctctcccaac atcctgctct ctgaccatct tctgcatctc tcatctcacc   7440
atctcccact gtctacagcc tactcttgca actaccatct cattttctga catcctgtct   7500
acatcttctg ccatactctg ccatctacca taccacctct taccatctac cacaccatct   7560
tttatctcca tccctctcag aagcctccaa gctgaatcct gctttatgtg ttcatctcag   7620
cccctgcatg gaaagctgac cccagaggca gaactattcc cagagagctt ggccaagaaa   7680
aacaaaacta ccagcctggc caggctcagg agtagtaagc tgcagtgtct gttgtgttct   7740
agcttcaaca gctgcaggag ttccactctc aaatgctcca catttctcac atcctcctga   7800
```

-continued

```
ttctggtcac tacccatctt caaagaacag aatatctcac atcagcatac tgtgaaggac   7860
tagtcatggg tgcagctgct cagagctgca aagtcattct ggatggtgga gagcttacaa   7920
acatttcatg atgctccccc cgctctgatg gctggagccc aatccctaca cagactcctg   7980
ctgtatgtgt tttcctttca ctctgagcca cagccagagg gcaggcattc agtctcctct   8040
tcaggctggg gctggggcac tgagaactca cccaacacct tgctctcact ccttctgcaa   8100
aacaagaaag agctttgtgc tgcagtagcc atgaagaatg aaaggaaggc tttaactaaa   8160
aaatgtcaga gattattttc aaccccttac tgtggatcac cagcaaggag gaaacacaac   8220
acagagacat tttttcccct caaattatca aaagaatcac tgcatttgtt aaagagagca   8280
actgaatcag gaagcagagt tttgaacata tcagaagtta ggaatctgca tcagagacaa   8340
atgcagtcat ggttgtttgc tgcataccag ccctaatcat tagaagcctc atggacttca   8400
aacatcattc cctctgacaa gatgctctag cctaactcca tgagataaaa taaatctgcc   8460
tttcagagcc aaagaagagt ccaccagctt cttctcagtg tgaacaagag ctccagtcag   8520
gttagtcagt ccagtgcagt agaggagacc agtctgcatc ctctaatttt caaaggcaag   8580
aagatttgtt taccctggac accaggcaca agtgaggtca cagagctctt agatatgcag   8640
tcctcatgag tgaggagact aaagcgcatg ccatcaagac ttcagtgtag agaaaacctc   8700
caaaaaagcc tcctcactac ttctggaata gctcagaggc cgaggcggcc tcggcctctg   8760
cataaataaa aaaaattagt cagccatggg gcggagaatg ggcggaactg ggcggagtta   8820
ggggcgggat gggcggagtt aggggcggga ctatggttgc tgactaattg agatgcatgc   8880
tttgcatact tctgcctgct ggggagcctg gggactttcc acacctggtt gctgactaat   8940
tgagatgcat gctttgcata cttctgcctg ctggggagcc tggggacttt ccacacccta   9000
actgacacac attccacagc tgcattaatg aatcggccaa cgcgcgggga gaggcggttt   9060
gcgtattggg cgctcttccg cttcctcgct cactgactcg ctgcgctcgg tcgttcggct   9120
gcggcgagcg gtatcagctc actcaaaggc ggtaatacgg ttatccacag aatcagggga   9180
taacgcagga aagaacatgt gagcaaaagg ccagcaaaag gccaggaacc gtaaaaaggc   9240
cgcgttgctg gcgtttttcc ataggctccg cccccctgac gagcatcaca aaaatcgacg   9300
ctcaagtcag aggtggcgaa acccgacagg actataaaga taccaggcgt ttccccctgg   9360
aagctccctc gtgcgctctc ctgttccgac cctgccgctt accggatacc tgtccgcctt   9420
tctcccttcg ggaagcgtgg cgctttctca tagctcacgc tgtaggtatc tcagttcggt   9480
gtaggtcgtt cgctccaagc tgggctgtgt gcacgaaccc cccgttcagc ccgaccgctg   9540
cgccttatcc ggtaactatc gtcttgagtc caacccggta agacacgact tatcgccact   9600
ggcagcagcc actggtaaca ggattagcag agcgaggtat gtaggcggtg ctacagagtt   9660
cttgaagtgg tggcctaact acggctacac tagaagaaca gtatttggta tctgcgctct   9720
gctgaagcca gttaccttcg gaaaaagagt tggtagctct tgatccggca aacaaaccac   9780
cgctggtagc ggtggttttt ttgtttgcaa gcagcagatt acgcgcagaa aaaaaggatc   9840
tcaagaagat cctttgatct tttctacggg gtctgacgct cagtggaacg aaaactcacg   9900
ttaagggatt ttggtcatga gattatcaaa aaggatcttc acctagatcc ttttaaatta   9960
aaaatgaagt tttaaatcaa tctaaagtat atatgagtaa acttggtctg acagttacca  10020
atgcttaatc agtgaggcac ctatctcagc gatctgtcta tttcgttcat ccatagttgc  10080
ctgactcctg caaaccacgt tgtgtctcaa aatctctgat gttacattgc acaagataaa  10140
aatatatcat catgaacaat aaaactgtct gcttacataa acagtaatac aaggggtgtt  10200
```

```
atgagccata ttcaacggga aacgtcttgc tcgaggccgc gattaaattc caacatggat  10260

gctgatttat atgggtataa atgggctcgc gataatgtcg ggcaatcagg tgcgacaatc  10320

tatcgattgt atgggaagcc cgatgcgcca gagttgtttc tgaaacatgg caaaggtagc  10380

gttgccaatg atgttacaga tgagatggtc agactaaact ggctgacgga atttatgcct  10440

cttccgacca tcaagcattt tatccgtact cctgatgatg catggttact caccactgcg  10500

atccccggga aaacagcatt ccaggtatta gaagaatatc ctgattcagg tgaaaatatt  10560

gttgatgcgc tggcagtgtt cctgcgccgg ttgcattcga ttcctgtttg taattgtcct  10620

tttaacagcg atcgcgtatt tcgtctcgct caggcgcaat cacgaatgaa taacggtttg  10680

gttgatgcga gtgattttga tgacgagcgt aatggctggc ctgttgaaca agtctggaaa  10740

gaaatgcata agcttttgcc attctcaccg gattcagtcg tcactcatgg tgatttctca  10800

cttgataacc ttatttttga cgaggggaaa ttaataggtt gtattgatgt tggacgagtc  10860

ggaatcgcag accgatacca ggatcttgcc atcctatgga actgcctcgg tgagttttct  10920

ccttcattac agaaacggct ttttcaaaaa tatggtattg ataatcctga tatgaataaa  10980

ttgcagtttc atttgatgct cgatgagttt ttctaagggc ggcctgccac catacccacg  11040

ccgaaacaag cgctcatgag cccgaagtgg cgagcccgat cttccccatc ggtgatgtcg  11100

gcgatatagg cgccagcaac cgcacctgtg gcgccggtga tgagggcgcg ccaagtcgac  11160

gtccggcagt c                                                       11171
```

<210> SEQ ID NO 5
<211> LENGTH: 11309
<212> TYPE: DNA
<213> ORGANISM: Artificial Sequence
<220> FEATURE:
<223> OTHER INFORMATION: Synthetic polynucleotide

<400> SEQUENCE: 5

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctcctg gtggcgaggg gagggggtg gtcctcgaac gccttgcaga     600

actggcctgg atacagagtg gaccggctgg ccccatctgg aagacttcga gatacactgt    660

tgtcttactg cgctcaacag tgtatctcga agtcttccaa atggtgccag ccatcgcagc    720

ggggtgcagg aaatgggggc agcccccctt tttggctatc cttccacgtg ttcttttttg    780

tatcttttgt gtttcctaga aaacatctca gtcaccaccg cagccctagg aatgcatcta    840

gacaattgta ctaaccttct tctctttcct ctcctgacag tccggaaagc caccatgtac    900

gccctgttcc tgctggccag cctgctgggc gccgccctgg ccggccccgt gctgggcctg    960

aaggagtgca cccgcggcag cgccgtgtgg tgccagaacg tgaagaccgc cagcgactgc   1020
```

-continued

```
ggcgccgtga agcactgcct gcagaccgtg tggaacaagc ccaccgtgaa gagcctgccc   1080
tgcgacatct gcaaggacgt ggtgaccgcc gccggcgaca tgctgaagga caacgccacc   1140
gaggaggaga tcctggtgta cctggagaag acctgcgact ggctgcccaa gcccaacatg   1200
agcgccagct gcaaggagat cgtggacagc tacctgcccg tgatcctgga catcatcaag   1260
ggcgagatga gccgccccgg cgaggtgtgc agcgccctga acctgtgcga gagcctgcag   1320
aagcacctgg ccgagctgaa ccaccagaag cagctggaga gcaacaagat ccccgagctg   1380
gacatgaccg aggtggtggc cccctcatg gccaacatcc ccctgctgct gtacccccag   1440
gacggccccc gcagcaagcc ccagcccaag gacaacggcg acgtgtgcca ggactgcatc   1500
cagatggtga ccgacatcca gaccgccgtg cgcaccaaca gcaccttcgt gcaggccctg   1560
gtggagcacg tgaaggagga gtgcgaccgc ctgggccccg gcatggccga catctgcaag   1620
aactacatca gccagtacag cgagatcgcc atccagatga tgatgcacat gcagcccaag   1680
gagatctgcg ccctggtggg cttctgcgac gaggtgaagg agatgcccat gcagaccctg   1740
gtgcccgcca aggtggccag caagaacgtg atccccgccc tggagctggt ggagcccatc   1800
aagaagcacg aggtgcccgc caagagcgac gtgtactgcg aggtgtgcga gttcctggtg   1860
aaggaggtga ccaagctgat cgacaacaac aagaccgaga aggagatcct ggacgccttc   1920
gacaagatgt gcagcaagct gcccaagagc ctgagcgagg agtgccagga ggtggtggac   1980
acctacggca gcagcatcct gagcatcctg ctggaggagg tgagccccga gctggtgtgc   2040
agcatgctgc acctgtgcag cggcacccgc ctgcccgccc tgaccgtgca cgtgacccag   2100
cccaaggacg gcggcttctg cgaggtgtgc aagaagctgg tgggctacct ggaccgcaac   2160
ctggagaaga acagcaccaa gcaggagatc ctggccgccc tggagaaggg ctgcagcttc   2220
ctgcccgacc cctaccagaa gcagtgcgac cagttcgtgg ccgagtacga gcccgtgctg   2280
atcgagatcc tggtggaggt gatggacccc agcttcgtgt gcctgaagat cggcgcctgc   2340
cccagcgccc acaagcccct gctgggcacc gagaagtgca tctggggccc cagctactgg   2400
tgccagaaca ccgagaccgc cgcccagtgc aacgccgtgg agcactgcaa gcgccacgtg   2460
tggaacgagg gcagaggaag tcttctgaca tgcggagacg tggaagagaa tcccggccct   2520
atggaattca gcagccccag cagagaggaa tgccccaagc ctctgagccg ggtgtcaatc   2580
atggccggat ctctgacagg actgctgctg cttcaggccg tgtcttgggc ttctggcgct   2640
agaccttgca tccccaagag cttcggctac agcagcgtcg tgtgcgtgtg caatgccacc   2700
tactgcgaca gcttcgaccc tcctaccttt cctgctctgg gcaccttcag cagatacgag   2760
agcaccagat ccggcagacg gatggaactg agcatgggac ccatccaggc caatcacaca   2820
ggcactggcc tgctgctgac actgcagcct gagcagaaat tccagaaagt gaaaggcttc   2880
ggcggagcca tgacagatgc cgccgctctg aatatcctgg ctctgtctcc accagctcag   2940
aacctgctgc tcaagagcta cttcagcgag gaaggcatcg gctacaacat catcagagtg   3000
cccatggcca gctgcgactt cagcatcagg acctacacct acgccgacac acccgacgat   3060
ttccagctgc acaacttcag cctgcctgaa gaggacacca agctgaagat ccctctgatc   3120
cacagagccc tgcagctggc acaaagaccc gtgtcactgc tggcctctcc atggacatct   3180
cccacctggc tgaaaacaaa tggcgccgtg aatggcaagg gcagcctgaa aggccaacct   3240
ggcgacatct accaccagac ctgggccaga tacttcgtga agttcctgga cgcctatgcc   3300
gagcacaagc tgcagttttg ggccgtgaca gccgagaacg aaccttctgc tggactgctg   3360
agcggctacc cctttcagtg cctgggcttt acacccgagc accagcggga ctttatcgcc   3420
```

-continued

```
cgtgatctgg gacccacact ggccaatagc acccaccata atgtgcggct gctgatgctg   3480
gacgaccaga gactgcttct gccccactgg gctaaagtgg tgctgacaga tcctgaggcc   3540
gccaaatacg tgcacggaat cgccgtgcac tggtatctgg actttctggc ccctgccaag   3600
gccacactgg gagagacaca cagactgttc cccaacacca tgctgttcgc cagcgaagcc   3660
tgtgtgggca gcaagttttg ggaacagagc gtgcggctcg gcagctggga tagaggcatg   3720
cagtacagcc acagcatcat caccaacctg ctgtaccacg tcgtcggctg gaccgactgg   3780
aatctggccc tgaatcctga aggcggccct aactgggtcc gaaacttcgt ggacagcccc   3840
atcatcgtgg acatcaccaa ggacaccttc tacaagcagc ccatgttcta ccacctggga   3900
cacttcagca agttcatccc cgagggctct cagcgcgttg gactggtggc ttcccagaag   3960
aacgatctgg acgccgtggc tctgatgcac cctgatggat ctgctgtggt ggtggtcctg   4020
aaccgcagca gcaaagatgt gcccctgacc atcaaggatc ccgccgtggg attcctggaa   4080
acaatcagcc ctggctactc catccacacc tacctgtggc gtagacagtg acaattgtta   4140
attaagttta aaccctcgag gccgcaagcc gcatcgatac cgtcgactag agctcgctga   4200
tcagcctcga ctgtgccttc tagttgccag ccatctgttg tttgcccctc ccccgtgcct   4260
tccttgaccc tggaaggtgc cactcccact gtcctttcct aataaaatga ggaaattgca   4320
tcgcattgtc tgagtaggtg tcattctatt ctggggggtg gggtggggca ggacagcaag   4380
ggggaggatt gggaagacaa tagcaggcat gctggggaga gatccacgat aacaaacagc   4440
ttttttgggg tgaacatatt gactgaattc cctgcaggtt ggccactccc tctctgcgcg   4500
ctcgctcgct cactgaggcc gcccgggcaa agcccgggcg tcgggcgacc tttggtcgcc   4560
cggcctcagt gagcgagcga gcgcgcagag agggagtggc caactccatc actaggggtt   4620
cctgcggccg ctcgtacggt ctcgaggaat tcctgcagga taacttgcca acctcattct   4680
aaaatgtata tagaagccca aaagacaata acaaaaatat tcttgtagaa caaaatggga   4740
aagaatgttc cactaaatat caagatttag agcaaagcat gagatgtgtg gggatagaca   4800
gtgaggctga taaaatagag tagagctcag aaacagaccc attgatatat gtaagtgacc   4860
tatgaaaaaa atatggcatt ttacaatggg aaaatgatgg tctttttctt ttttagaaaa   4920
acagggaaat atatttatat gtaaaaaata aaagggaacc catatgtcat accatacaca   4980
caaaaaaatt ccagtgaatt ataagtctaa atggagaagg caaaacttta aatcttttag   5040
aaaataatat agaagcatgc agaccagcct ggccaacatg atgaaaccct ctctactaat   5100
aataaaatca gtagaactac tcaggactac tttgagtggg aagtcctttt ctatgaagac   5160
ttctttggcc aaaattaggc tctaaatgca aggagatagt gcatcatgcc tggctgcact   5220
tactgataaa tgatgttatc accatcttta accaaatgca caggaacaag ttatggtact   5280
gatgtgctgg attgagaagg agctctactt ccttgacagg acacatttgt atcaacttaa   5340
aaaagcagat ttttgccagc agaactattc attcagaggt aggaaactta gaatagatga   5400
tgtcactgat tagcatggct tccccatctc cacagctgct tcccacccag gttgcccaca   5460
gttgagtttg tccagtgctc agggctgccc actctcagta agaagcccca caccagcccc   5520
tctccaaata tgttggctgt tccttccatt aaagtgaccc cactttagag cagcaagtgg   5580
atttctgttt cttacagttc aggaaggagg agtcagctgt gagaacctgg agcctgagat   5640
gcttctaagt cccactgcta ctggggtcag ggaagccaga ctccagcatc agcagtcagg   5700
agcactaagc ccttgccaac atcctgtttc tcagagaaac tgcttccatt ataatggttg   5760
```

-continued

```
tcctttttta agctatcaag ccaaacaacc agtgtctacc attattctca tcacctgaag   5820
ccaagggttc tagcaaaagt caagctgtct tgtaatggtt gatgtgcctc cagcttctgt   5880
cttcagtcac tccactctta gcctgctctg aatcaactct gaccacagtt ccctggagcc   5940
cctgccacct gctgcccctg ccaccttctc catctgcagt gctgtgcagc cttctgcact   6000
cttgcagagc taataggtgg agacttgaag gaagaggagg aaagtttctc ataatagcct   6060
tgctgcaagc tcaaatggga ggtgggcact gtgcccagga gccttggagc aaaggctgtg   6120
cccaacctct gactgcatcc aggtttggtc ttgacagaga taagaagccc tggcttttgg   6180
agccaaaatc taggtcagac ttaggcagga ttctcaaagt ttatcagcag aacatgaggc   6240
agaagaccct ttctgctcca gcttcttcag gctcaacctt catcagaata gatagaaaga   6300
gaggctgtga gggttcttaa aacagaagca aatctgactc agagaataaa caacctccta   6360
gtaaactaca gcttagacag agcatctggt ggtgagtgtg ctcagtgtcc tactcaactg   6420
tctggtatca gccctcatga ggacttctct tctttccctc atagacctcc atctctgttt   6480
tccttagcct gcagaaatct ggatggctat tcacagaatg cctgtgcttt cagagttgca   6540
tttttctct ggtattctgg ttcaagcatt tgaaggtagg aaaggttctc caagtgcaag   6600
aaagccagcc ctgagcctca actgcctggc tagtgtggtc agtaggatgc aaaggctgtt   6660
gaatgccaca aggccaaact ttaacctgtg taccacaagc ctagcagcag aggcagctct   6720
gctcactgga actctctgtc ttctttctcc tgagcctttt cttttcctga gttttctagc   6780
tctcctcaac cttacctctg ccctacccag gacaaaccca agagccactg tttctgtgat   6840
gtcctctcca gccctaatta ggcatcatga cttcagcctg accttccatg ctcagaagca   6900
gtgctaatcc acttcagatg agctgctcta tgcaacacag gcagagccta caaacctttg   6960
caccagagcc ctccacatat cagtgtttgt tcatactcac ttcaacagca aatgtgactg   7020
ctgagattaa gattttacac aagatggtct gtaatttcac agttagtttt atcccattag   7080
gtatgaaaga attagcataa ttccccttaa acatgaatga atcttagatt ttttaataaa   7140
tagttttgga agtaaagaca gagacatcag gagcacaagg aatagcctga gaggacaaac   7200
agaacaagaa agagtctgga aatacacagg atgttcttgg cctcctcaaa gcaagtgcaa   7260
gcagatagta ccagcagccc caggctatca gagcccagtg aagagaagta ccatgaaagc   7320
cacagctcta accaccctgt tccagagtga cagacagtcc ccaagacaag ccagcctgag   7380
ccagagagag aactgcaaga gaaagtttct aatttaggtt ctgttagatt cagacaagtg   7440
caggtcatcc tctctccaca gctactcacc tctccagcct aacaaagcct gcagtccaca   7500
ctccaaccct ggtgtctcac ctcctagcct ctcccaacat cctgctctct gaccatcttc   7560
tgcatctctc atctcaccat ctcccactgt ctacagccta ctcttgcaac taccatctca   7620
ttttctgaca tcctgtctac atcttctgcc atactctgcc atctaccata ccacctctta   7680
ccatctacca caccatcttt tatctccatc cctctcagaa gcctccaagc tgaatcctgc   7740
tttatgtgtt catctcagcc cctgcatgga aagctgaccc cagaggcaga actattccca   7800
gagagcttgg ccaagaaaaa caaaactacc agcctggcca ggctcaggag tagtaagctg   7860
cagtgtctgt tgtgttctag cttcaacagc tgcaggagtt ccactctcaa atgctccaca   7920
tttctcacat cctcctgatt ctggtcacta cccatcttca aagaacagaa tatctcacat   7980
cagcatactg tgaaggacta gtcatgggtg cagctgctca gagctgcaaa gtcattctgg   8040
atggtggaga gcttacaaac atttcatgat gctccccccg ctctgatggc tggagcccaa   8100
tccctacaca gactcctgct gtatgtgttt tcctttcact ctgagccaca gccagagggc   8160
```

```
aggcattcag tctcctcttc aggctggggc tggggcactg agaactcacc caacaccttg   8220
ctctcactcc ttctgcaaaa caagaaagag ctttgtgctg cagtagccat gaagaatgaa   8280
aggaaggctt taactaaaaa atgtcagaga ttattttcaa ccccttactg tggatcacca   8340
gcaaggagga aacacaacac agagacattt tttcccctca aattatcaaa agaatcactg   8400
catttgttaa agagagcaac tgaatcagga agcagagttt tgaacatatc agaagttagg   8460
aatctgcatc agagacaaat gcagtcatgg ttgtttgctg cataccagcc ctaatcatta   8520
gaagcctcat ggacttcaaa catcattccc tctgacaaga tgctctagcc taactccatg   8580
agataaaata aatctgcctt tcagagccaa agaagagtcc accagcttct tctcagtgtg   8640
aacaagagct ccagtcaggt tagtcagtcc agtgcagtag aggagaccag tctgcatcct   8700
ctaattttca aaggcaagaa gatttgttta ccctggacac caggcacaag tgaggtcaca   8760
gagctcttag atatgcagtc ctcatgagtg aggagactaa agcgcatgcc atcaagactt   8820
cagtgtagag aaaacctcca aaaaagcctc ctcactactt ctggaatagc tcagaggccg   8880
aggcggcctc ggcctctgca taaataaaaa aaattagtca gccatggggc ggagaatggg   8940
cggaactggg cggagttagg ggcgggatgg gcggagttag gggcgggact atggttgctg   9000
actaattgag atgcatgctt tgcatacttc tgcctgctgg ggagcctggg gactttccac   9060
acctggttgc tgactaattg agatgcatgc tttgcatact tctgcctgct ggggagcctg   9120
gggactttcc acaccctaac tgacacacat tccacagctg cattaatgaa tcggccaacg   9180
cgcggggaga ggcggtttgc gtattgggcg ctcttccgct tcctcgctca ctgactcgct   9240
gcgctcggtc gttcggctgc ggcgagcggt atcagctcac tcaaaggcgg taatacggtt   9300
atccacagaa tcaggggata acgcaggaaa gaacatgtga gcaaaaggcc agcaaaaggc   9360
caggaaccgt aaaaaggccg cgttgctggc gtttttccat aggctccgcc cccctgacga   9420
gcatcacaaa aatcgacgct caagtcagag gtggcgaaac ccgacaggac tataaagata   9480
ccaggcgttt ccccctggaa gctccctcgt gcgctctcct gttccgaccc tgccgcttac   9540
cggatacctg tccgcctttc tcccttcggg aagcgtggcg ctttctcata gctcacgctg   9600
taggtatctc agttcggtgt aggtcgttcg ctccaagctg ggctgtgtgc acgaaccccc   9660
cgttcagccc gaccgctgcg ccttatccgg taactatcgt cttgagtcca acccggtaag   9720
acacgactta tcgccactgg cagcagccac tggtaacagg attagcagag cgaggtatgt   9780
aggcggtgct acagagttct tgaagtggtg gcctaactac ggctacacta gaagaacagt   9840
atttggtatc tgcgctctgc tgaagccagt taccttcgga aaaagagttg gtagctcttg   9900
atccggcaaa caaaccaccg ctggtagcgg tggttttttt gtttgcaagc agcagattac   9960
gcgcagaaaa aaaggatctc aagaagatcc tttgatcttt tctacggggt ctgacgctca  10020
gtggaacgaa aactcacgtt aagggatttt ggtcatgaga ttatcaaaaa ggatcttcac  10080
ctagatcctt ttaaattaaa aatgaagttt taaatcaatc taaagtatat atgagtaaac  10140
ttggtctgac agttaccaat gcttaatcag tgaggcacct atctcagcga tctgtctatt  10200
tcgttcatcc atagttgcct gactcctgca aaccacgttg tgtctcaaaa tctctgatgt  10260
tacattgcac aagataaaaa tatatcatca tgaacaataa aactgtctgc ttacataaac  10320
agtaatacaa ggggtgttat gagccatatt caacgggaaa cgtcttgctc gaggccgcga  10380
ttaaattcca acatggatgc tgatttatat gggtataaat gggctcgcga taatgtcggg  10440
caatcaggtg cgacaatcta tcgattgtat gggaagcccg atgcgccaga gttgtttctg  10500
```

aaacatggca aaggtagcgt tgccaatgat gttacagatg agatggtcag actaaactgg 10560
ctgacggaat ttatgcctct tccgaccatc aagcatttta tccgtactcc tgatgatgca 10620
tggttactca ccactgcgat ccccgggaaa acagcattcc aggtattaga agaatatcct 10680
gattcaggtg aaaatattgt tgatgcgctg gcagtgttcc tgcgccggtt gcattcgatt 10740
cctgtttgta attgtccttt taacagcgat cgcgtatttc gtctcgctca ggcgcaatca 10800
cgaatgaata acggtttggt tgatgcgagt gattttgatg acgagcgtaa tggctggcct 10860
gttgaacaag tctggaaaga aatgcataag cttttgccat tctcaccgga ttcagtcgtc 10920
actcatggtg atttctcact tgataacctt atttttgacg aggggaaatt aataggttgt 10980
attgatgttg gacgagtcgg aatcgcagac cgataccagg atcttgccat cctatggaac 11040
tgcctcggtg agttttctcc ttcattacag aaacggcttt ttcaaaaata tggtattgat 11100
aatcctgata tgaataaatt gcagtttcat ttgatgctcg atgagttttt ctaagggcgg 11160
cctgccacca tacccacgcc gaaacaagcg ctcatgagcc cgaagtggcg agcccgatct 11220
tccccatcgg tgatgtcggc gatataggcg ccagcaaccg cacctgtggc gccggtgatg 11280
agggcgcgcc aagtcgacgt ccggcagtc 11309

<210> SEQ ID NO 6
<211> LENGTH: 11293
<212> TYPE: DNA
<213> ORGANISM: Artificial Sequence
<220> FEATURE:
<223> OTHER INFORMATION: Synthetic polynucleotide

<400> SEQUENCE: 6
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctgcag ccctaggaat gcatctagac aattgtacta accttcttct 600
ctttcctctc ctgacagtcc ggaaagccac catgtacgcc ctgttcctgc tggccagcct 660
gctgggcgcc gccctggccg gccccgtgct gggcctgaag gagtgcaccc gcggcagcgc 720
cgtgtggtgc cagaacgtga agaccgccag cgactgcggc gccgtgaagc actgcctgca 780
gaccgtgtgg aacaagccca ccgtgaagag cctgccctgc gacatctgca aggacgtggt 840
gaccgccgcc ggcgacatgc tgaaggacaa cgccaccgag gaggagatcc tggtgtacct 900
ggagaagacc tgcgactggc tgcccaagcc caacatgagc gccagctgca aggagatcgt 960
ggacagctac ctgcccgtga tcctggacat catcaagggc gagatgagcc gccccggcga 1020
ggtgtgcagc gccctgaacc tgtgcgagag cctgcagaag cacctggccg agctgaacca 1080
ccagaagcag ctggagagca acaagatccc cgagctggac atgaccgagg tggtggcccc 1140
cttcatggcc aacatccccc tgctgctgta cccccaggac ggcccccgca gcaagcccca 1200
gcccaaggac aacggcgacg tgtgccagga ctgcatccag atggtgaccg acatccagac 1260

```
cgccgtgcgc accaacagca ccttcgtgca ggccctggtg gagcacgtga aggaggagtg   1320
cgaccgcctg ggccccggca tggccgacat ctgcaagaac tacatcagcc agtacagcga   1380
gatcgccatc cagatgatga tgcacatgca gcccaaggag atctgcgccc tggtgggctt   1440
ctgcgacgag gtgaaggaga tgcccatgca gaccctggtg cccgccaagg tggccagcaa   1500
gaacgtgatc cccgccctgg agctggtgga gcccatcaag aagcacgagg tgcccgccaa   1560
gagcgacgtg tactgcgagg tgtgcgagtt cctggtgaag gaggtgacca agctgatcga   1620
caacaacaag accgagaagg agatcctgga cgccttcgac aagatgtgca gcaagctgcc   1680
caagagcctg agcgaggagt gccaggaggt ggtggacacc tacggcagca gcatcctgag   1740
catcctgctg gaggaggtga gccccgagct ggtgtgcagc atgctgcacc tgtgcagcgg   1800
cacccgcctg cccgccctga ccgtgcacgt gacccagccc aaggacggcg gcttctgcga   1860
ggtgtgcaag aagctggtgg gctacctgga ccgcaacctg gagaagaaca gcaccaagca   1920
ggagatcctg gccgccctgg agaagggctg cagcttcctg cccgacccct accagaagca   1980
gtgcgaccag ttcgtggccg agtacgagcc cgtgctgatc gagatcctgg tggaggtgat   2040
ggaccccagc ttcgtgtgcc tgaagatcgg cgcctgcccc agcgcccaca agcccctgct   2100
gggcaccgag aagtgcatct ggggccccag ctactggtgc cagaacaccg agaccgccgc   2160
ccagtgcaac gccgtggagc actgcaagcg ccacgtgtgg aactgattgt ggccgaaccg   2220
ccgaactcag aggccggccc cagaaaaccc gagcgagtag gggcggcgc gcaggaggga   2280
ggagaactgg gggcgcggga ggctggtggg tgtgggggt ggagatgtag aagatgtgac   2340
gccgcggccc ggcgggtgcc agattagcgg acgcggtgcc cgcggttgca acgggatccc   2400
gggcgctgca gcttgggagg cggctctccc caggcggcgt ccgcggagac acccatccgt   2460
gaaccccagg tcccgggccg ccggctcgcc gcgcaccagg ggccggcgga cagaagagcg   2520
gccgagcggc tcgaggctgg gggaccgcgg gcgcggccgc gcgctgccgg gcgggaggct   2580
ggggggccgg ggccggggcc gtgccccgga gcgggtcgga ggccggggcc ggggccgggg   2640
gacggcggct ccccgcgcgg ctccagcggc tcggggatcc cggccgggcc ccgcagggac   2700
catgatggaa ttcagcagcc ccagcagaga ggaatgcccc aagcctctga gccgggtgtc   2760
aatcatggcc ggatctctga caggactgct gctgcttcag gccgtgtctt gggcttctgg   2820
cgctagacct tgcatcccca agagcttcgg ctacagcagc gtcgtgtgcg tgtgcaatgc   2880
cacctactgc gacagcttcg accctcctac ctttcctgct ctgggcacct tcagcagata   2940
cgagagcacc agatccggca gacggatgga actgagcatg ggacccatcc aggccaatca   3000
cacaggcact ggcctgctgc tgacactgca gcctgagcag aaattccaga aagtgaaagg   3060
cttcggcgga gccatgacag atgccgccgc tctgaatatc ctggctctgt ctccaccagc   3120
tcagaacctg ctgctcaaga gctacttcag cgaggaaggc atcggctaca acatcatcag   3180
agtgcccatg gccagctgcg acttcagcat caggacctac acctacgccg acacacccga   3240
cgatttccag ctgcacaact tcagcctgcc tgaagaggac accaagctga agatccctct   3300
gatccacaga gccctgcagc tggcacaaag acccgtgtca ctgctggcct ctccatggac   3360
atctcccacc tggctgaaaa caaatggcgc cgtgaatggc aagggcagcc tgaaaggcca   3420
acctggcgac atctaccacc agacctgggc cagatacttc gtgaagttcc tggacgccta   3480
tgccgagcac aagctgcagt tttgggccgt gacagccgag aacgaacctt ctgctggact   3540
gctgagcggc tacccctttc agtgcctggg ctttacaccc gagcaccagc gggactttat   3600
```

cgcccgtgat ctgggaccca cactggccaa tagcacccac cataatgtgc ggctgctgat 3660
gctggacgac cagagactgc ttctgcccca ctgggctaaa gtggtgctga cagatcctga 3720
ggccgccaaa tacgtgcacg gaatcgccgt gcactggtat ctggactttc tggcccctgc 3780
caaggccaca ctgggagaga cacacagact gttccccaac accatgctgt tcgccagcga 3840
agcctgtgtg ggcagcaagt tttgggaaca gagcgtgcgg ctcggcagct gggatagagg 3900
catgcagtac agccacagca tcatcaccaa cctgctgtac cacgtcgtcg gctggaccga 3960
ctggaatctg gccctgaatc ctgaaggcgg ccctaactgg gtccgaaact tcgtggacag 4020
ccccatcatc gtggacatca ccaaggacac cttctacaag cagcccatgt tctaccacct 4080
gggacacttc agcaagttca tccccgaggg ctctcagcgc gttggactgg tggcttccca 4140
gaagaacgat ctggacgccg tggctctgat gcaccctgat ggatctgctg tggtggtggt 4200
cctgaaccgc agcagcaaag atgtgcccct gaccatcaag gatcccgccg tgggattcct 4260
ggaaacaatc agccctggct actccatcca cacctacctg tggcgtagac agtgacaatt 4320
gttaattaag tttaaaccct cgaggccgca agcaataaaa tatctttatt ttcattacat 4380
ctgtgtgttg gttttttgtg tggagatcca cgataacaaa cagctttttt ggggtgaaca 4440
tattgactga attccctgca ggttggccac tccctctctg cgcgctcgct cgctcactga 4500
ggccgcccgg gcaaagcccg ggcgtcgggc gacctttggt cgcccggcct cagtgagcga 4560
gcgagcgcgc agagagggag tggccaactc catcactagg ggttcctgcg gccgctcgta 4620
cggtctcgag gaattcctgc aggataactt gccaacctca ttctaaaatg tatatagaag 4680
cccaaaagac aataacaaaa atattcttgt agaacaaaat gggaaagaat gttccactaa 4740
atatcaagat ttagagcaaa gcatgagatg tgtggggata gacagtgagg ctgataaaat 4800
agagtagagc tcagaaacag acccattgat atatgtaagt gacctatgaa aaaaatatgg 4860
cattttacaa tgggaaaatg atggtctttt tctttttttag aaaaacaggg aaatatattt 4920
atatgtaaaa aataaaaggg aacccatatg tcataccata cacacaaaaa aattccagtg 4980
aattataagt ctaaatggag aaggcaaaac tttaaatctt ttagaaaata atatagaagc 5040
atgcagacca gcctggccaa catgatgaaa ccctctctac taataataaa atcagtagaa 5100
ctactcagga ctactttgag tgggaagtcc ttttctatga agacttcttt ggccaaaatt 5160
aggctctaaa tgcaaggaga tagtgcatca tgcctggctg cacttactga taaatgatgt 5220
tatcaccatc tttaaccaaa tgcacaggaa caagttatgg tactgatgtg ctggattgag 5280
aaggagctct acttccttga caggacacat ttgtatcaac ttaaaaaagc agatttttgc 5340
cagcagaact attcattcag aggtaggaaa cttagaatag atgatgtcac tgattagcat 5400
ggcttcccca tctccacagc tgcttcccac ccaggttgcc cacagttgag tttgtccagt 5460
gctcagggct gcccactctc agtaagaagc cccacaccag cccctctcca aatatgttgg 5520
ctgttccttc cattaaagtg accccacttt agagcagcaa gtggatttct gtttcttaca 5580
gttcaggaag gaggagtcag ctgtgagaac ctggagcctg agatgcttct aagtcccact 5640
gctactgggg tcagggaagc cagactccag catcagcagt caggagcact aagcccttgc 5700
caacatcctg tttctcagag aaactgcttc cattataatg gttgtccttt tttaagctat 5760
caagccaaac aaccagtgtc taccattatt ctcatcacct gaagccaagg gttctagcaa 5820
aagtcaagct gtcttgtaat ggttgatgtg cctccagctt ctgtcttcag tcactccact 5880
cttagcctgc tctgaatcaa ctctgaccac agttccctgg agcccctgcc acctgctgcc 5940
cctgccacct tctccatctg cagtgctgtg cagccttctg cactcttgca gagctaatag 6000

-continued gtggagactt gaaggaagag gaggaaagtt tctcataata gccttgctgc aagctcaaat 6060
gggaggtggg cactgtgccc aggagccttg gagcaaaggc tgtgcccaac ctctgactgc 6120
atccaggttt ggtcttgaca gagataagaa gccctggctt ttggagccaa aatctaggtc 6180
agacttaggc aggattctca aagtttatca gcagaacatg aggcagaaga cccttttctgc 6240 tccagcttct tcaggctcaa ccttcatcag aatagataga aagagaggct gtgagggttc 6300
ttaaaacaga agcaaatctg actcagagaa taaacaacct cctagtaaac tacagcttag 6360
acagagcatc tggtggtgag tgtgctcagt gtcctactca actgtctggt atcagccctc 6420
atgaggactt ctcttctttc cctcatagac ctccatctct gttttcctta gcctgcagaa 6480
atctggatgg ctattcacag aatgcctgtg ctttcagagt tgcatttttt ctctggtatt 6540
ctggttcaag catttgaagg taggaaaggt tctccaagtg caagaaagcc agccctgagc 6600
ctcaactgcc tggctagtgt ggtcagtagg atgcaaaggc tgttgaatgc cacaaggcca 6660
aactttaacc tgtgtaccac aagcctagca gcagaggcag ctctgctcac tggaactctc 6720
tgtcttcttt ctcctgagcc ttttcttttc ctgagttttc tagctctcct caaccttacc 6780
tctgccctac ccaggacaaa cccaagagcc actgtttctg tgatgtcctc tccagcccta 6840
attaggcatc atgacttcag cctgaccttc catgctcaga agcagtgcta atccacttca 6900
gatgagctgc tctatgcaac acaggcagag cctacaaacc tttgcaccag agccctccac 6960
atatcagtgt ttgttcatac tcacttcaac agcaaatgtg actgctgaga ttaagatttt 7020
acacaagatg gtctgtaatt tcacagttag ttttatccca ttaggtatga aagaattagc 7080
ataattcccc ttaaacatga atgaatctta gattttttaa taaatagttt tggaagtaaa 7140
gacagagaca tcaggagcac aaggaatagc ctgagaggac aaacagaaca agaaagagtc 7200
tggaaataca caggatgttc ttggcctcct caaagcaagt gcaagcagat agtaccagca 7260
gccccaggct atcagagccc agtgaagaga agtaccatga aagccacagc tctaaccacc 7320
ctgttccaga gtgacagaca gtccccaaga caagccagcc tgagccagag agagaactgc 7380
aagagaaagt ttctaattta ggttctgtta gattcagaca agtgcaggtc atcctctctc 7440
cacagctact cacctctcca gcctaacaaa gcctgcagtc cacactccaa ccctggtgtc 7500
tcacctccta gcctctccca acatcctgct ctctgaccat cttctgcatc tctcatctca 7560
ccatctccca ctgtctacag cctactcttg caactaccat ctcattttct gacatcctgt 7620
ctacatcttc tgccatactc tgccatctac cataccacct cttaccatct accacaccat 7680
cttttatctc catccctctc agaagcctcc aagctgaatc ctgctttatg tgttcatctc 7740
agcccctgca tggaaagctg accccagagg cagaactatt cccagagagc ttggccaaga 7800
aaaacaaaac taccagcctg gccaggctca ggagtagtaa gctgcagtgt ctgttgtgtt 7860
ctagcttcaa cagctgcagg agttccactc tcaaatgctc cacatttctc acatcctcct 7920
gattctggtc actacccatc ttcaaagaac agaatatctc acatcagcat actgtgaagg 7980
actagtcatg ggtgcagctg ctcagagctg caaagtcatt ctggatggtg gagagcttac 8040
aaacatttca tgatgctccc cccgctctga tggctggagc ccaatcccta cacagactcc 8100
tgctgtatgt gttttccttt cactctgagc cacagccaga gggcaggcat tcagtctcct 8160
cttcaggctg gggctggggc actgagaact cacccaacac cttgctctca ctccttctgc 8220
aaaacaagaa agagctttgt gctgcagtag ccatgaagaa tgaaaggaag gctttaacta 8280
aaaaatgtca gagattattt tcaacccctt actgtggatc accagcaagg aggaaacaca 8340

-continued

```
acacagagac atttttttccc ctcaaattat caaaagaatc actgcatttg ttaaagagag   8400
caactgaatc aggaagcaga gttttgaaca tatcagaagt taggaatctg catcagagac   8460
aaatgcagtc atggttgttt gctgcatacc agccctaatc attagaagcc tcatggactt   8520
caaacatcat tccctctgac aagatgctct agcctaactc catgagataa aataaatctg   8580
cctttcagag ccaaagaaga gtccaccagc ttcttctcag tgtgaacaag agctccagtc   8640
aggttagtca gtccagtgca gtagaggaga ccagtctgca tcctctaatt ttcaaaggca   8700
agaagatttg tttaccctgg acaccaggca caagtgaggt cacagagctc ttagatatgc   8760
agtcctcatg agtgaggaga ctaaagcgca tgccatcaag acttcagtgt agagaaaacc   8820
tccaaaaaag cctcctcact acttctggaa tagctcagag gccgaggcgg cctcggcctc   8880
tgcataaata aaaaaaatta gtcagccatg gggcggagaa tgggcggaac tgggcggagt   8940
taggggcggg atgggcggag ttaggggcgg gactatggtt gctgactaat tgagatgcat   9000
gctttgcata cttctgcctg ctggggagcc tggggacttt ccacacctgg ttgctgacta   9060
attgagatgc atgctttgca tacttctgcc tgctggggag cctggggact ttccacaccc   9120
taactgacac acattccaca gctgcattaa tgaatcggcc aacgcgcggg gagaggcggt   9180
ttgcgtattg ggcgctcttc cgcttcctcg ctcactgact cgctgcgctc ggtcgttcgg   9240
ctgcggcgag cggtatcagc tcactcaaag gcggtaatac ggttatccac agaatcaggg   9300
gataacgcag gaaagaacat gtgagcaaaa ggccagcaaa aggccaggaa ccgtaaaaag   9360
gccgcgttgc tggcgttttt ccataggctc cgcccccctg acgagcatca caaaaatcga   9420
cgctcaagtc agaggtggcg aaacccgaca ggactataaa gataccaggc gtttccccct   9480
ggaagctccc tcgtgcgctc tcctgttccg accctgccgc ttaccggata cctgtccgcc   9540
tttctccctt cgggaagcgt ggcgctttct catagctcac gctgtaggta tctcagttcg   9600
gtgtaggtcg ttcgctccaa gctgggctgt gtgcacgaac cccccgttca gcccgaccgc   9660
tgcgccttat ccggtaacta tcgtcttgag tccaacccgg taagacacga cttatcgcca   9720
ctggcagcag ccactggtaa caggattagc agagcgaggt atgtaggcgg tgctacagag   9780
ttcttgaagt ggtggcctaa ctacggctac actagaagaa cagtatttgg tatctgcgct   9840
ctgctgaagc cagttacctt cggaaaaaga gttggtagct cttgatccgg caaacaaacc   9900
accgctggta gcggtggttt ttttgtttgc aagcagcaga ttacgcgcag aaaaaaagga   9960
tctcaagaag atcctttgat cttttctacg gggtctgacg ctcagtggaa cgaaaactca  10020
cgttaaggga ttttggtcat gagattatca aaaaggatct tcacctagat ccttttaaat  10080
taaaaatgaa gttttaaatc aatctaaagt atatatgagt aaacttggtc tgacagttac  10140
caatgcttaa tcagtgaggc acctatctca gcgatctgtc tatttcgttc atccatagtt  10200
gcctgactcc tgcaaaccac gttgtgtctc aaaatctctg atgttacatt gcacaagata  10260
aaaatatatc atcatgaaca ataaaactgt ctgcttacat aaacagtaat acaaggggtg  10320
ttatgagcca tattcaacgg gaaacgtctt gctcgaggcc gcgattaaat tccaacatgg  10380
atgctgattt atatgggtat aaatgggctc gcgataatgt cgggcaatca ggtgcgacaa  10440
tctatcgatt gtatgggaag cccgatgcgc cagagttgtt tctgaaacat ggcaaaggta  10500
gcgttgccaa tgatgttaca gatgagatgg tcagactaaa ctggctgacg gaatttatgc  10560
ctcttccgac catcaagcat tttatccgta ctcctgatga tgcatggtta ctcaccactg  10620
cgatccccgg gaaaacagca ttccaggtat tagaagaata tcctgattca ggtgaaaata  10680
ttgttgatgc gctggcagtg ttcctgcgcc ggttgcattc gattcctgtt tgtaattgtc  10740
```

cttttaacag cgatcgcgta tttcgtctcg ctcaggcgca atcacgaatg aataacggtt 10800
tggttgatgc gagtgatttt gatgacgagc gtaatggctg gcctgttgaa caagtctgga 10860
aagaaatgca taagcttttg ccattctcac cggattcagt cgtcactcat ggtgatttct 10920
cacttgataa ccttattttt gacgagggga aattaatagg ttgtattgat gttggacgag 10980
tcggaatcgc agaccgatac caggatcttg ccatcctatg gaactgcctc ggtgagtttt 11040
ctccttcatt acagaaacgg ctttttcaaa aatatggtat tgataatcct gatatgaata 11100
aattgcagtt tcatttgatg ctcgatgagt ttttctaagg gcggcctgcc accataccca 11160
cgccgaaaca agcgctcatg agcccgaagt ggcgagcccg atcttcccca tcggtgatgt 11220
cggcgatata ggcgccagca accgcacctg tggcgccggt gatgagggcg cgccaagtcg 11280
acgtccggca gtc 11293

<210> SEQ ID NO 7
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 7
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctccggg ctgtaattag 1080
cgcttggttt aatgacggct tgtttctttt ctgtggctgc gtgaaagcct tgaggggctc 1140
cgggagctag agcctctgct aaccatgttc atgccttctt ctttttccta cagctcctgg 1200
gcaacgtgct ggttattgtg ctgtctcatc attttggcaa agaattcctc gaagatccga 1260
agggaaagtc ttccacgact gtgggatccg ttcgaagata tcaccggttg agccaccatg 1320
gaattcagca gccccagcag agaggaatgc cccaagcctc tgagccgggt gtcaatcatg 1380
gccggatctc tgacaggact gctgctgctt caggccgtgt cttgggcttc tggcgctaga 1440

-continued

```
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg   3840
```

-continued

```
gtgaacatat tgactgaatt ccctgcaggt tggccactcc ctctctgcgc gctcgctcgc   3900
tcactgaggc cgcccgggca aagcccgggc gtcgggcgac ctttggtcgc ccggcctcag   3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
```

-continued

```
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctcccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
```

```
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgtttttcca taggctccgc ccccctgacg agcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
cgaccgctgc gccttatccg gtaactatcg tcttgagtcc aacccggtaa gacacgactt   9120
atcgccactg gcagcagcca ctggtaacag gattagcaga gcgaggtatg taggcggtgc   9180
tacagagttc ttgaagtggt ggcctaacta cggctacact agaagaacag tatttggtat   9240
ctgcgctctg ctgaagccag ttaccttcgg aaaaagagtt ggtagctctt gatccggcaa   9300
acaaaccacc gctggtagcg gtggtttttt tgtttgcaag cagcagatta cgcgcagaaa   9360
aaaaggatct caagaagatc ctttgatctt ttctacgggg tctgacgctc agtggaacga   9420
aaactcacgt taagggattt tggtcatgag attatcaaaa aggatcttca cctagatcct   9480
tttaaattaa aaatgaagtt ttaaatcaat ctaaagtata tatgagtaaa cttggtctga   9540
cagttaccaa tgcttaatca gtgaggcacc tatctcagcg atctgtctat ttcgttcatc   9600
catagttgcc tgactcctgc aaaccacgtt gtgtctcaaa atctctgatg ttacattgca   9660
caagataaaa atatatcatc atgaacaata aaactgtctg cttacataaa cagtaataca   9720
aggggtgtta tgagccatat tcaacgggaa acgtcttgct cgaggccgcg attaaattcc   9780
aacatggatg ctgatttata tgggtataaa tgggctcgcg ataatgtcgg gcaatcaggt   9840
gcgacaatct atcgattgta tgggaagccc gatgcgccag agttgtttct gaaacatggc   9900
aaaggtagcg ttgccaatga tgttacagat gagatggtca gactaaactg gctgacggaa   9960
tttatgcctc ttccgaccat caagcatttt atccgtactc ctgatgatgc atggttactc  10020
accactgcga tccccgggaa aacagcattc caggtattag aagaatatcc tgattcaggt  10080
gaaaatattg ttgatgcgct ggcagtgttc ctgcgccggt tgcattcgat tcctgtttgt  10140
aattgtcctt ttaacagcga tcgcgtattt cgtctcgctc aggcgcaatc acgaatgaat  10200
aacggtttgg ttgatgcgag tgattttgat gacgagcgta atggctggcc tgttgaacaa  10260
gtctggaaag aaatgcataa gcttttgcca ttctcaccgg attcagtcgt cactcatggt  10320
gatttctcac ttgataacct tatttttgac gaggggaaat taataggttg tattgatgtt  10380
ggacgagtcg gaatcgcaga ccgataccag gatcttgcca tcctatggaa ctgcctcggt  10440
gagttttctc cttcattaca gaaacggctt tttcaaaaat atggtattga taatcctgat  10500
atgaataaat tgcagtttca tttgatgctc gatgagtttt tctaagggcg gcctgccacc  10560
atacccacgc cgaaacaagc gctcatgagc ccgaagtggc gagcccgatc ttccccatcg  10620
gtgatgtcgg cgatataggc gccagcaacc gcacctgtgg cgccggtgat gagggcgcgc  10680
caagtcgacg tccggcagtc                                                 10700
```

<210> SEQ ID NO 8
<211> LENGTH: 10700
<212> TYPE: DNA
<213> ORGANISM: Artificial Sequence
<220> FEATURE:

<223> OTHER INFORMATION: Synthetic polynucleotide

<400> SEQUENCE: 8
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactatt agatctgatg gccgcgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780
gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctccggg ctgtaattag 1080
cgcttggttt aatgacggct tgtttctttt ctgtggctgc gtgaaagcct tgaggggctc 1140
cgggagctag agcctctgct aaccatgttc atgccttctt cttttcccta cagctcctgg 1200
gcaacgtgct ggttattgtg ctgtctcatc attttggcaa agaattcctc gaagatccga 1260
agggaaagtc ttccacgact gtgggatccg ttcgaagata tcaccggttg agccaccatg 1320
gaattcagca gccccagcag agaggaatgc cccaagcctc tgagccgggt gtcaatcatg 1380
gccggatctc tgacaggact gctgctgctt caggccgtgt cttgggcttc tggcgctaga 1440
ccttgcatcc ccaagagctt cggctacagc agcgtcgtgt gcgtgtgcaa tgccacctac 1500
tgcgacagct tcgaccctcc tacctttcct gctctgggca ccttcagcag atacgagagc 1560
accagatccg gcagacggat ggaactgagc atgggaccca tccaggccaa tcacacaggc 1620
actggcctgc tgctgacact gcagcctgag cagaaattcc agaaagtgaa aggcttcggc 1680
ggagccatga cagatgccgc cgctctgaat atcctggctc tgtctccacc agctcagaac 1740
ctgctgctca agagctactt cagcgaggaa ggcatcggct acaacatcat cagagtgccc 1800
atggccagct gcgacttcag catcaggacc tacacctacg ccgacacacc cgacgatttc 1860
cagctgcaca acttcagcct gcctgaagag gacaccaagc tgaagatccc tctgatccac 1920
agagccctgc agctggcaca aagacccgtg tcactgctgg cctctccatg gacatctccc 1980
acctggctga aaacaaatgg cgccgtgaat ggcaagggca gcctgaaagg ccaacctggc 2040
gacatctacc accagacctg ggccagatac ttcgtgaagt tcctggacgc ctatgccgag 2100
cacaagctgc agttttgggc cgtgacagcc gagaacgaac cttctgctgg actgctgagc 2160
ggctacccct ttcagtgcct gggctttaca cccgagcacc agcgggactt tatcgcccgt 2220
gatctgggac ccacactggc caatagcacc caccataatg tgcggctgct gatgctggac 2280
gaccagagac tgcttctgcc ccactgggct aaagtggtgc tgacagatcc tgaggccgcc 2340
aaatacgtgc acggaatcgc cgtgcactgg tatctggact ttctggcccc tgccaaggcc 2400
acactgggag agacacacag actgttcccc aacaccatgc tgttcgccag cgaagcctgt 2460
gtgggcagca agttttggga acagagcgtg cggctcggca gctgggatag aggcatgcag 2520
tacagccaca gcatcatcac caacctgctg taccacgtcg tcggctggac cgactggaat 2580
ctggccctga atcctgaagg cggccctaac tgggtccgaa acttcgtgga cagccccatc 2640
atcgtggaca tcaccaagga caccttctac aagcagccca tgttctacca cctgggacac 2700
ttcagcaagt tcatccccga gggctctcag cgcgttggac tggtggcttc ccagaagaac 2760
gatctggacg ccgtggctct gatgcaccct gatggatctg ctgtggtggt ggtcctgaac 2820
cgcagcagca aagatgtgcc cctgaccatc aaggatcccg ccgtgggatt cctggaaaca 2880
atcagccctg gctactccat ccacacctac ctgtggcgta gacagtgaca attgttaatt 2940
aagtttaaac cctcgaggcc gcaagcttat cgataatcaa cctctggatt acaaaatttg 3000
tgaaagattg actggtattc ttaactatgt tgctcctttt acgctatgtg gatacgctgc 3060
tttaatgcct ttgtatcatg ctattgcttc ccgtatggct ttcattttct cctccttgta 3120
taaatcctgg ttgctgtctc tttatgagga gttgtggccc gttgtcaggc aacgtggcgt 3180
ggtgtgcact gtgtttgctg acgcaacccc cactggttgg ggcattgcca ccacctgtca 3240
gctcctttcc gggactttcg ctttccccct ccctattgcc acggcggaac tcatcgccgc 3300
ctgccttgcc cgctgctgga caggggctcg gctgttgggc actgacaatt ccgtggtgtt 3360
gtcggggaaa tcatcgtcct ttccttggct gctcgcctgt gttgccacct ggattctgcg 3420
cgggacgtcc ttctgctacg tcccttcggc cctcaatcca gcggaccttc cttcccgcgg 3480
cctgctgccg gctctgcggc ctcttccgcg tcttcgcctt cgccctcaga cgagtcggat 3540
ctccctttgg gccgcctccc cgcatcgata ccgtcgacta gagctcgctg atcagcctcg 3600
actgtgcctt ctagttgcca gccatctgtt gtttgcccct cccccgtgcc ttccttgacc 3660
ctggaaggtg ccactcccac tgtcctttcc taataaaatg aggaaattgc atcgcattgt 3720
ctgagtaggt gtcattctat tctggggggt ggggtggggc aggacagcaa gggggaggat 3780
tgggaagaca atagcaggca tgctggggag agatccacga taacaaacag ctttttttggg 3840
gtgaacatat tgactgaatt ccctgcaggt tggccactcc ctctctgcgc gctcgctcgc 3900
tcactgaggc cgcccgggca aagcccgggc gtcgggcgac ctttggtcgc ccggcctcag 3960
tgagcgagcg agcgcgcaga gagggagtgg ccaactccat cactaggggt tcctgcggcc 4020
gctcgtacgg tctcgaggaa ttcctgcagg ataacttgcc aacctcattc taaaatgtat 4080
atagaagccc aaaagacaat aacaaaaata ttcttgtaga acaaaatggg aaagaatgtt 4140
ccactaaata tcaagattta gagcaaagca tgagatgtgt ggggatagac agtgaggctg 4200
ataaaataga gtagagctca gaaacagacc cattgatata tgtaagtgac ctatgaaaaa 4260
aatatggcat tttacaatgg gaaaatgatg gtctttttct tttttagaaa aacagggaaa 4320
tatatttata tgtaaaaaat aaaagggaac ccatatgtca taccatacac acaaaaaaat 4380
tccagtgaat tataagtcta aatggagaag gcaaaacttt aaatctttta gaaaataata 4440
tagaagcatg cagaccagcc tggccaacat gatgaaaccc tctctactaa taataaaatc 4500
agtagaacta ctcaggacta ctttgagtgg gaagtccttt tctatgaaga cttctttggc 4560
caaaattagg ctctaaatgc aaggagatag tgcatcatgc ctggctgcac ttactgataa 4620

-continued

```
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc  5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agatttaca caagatggtc tgtaatttca cagttagttt tatcccatta ggtatgaaag    6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
```

```
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctcccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgtttttcca taggctccgc ccccctgacg agcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
cgaccgctgc gccttatccg gtaactatcg tcttgagtcc aacccggtaa gacacgactt   9120
atcgccactg gcagcagcca ctggtaacag gattagcaga gcgaggtatg taggcggtgc   9180
tacagagttc ttgaagtggt ggcctaacta cggctacact agaagaacag tatttggtat   9240
ctgcgctctg ctgaagccag ttaccttcgg aaaaagagtt ggtagctctt gatccggcaa   9300
acaaaccacc gctggtagcg gtggtttttt tgtttgcaag cagcagatta cgcgcagaaa   9360
```

```
aaaaggatct caagaagatc ctttgatctt ttctacgggg tctgacgctc agtggaacga   9420

aaactcacgt taagggattt tggtcatgag attatcaaaa aggatcttca cctagatcct   9480

tttaaattaa aaatgaagtt ttaaatcaat ctaaagtata tatgagtaaa cttggtctga   9540

cagttaccaa tgcttaatca gtgaggcacc tatctcagcg atctgtctat ttcgttcatc   9600

catagttgcc tgactcctgc aaaccacgtt gtgtctcaaa atctctgatg ttacattgca   9660

caagataaaa atatatcatc atgaacaata aaactgtctg cttacataaa cagtaataca   9720

aggggtgtta tgagccatat tcaacgggaa acgtcttgct cgaggccgcg attaaattcc   9780

aacatggatg ctgatttata tgggtataaa tgggctcgcg ataatgtcgg gcaatcaggt   9840

gcgacaatct atcgattgta tgggaagccc gatgcgccag agttgtttct gaaacatggc   9900

aaaggtagcg ttgccaatga tgttacagat gagatggtca gactaaactg gctgacggaa   9960

tttatgcctc ttccgaccat caagcatttt atccgtactc ctgatgatgc atggttactc  10020

accactgcga tccccgggaa aacagcattc caggtattag aagaatatcc tgattcaggt  10080

gaaaatattg ttgatgcgct ggcagtgttc ctgcgccggt tgcattcgat tcctgtttgt  10140

aattgtcctt ttaacagcga tcgcgtattt cgtctcgctc aggcgcaatc acgaatgaat  10200

aacggtttgg ttgatgcgag tgattttgat gacgagcgta atggctggcc tgttgaacaa  10260

gtctggaaag aaatgcataa gcttttgcca ttctcaccgg attcagtcgt cactcatggt  10320

gatttctcac ttgataacct tatttttgac gaggggaaat taataggttg tattgatgtt  10380

ggacgagtcg gaatcgcaga ccgataccag gatcttgcca tcctatggaa ctgcctcggt  10440

gagttttctc cttcattaca gaaacggctt tttcaaaaat atggtattga taatcctgat  10500

atgaataaat tgcagtttca tttgatgctc gatgagtttt tctaagggcg gcctgccacc  10560

atacccacgc cgaaacaagc gctcatgagc ccgaagtggc gagcccgatc ttccccatcg  10620

gtgatgtcgg cgatataggc gccagcaacc gcacctgtgg cgccggtgat gagggcgcgc  10680

caagtcgacg tccggcagtc                                              10700
```

<210> SEQ ID NO 9
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 9

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

ctagttatta atagtaatca attacggggt cattagttca tagcccatat atggagttcc    360

gcgttacata acttacggta aatggcccgc ctggctgacc gcccaacgac ccccgcccat    420

tgacgtcaat aatgacgtat gttcccatag taacgccaat agggactttc cattgacgtc    480

aatgggtgga gtatttacgg taaactgccc acttggcagt acatcaagtg tatcatatgc    540

caagtacgcc ccctattgac gtcaatgacg gtaaatggcc cgcctggcat tatgcccagt    600

acatgacctt atgggacttt cctacttggc agtacatcta cgtattagtc atcgctatta    660

ccatggtcga ggtgagcccc acgttctgct tcactctccc catctccccc ccctccccac    720
```

-continued

```
ccccaatttt gtatttattt attttttaat tattttgtgc agcgatgggg gcgggggggg    780
gggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctccggg ctgtaattag   1080
cgcttggttt aatgacggct tgtttctttt ctgtggctgc gtgaaagcct tgaggggctc   1140
cgggagctag agcctctgct aaccatgttc atgccttctt cttttcccta cagctcctgg   1200
gcaacgtgct ggttattgtg ctgtctcatc attttggcaa agaattcctc gaagatccga   1260
agggaaagtc ttccacgact gtgggatccg ttcgaagata tcaccggttg agccaccatg   1320
gaattcagca gccccagcag agaggaatgc cccaagcctc tgagccgggt gtcaatcatg   1380
gccggatctc tgacaggact gctgctgctt caggccgtgt cttgggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
```

-continued

```
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg   3840
gtgaacatat tgactgaatt ccctgcaggt tggccactcc ctctctgcgc gctcgctcgc   3900
tcactgaggc cgcccgggca aagcccgggc gtcgggcgac ctttggtcgc ccggcctcag   3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
```

```
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctcccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
```

aagagagcaa ctgaatcagg aagcagagtt ttgaacatat cagaagttag gaatctgcat 7860
cagagacaaa tgcagtcatg gttgtttgct gcataccagc cctaatcatt agaagcctca 7920
tggacttcaa acatcattcc ctctgacaag atgctctagc ctaactccat gagataaaat 7980
aaatctgcct ttcagagcca aagaagagtc caccagcttc ttctcagtgt gaacaagagc 8040
tccagtcagg ttagtcagtc cagtgcagta gaggagacca gtctgcatcc tctaattttc 8100
aaaggcaaga agatttgttt accctggaca ccaggcacaa gtgaggtcac agagctctta 8160
gatatgcagt cctcatgagt gaggagacta aagcgcatgc catcaagact tcagtgtaga 8220
gaaaacctcc aaaaaagcct cctcactact tctggaatag ctcagaggcc gaggcggcct 8280
cggcctctgc ataaataaaa aaaattagtc agccatgggg cggagaatgg gcggaactgg 8340
gcggagttag gggcgggatg ggcggagtta ggggcgggac tatggttgct gactaattga 8400
gatgcatgct ttgcatactt ctgcctgctg gggagcctgg ggactttcca cacctggttg 8460
ctgactaatt gagatgcatg ctttgcatac ttctgcctgc tggggagcct ggggactttc 8520
cacaccctaa ctgacacaca ttccacagct gcattaatga atcggccaac gcgcggggag 8580
aggcggtttg cgtattgggc gctcttccgc ttcctcgctc actgactcgc tgcgctcggt 8640
cgttcggctg cggcgagcgg tatcagctca ctcaaaggcg gtaatacggt tatccacaga 8700
atcaggggat aacgcaggaa agaacatgtg agcaaaaggc cagcaaaagg ccaggaaccg 8760
taaaaaggcc gcgttgctgg cgtttttcca taggctccgc ccccctgacg agcatcacaa 8820
aaatcgacgc tcaagtcaga ggtggcgaaa cccgacagga ctataaagat accaggcgtt 8880
tccccctgga agctccctcg tgcgctctcc tgttccgacc ctgccgctta ccggatacct 8940
gtccgccttt ctcccttcgg gaagcgtggc gctttctcat agctcacgct gtaggtatct 9000
cagttcggtg taggtcgttc gctccaagct gggctgtgtg cacgaacccc ccgttcagcc 9060
cgaccgctgc gccttatccg gtaactatcg tcttgagtcc aacccggtaa gacacgactt 9120
atcgccactg gcagcagcca ctggtaacag gattagcaga gcgaggtatg taggcggtgc 9180
tacagagttc ttgaagtggt ggcctaacta cggctacact agaagaacag tatttggtat 9240
ctgcgctctg ctgaagccag ttaccttcgg aaaaagagtt ggtagctctt gatccggcaa 9300
acaaaccacc gctggtagcg gtggtttttt tgtttgcaag cagcagatta cgcgcagaaa 9360
aaaaggatct caagaagatc ctttgatctt ttctacgggg tctgacgctc agtggaacga 9420
aaactcacgt taagggattt tggtcatgag attatcaaaa aggatcttca cctagatcct 9480
tttaaattaa aaatgaagtt ttaaatcaat ctaaagtata tatgagtaaa cttggtctga 9540
cagttaccaa tgcttaatca gtgaggcacc tatctcagcg atctgtctat ttcgttcatc 9600
catagttgcc tgactcctgc aaaccacgtt gtgtctcaaa atctctgatg ttacattgca 9660
caagataaaa atatatcatc atgaacaata aaactgtctg cttacataaa cagtaataca 9720
aggggtgtta tgagccatat tcaacgggaa acgtcttgct cgaggccgcg attaaattcc 9780
aacatggatg ctgatttata tgggtataaa tgggctcgcg ataatgtcgg gcaatcaggt 9840
gcgacaatct atcgattgta tgggaagccc gatgcgccag agttgtttct gaaacatggc 9900
aaaggtagcg ttgccaatga tgttacagat gagatggtca gactaaactg gctgacggaa 9960
tttatgcctc ttccgaccat caagcatttt atccgtactc ctgatgatgc atggttactc 10020
accactgcga tccccgggaa aacagcattc caggtattag aagaatatcc tgattcaggt 10080
gaaaatattg ttgatgcgct ggcagtgttc ctgcgccggt tgcattcgat tcctgtttgt 10140
aattgtcctt ttaacagcga tcgcgtattt cgtctcgctc aggcgcaatc acgaatgaat 10200

-continued aacggtttgg ttgatgcgag tgattttgat gacgagcgta atggctggcc tgttgaacaa 10260
gtctggaaag aaatgcataa gcttttgcca ttctcaccgg attcagtcgt cactcatggt 10320
gatttctcac ttgataacct tatttttgac gaggggaaat taataggttg tattgatgtt 10380
ggacgagtcg gaatcgcaga ccgataccag gatcttgcca tcctatggaa ctgcctcggt 10440
gagttttctc cttcattaca gaaacggctt tttcaaaaat atggtattga taatcctgat 10500
atgaataaat tgcagtttca tttgatgctc gatgagtttt tctaagggcg gcctgccacc 10560
atacccacgc cgaaacaagc gctcatgagc ccgaagtggc gagcccgatc ttccccatcg 10620
gtgatgtcgg cgatataggc gccagcaacc gcacctgtgg cgccggtgat gagggcgcgc 10680
caagtcgacg tccggcagtc 10700

<210> SEQ ID NO 10
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 10
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctccggg ctgtaattag 1080
cgcttggttt aatgacggct tgtttctttt ctgtggctgc gtgaaagcct tgaggggctc 1140
cgggagctag agcctctgct aaccatgttc atgccttctt cttttcccta cagctcctgg 1200
gcaacgtgct ggttattgtg ctgtctcatc attttggcaa agaattcctc gaagatccga 1260
agggaaagtc ttccacgact gtgggatccg ttcgaagata tcaccggttg agccaccatg 1320
gaattcagca gccccagcag agaggaatgc cccaagcctc tgagccgggt gtcaatcatg 1380
gccggatctc tgacaggact gctgctgctt caggccgtgt cttgggcttc tggcgctaga 1440
ccttgcatcc ccaagagctt cggctacagc agcgtcgtgt gcgtgtgcaa tgccacctac 1500

-continued

```
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg   3840
gtgaacatat tgactgaatt ccctgcagga ggaaccccta gtgatggagt tggccactcc   3900
```

```
ctctctgcgc gctcgctcgc tcactgaggc cgcccgggca aagcccgggc gtcgggcgac   3960
ctttggtcgc ccggcctcag tgagcgagcg agcgcgcaga gagggagtgg ccaagcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtcttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc  5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
```

```
agccctaatt aggcatcatg acttcagcct gaccttccat gctcagaagc agtgctaatc    6300
cacttcagat gagctgctct atgcaacaca ggcagagcct acaaaccttt gcaccagagc    6360
cctccacata tcagtgtttg ttcatactca cttcaacagc aaatgtgact gctgagatta    6420
agattttaca caagatggtc tgtaatttca cagttagttt tatcccatta ggtatgaaag    6480
aattagcata attcccctta aacatgaatg aatcttagat tttttaataa atagttttgg    6540
aagtaaagac agagacatca ggagcacaag gaatagcctg agaggacaaa cagaacaaga    6600
aagagtctgg aaatacacag gatgttcttg gcctcctcaa agcaagtgca agcagatagt    6660
accagcagcc ccaggctatc agagcccagt gaagagaagt accatgaaag ccacagctct    6720
aaccaccctg ttccagagtg acagacagtc cccaagacaa gccagcctga gccagagaga    6780
gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctcccccc gctctgatgg ctggagccca atccctacac    7500
agactcctgc tgtatgtgtt ttcctttcac tctgagccac agccagaggg caggcattca    7560
gtctcctctt caggctgggg ctggggcact gagaactcac ccaacacctt gctctcactc    7620
cttctgcaaa acaagaaaga gctttgtgct gcagtagcca tgaagaatga aaggaaggct    7680
ttaactaaaa aatgtcagag attattttca accccttact gtggatcacc agcaaggagg    7740
aaacacaaca cagagacatt ttttcccctc aaattatcaa aagaatcact gcatttgtta    7800
aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca aagaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
```

cgttcggctg cggcgagcgg tatcagctca ctcaaaggcg gtaatacggt tatccacaga 8700
atcaggggat aacgcaggaa agaacatgtg agcaaaaggc cagcaaaagg ccaggaaccg 8760
taaaaaggcc gcgttgctgg cgtttttcca taggctccgc ccccctgacg agcatcacaa 8820
aaatcgacgc tcaagtcaga ggtggcgaaa cccgacagga ctataaagat accaggcgtt 8880
tccccctgga agctccctcg tgcgctctcc tgttccgacc ctgccgctta ccggatacct 8940
gtccgccttt ctcccttcgg gaagcgtggc gctttctcat agctcacgct gtaggtatct 9000
cagttcggtg taggtcgttc gctccaagct gggctgtgtg cacgaacccc ccgttcagcc 9060
cgaccgctgc gccttatccg gtaactatcg tcttgagtcc aacccggtaa gacacgactt 9120
atcgccactg gcagcagcca ctggtaacag gattagcaga gcgaggtatg taggcggtgc 9180
tacagagttc ttgaagtggt ggcctaacta cggctacact agaagaacag tatttggtat 9240
ctgcgctctg ctgaagccag ttaccttcgg aaaaagagtt ggtagctctt gatccggcaa 9300
acaaaccacc gctggtagcg gtggtttttt tgtttgcaag cagcagatta cgcgcagaaa 9360
aaaaggatct caagaagatc ctttgatctt ttctacgggg tctgacgctc agtggaacga 9420
aaactcacgt taagggattt tggtcatgag attatcaaaa aggatcttca cctagatcct 9480
tttaaattaa aaatgaagtt ttaaatcaat ctaaagtata tatgagtaaa cttggtctga 9540
cagttaccaa tgcttaatca gtgaggcacc tatctcagcg atctgtctat ttcgttcatc 9600
catagttgcc tgactcctgc aaaccacgtt gtgtctcaaa atctctgatg ttacattgca 9660
caagataaaa atatatcatc atgaacaata aaactgtctg cttacataaa cagtaataca 9720
aggggtgtta tgagccatat tcaacgggaa acgtcttgct cgaggccgcg attaaattcc 9780
aacatggatg ctgatttata tgggtataaa tgggctcgcg ataatgtcgg gcaatcaggt 9840
gcgacaatct atcgattgta tgggaagccc gatgcgccag agttgtttct gaaacatggc 9900
aaaggtagcg ttgccaatga tgttacagat gagatggtca gactaaactg gctgacggaa 9960
tttatgcctc ttccgaccat caagcatttt atccgtactc ctgatgatgc atggttactc 10020
accactgcga tccccgggaa aacagcattc caggtattag aagaatatcc tgattcaggt 10080
gaaaatattg ttgatgcgct ggcagtgttc ctgcgccggt tgcattcgat tcctgtttgt 10140
aattgtcctt ttaacagcga tcgcgtattt cgtctcgctc aggcgcaatc acgaatgaat 10200
aacggtttgg ttgatgcgag tgattttgat gacgagcgta atggctggcc tgttgaacaa 10260
gtctggaaag aaatgcataa gcttttgcca ttctcaccgg attcagtcgt cactcatggt 10320
gatttctcac ttgataacct tatttttgac gaggggaaat taataggttg tattgatgtt 10380
ggacgagtcg gaatcgcaga ccgataccag gatcttgcca tcctatggaa ctgcctcggt 10440
gagttttctc cttcattaca gaaacggctt tttcaaaaat atggtattga taatcctgat 10500
atgaataaat tgcagtttca tttgatgctc gatgagtttt tctaagggcg gcctgccacc 10560
atacccacgc cgaaacaagc gctcatgagc ccgaagtggc gagcccgatc ttccccatcg 10620
gtgatgtcgg cgatataggc gccagcaacc gcacctgtgg cgccggtgat gagggcgcgc 10680
caagtcgacg tccggcagtc 10700

<210> SEQ ID NO 11
<211> LENGTH: 11188
<212> TYPE: DNA
<213> ORGANISM: Artificial Sequence
<220> FEATURE:
<223> OTHER INFORMATION: Synthetic polynucleotide

<400> SEQUENCE: 11
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactatt agatctgatg gccgcgctag ctctgggtat ttaagcccga gtgagcacgc 180
agggtctcca ttttgaagcg ggaggttacg cgttcgtcga ctactagtgg gtaccagagc 240
gtggtgactg agatgttttc taggaaacac aaaagataca aaaaagaaca cgtggaagga 300
tagccaaaaa ggggggctgc ccccatttcc tgcaccccgc tgcgatggct ggcaccattt 360
ggaagacttc gagatacact gttgagcgca gtaagacaac agtgtatctc gaagtcttcc 420
agatggggcc agccggtcca ctctgtatcc aggccagttc tgcaaggcgt tcgaggacca 480
ccccctccc ctcgccacca gggtggtctc atacagaact tataagattc ccaaatccaa 540
agacatttca cgtttatggt gatttcccag aacacatagc gacatgcaaa tattgcaggg 600
cgccactccc ctgtccctca cagccatctt cctgccaggg cgcacgcgcg ctgggtgttc 660
ccgcctagtg acactgggcc cgcgattcct tggagcgggt tgatgacgtc agcgtttccc 720
atggtgaatc cctaggttct agaaccggtg acgtctccca tggtgaagct tggatctgaa 780
ttcggtacct agttattaat agtaatcaat tacggggtca ttagttcata gcccatatat 840
ggagttccgc gttacataac ttacggtaaa tggcccgcct ggctgaccgc ccaacgaccc 900
ccgcccattg acgtcaataa tgacgtatgt tcccatagta acgccaatag ggactttcca 960
ttgacgtcaa tgggtggagt atttacggta aactgcccac ttggcagtac atcaagtgta 1020
tcatatgcca agtacgcccc ctattgacgt caatgacggt aaatggcccg cctggcatta 1080
tgcccagtac atgaccttat gggactttcc tacttggcag tacatctacg tattagtcat 1140
cgctattacc atggtcgagg tgagccccac gttctgcttc actctcccca tctccccccc 1200
ctccccaccc ccaattttgt atttatttat tttttaatta ttttgtgcag cgatgggggc 1260
gggggggggg ggggggcgcg cgccaggcgg ggcggggcgg ggcgaggggc ggggcggggc 1320
gaggcggaga ggtgcggcgg cagccaatca gagcggcgcg ctccgaaagt ttccttttat 1380
ggcgaggcgg cggcggcggc ggccctataa aaagcgaagc gcgcggcggg cgggagtcgc 1440
tgcgacgctg ccttcgcccc gtgccccgct ccgccgccgc ctcgcgccgc ccgccccggc 1500
tctgactgac cgcgttactc ccacaggtga gcgggcggga cggcccttct cctccgggct 1560
gtaattagcg cttggtttaa tgacggcttg tttcttttct gtggctgcgt gaaagccttg 1620
aggggctccg ggagctagag cctctgctaa ccatgttcat gccttcttct ttttcctaca 1680
gctcctgggc aacgtgctgg ttattgtgct gtctcatcat tttggcaaag aattcctcga 1740
agatccgaag ggaaagtctt ccacgactgt gggatccgtt cgaagatatc accggttgag 1800
ccaccatgga attcagcagc cccagcagag aggaatgccc caagcctctg agccgggtgt 1860
caatcatggc cggatctctg acaggactgc tgctgcttca ggccgtgtct tgggcttctg 1920
gcgctagacc ttgcatcccc aagagcttcg gctacagcag cgtcgtgtgc gtgtgcaatg 1980
ccacctactg cgacagcttc gaccctccta cctttcctgc tctgggcacc ttcagcagat 2040
acgagagcac cagatccggc agacggatgg aactgagcat gggacccatc caggccaatc 2100
acacaggcac tggcctgctg ctgacactgc agcctgagca gaaattccag aaagtgaaag 2160
gcttcggcgg agccatgaca gatgccgccg ctctgaatat cctggctctg tctccaccag 2220
ctcagaacct gctgctcaag agctacttca gcgaggaagg catcggctac aacatcatca 2280
gagtgcccat ggccagctgc gacttcagca tcaggaccta cacctacgcc gacacacccg 2340
acgatttcca gctgcacaac ttcagcctgc ctgaagagga caccaagctg aagatccctc 2400
tgatccacag agccctgcag ctggcacaaa gacccgtgtc actgctggcc tctccatgga 2460
catctcccac ctggctgaaa acaaatggcg ccgtgaatgg caagggcagc ctgaaaggcc 2520
aacctggcga catctaccac cagacctggg ccagatactt cgtgaagttc ctggacgcct 2580
atgccgagca caagctgcag ttttgggccg tgacagccga gaacgaacct tctgctggac 2640
tgctgagcgg ctaccccttt cagtgcctgg gctttacacc cgagcaccag cgggacttta 2700
tcgcccgtga tctgggaccc acactggcca atagcaccca ccataatgtg cggctgctga 2760
tgctggacga ccagagactg cttctgcccc actgggctaa agtggtgctg acagatcctg 2820
aggccgccaa atacgtgcac ggaatcgccg tgcactggta tctggacttt ctggcccctg 2880
ccaaggccac actgggagag acacacagac tgttccccaa caccatgctg ttcgccagcg 2940
aagcctgtgt gggcagcaag ttttgggaac agagcgtgcg gctcggcagc tgggatagag 3000
gcatgcagta cagccacagc atcatcacca acctgctgta ccacgtcgtc ggctggaccg 3060
actggaatct ggccctgaat cctgaaggcg gccctaactg ggtccgaaac ttcgtggaca 3120
gccccatcat cgtggacatc accaaggaca ccttctacaa gcagcccatg ttctaccacc 3180
tgggacactt cagcaagttc atccccgagg gctctcagcg cgttggactg gtggcttccc 3240
agaagaacga tctggacgcc gtggctctga tgcaccctga tggatctgct gtggtggtgg 3300
tcctgaaccg cagcagcaaa gatgtgcccc tgaccatcaa ggatcccgcc gtgggattcc 3360
tggaaacaat cagccctggc tactccatcc acacctacct gtggcgtaga cagtgacaat 3420
tgttaattaa gtttaaaccc tcgaggccgc aagcttatcg ataatcaacc tctggattac 3480
aaaatttgtg aaagattgac tggtattctt aactatgttg ctccttttac gctatgtgga 3540
tacgctgctt taatgccttt gtatcatgct attgcttccc gtatggcttt cattttctcc 3600
tccttgtata aatcctggtt gctgtctctt tatgaggagt tgtggcccgt tgtcaggcaa 3660
cgtggcgtgg tgtgcactgt gtttgctgac gcaaccccca ctggttgggg cattgccacc 3720
acctgtcagc tcctttccgg gactttcgct ttccccctcc ctattgccac ggcggaactc 3780
atcgccgcct gccttgcccg ctgctggaca ggggctcggc tgttgggcac tgacaattcc 3840
gtggtgttgt cggggaaatc atcgtccttt ccttggctgc tcgcctgtgt tgccacctgg 3900
attctgcgcg ggacgtcctt ctgctacgtc ccttcggccc tcaatccagc ggaccttcct 3960
tcccgcggcc tgctgccggc tctgcggcct cttccgcgtc ttcgccttcg ccctcagacg 4020
agtcggatct ccctttgggc cgcctccccg catcgatacc gtcgactaga gctcgctgat 4080
cagcctcgac tgtgccttct agttgccagc catctgttgt ttgcccctcc cccgtgcctt 4140
ccttgaccct ggaaggtgcc actcccactg tcctttccta ataaaatgag gaaattgcat 4200
cgcattgtct gagtaggtgt cattctattc tggggggtgg ggtggggcag gacagcaagg 4260
gggaggattg ggaagacaat agcaggcatg ctggggagag atccacgata acaaacagct 4320
tttttggggt gaacatattg actgaattcc ctgcaggttg gccactccct ctctgcgcgc 4380
tcgctcgctc actgaggccg cccgggcaaa gcccgggcgt cgggcgacct ttggtcgccc 4440
ggcctcagtg agcgagcgag cgcgcagaga gggagtggcc aactccatca ctaggggttc 4500
ctgcggccgc tcgtacggtc tcgaggaatt cctgcaggat aacttgccaa cctcattcta 4560
aaatgtatat agaagcccaa aagacaataa caaaaatatt cttgtagaac aaaatgggaa 4620
agaatgttcc actaaatatc aagatttaga gcaaagcatg agatgtgtgg ggatagacag 4680

```
tgaggctgat aaaatagagt agagctcaga aacagaccca ttgatatatg taagtgacct   4740
atgaaaaaaa tatggcattt tacaatggga aaatgatggt ctttttcttt tttagaaaaa   4800
cagggaaata tatttatatg taaaaaataa aagggaaccc atatgtcata ccatacacac   4860
aaaaaaattc cagtgaatta taagtctaaa tggagaaggc aaaactttaa atcttttaga   4920
aaataatata gaagcatgca gaccagcctg gccaacatga tgaaaccctc tctactaata   4980
ataaaatcag tagaactact caggactact ttgagtggga agtccttttc tatgaagact   5040
tctttggcca aaattaggct ctaaatgcaa ggagatagtg catcatgcct ggctgcactt   5100
actgataaat gatgttatca ccatctttaa ccaaatgcac aggaacaagt tatggtactg   5160
atgtgctgga ttgagaagga gctctacttc cttgacagga cacatttgta tcaacttaaa   5220
aaagcagatt tttgccagca gaactattca ttcagaggta ggaaacttag aatagatgat   5280
gtcactgatt agcatggctt ccccatctcc acagctgctt cccacccagg ttgcccacag   5340
ttgagtttgt ccagtgctca gggctgccca ctctcagtaa gaagccccac accagcccct   5400
ctccaaatat gttggctgtt ccttccatta aagtgacccc actttagagc agcaagtgga   5460
tttctgtttc ttacagttca ggaaggagga gtcagctgtg agaacctgga gcctgagatg   5520
cttctaagtc ccactgctac tggggtcagg gaagccagac tccagcatca gcagtcagga   5580
gcactaagcc cttgccaaca tcctgtttct cagagaaact gcttccatta taatggttgt   5640
ccttttttaa gctatcaagc caaacaacca gtgtctacca ttattctcat cacctgaagc   5700
caagggttct agcaaaagtc aagctgtctt gtaatggttg atgtgcctcc agcttctgtc   5760
ttcagtcact ccactcttag cctgctctga atcaactctg accacagttc cctggagccc   5820
ctgccacctg ctgcccctgc caccttctcc atctgcagtg ctgtgcagcc ttctgcactc   5880
ttgcagagct aataggtgga gacttgaagg aagaggagga aagtttctca taatagcctt   5940
gctgcaagct caaatgggag gtgggcactg tgcccaggag ccttggagca aaggctgtgc   6000
ccaacctctg actgcatcca ggtttggtct tgacagagat aagaagccct ggcttttgga   6060
gccaaaatct aggtcagact taggcaggat tctcaaagtt tatcagcaga acatgaggca   6120
gaagaccctt tctgctccag cttcttcagg ctcaaccttc atcagaatag atagaaagag   6180
aggctgtgag ggttcttaaa acagaagcaa atctgactca gagaataaac aacctcctag   6240
taaactacag cttagacaga gcatctggtg gtgagtgtgc tcagtgtcct actcaactgt   6300
ctggtatcag ccctcatgag gacttctctt ctttccctca tagacctcca tctctgtttt   6360
ccttagcctg cagaaatctg gatggctatt cacagaatgc ctgtgctttc agagttgcat   6420
tttttctctg gtattctggt tcaagcattt gaaggtagga aaggttctcc aagtgcaaga   6480
aagccagccc tgagcctcaa ctgcctggct agtgtggtca gtaggatgca aaggctgttg   6540
aatgccacaa ggccaaactt taacctgtgt accacaagcc tagcagcaga ggcagctctg   6600
ctcactggaa ctctctgtct tctttctcct gagccttttc ttttcctgag ttttctagct   6660
ctcctcaacc ttacctctgc cctacccagg acaaacccaa gagccactgt ttctgtgatg   6720
tcctctccag ccctaattag gcatcatgac ttcagcctga ccttccatgc tcagaagcag   6780
tgctaatcca cttcagatga gctgctctat gcaacacagg cagagcctac aaacctttgc   6840
accagagccc tccacatatc agtgtttgtt catactcact tcaacagcaa atgtgactgc   6900
tgagattaag attttacaca agatggtctg taatttcaca gttagtttta tcccattagg   6960
tatgaaagaa ttagcataat tccccttaaa catgaatgaa tcttagattt tttaataaat   7020
agttttggaa gtaaagacag agacatcagg agcacaagga atagcctgag aggacaaaca   7080
```

gaacaagaaa gagtctggaa atacacagga tgttcttggc ctcctcaaag caagtgcaag 7140
cagatagtac cagcagcccc aggctatcag agcccagtga agagaagtac catgaaagcc 7200
acagctctaa ccaccctgtt ccagagtgac agacagtccc caagacaagc cagcctgagc 7260
cagagagaga actgcaagag aaagtttcta atttaggttc tgttagattc agacaagtgc 7320
aggtcatcct ctctccacag ctactcacct ctccagccta acaaagcctg cagtccacac 7380
tccaaccctg gtgtctcacc tcctagcctc tcccaacatc ctgctctctg accatcttct 7440
gcatctctca tctcaccatc tcccactgtc tacagcctac tcttgcaact accatctcat 7500
tttctgacat cctgtctaca tcttctgcca tactctgcca tctaccatac cacctcttac 7560
catctaccac accatctttt atctccatcc ctctcagaag cctccaagct gaatcctgct 7620
ttatgtgttc atctcagccc ctgcatggaa agctgacccc agaggcagaa ctattcccag 7680
agagcttggc caagaaaaac aaaactacca gcctggccag gctcaggagt agtaagctgc 7740
agtgtctgtt gtgttctagc ttcaacagct gcaggagttc cactctcaaa tgctccacat 7800
ttctcacatc ctcctgattc tggtcactac ccatcttcaa agaacagaat atctcacatc 7860
agcatactgt gaaggactag tcatgggtgc agctgctcag agctgcaaag tcattctgga 7920
tggtggagag cttacaaaca tttcatgatg ctccccccgc tctgatggct ggagcccaat 7980
ccctacacag actcctgctg tatgtgtttt cctttcactc tgagccacag ccagagggca 8040
ggcattcagt ctcctcttca ggctggggct ggggcactga gaactcaccc aacaccttgc 8100
tctcactcct tctgcaaaac aagaaagagc tttgtgctgc agtagccatg aagaatgaaa 8160
ggaaggcttt aactaaaaaa tgtcagagat tattttcaac cccttactgt ggatcaccag 8220
caaggaggaa acacaacaca gagacatttt ttcccctcaa attatcaaaa gaatcactgc 8280
atttgttaaa gagagcaact gaatcaggaa gcagagtttt gaacatatca gaagttagga 8340
atctgcatca gagacaaatg cagtcatggt tgtttgctgc ataccagccc taatcattag 8400
aagcctcatg gacttcaaac atcattccct ctgacaagat gctctagcct aactccatga 8460
gataaaataa atctgccttt cagagccaaa gaagagtcca ccagcttctt ctcagtgtga 8520
acaagagctc cagtcaggtt agtcagtcca gtgcagtaga ggagaccagt ctgcatcctc 8580
taattttcaa aggcaagaag atttgtttac cctggacacc aggcacaagt gaggtcacag 8640
agctcttaga tatgcagtcc tcatgagtga ggagactaaa gcgcatgcca tcaagacttc 8700
agtgtagaga aaacctccaa aaaagcctcc tcactacttc tggaatagct cagaggccga 8760
ggcggcctcg gcctctgcat aaataaaaaa aattagtcag ccatggggcg gagaatgggc 8820
ggaactgggc ggagttaggg gcgggatggg cggagttagg ggcgggacta tggttgctga 8880
ctaattgaga tgcatgcttt gcatacttct gcctgctggg gagcctgggg actttccaca 8940
cctggttgct gactaattga gatgcatgct ttgcatactt ctgcctgctg gggagcctgg 9000
ggactttcca caccctaact gacacacatt ccacagctgc attaatgaat cggccaacgc 9060
gcggggagag gcggtttgcg tattgggcgc tcttccgctt cctcgctcac tgactcgctg 9120
cgctcggtcg ttcggctgcg gcgagcggta tcagctcact caaaggcggt aatacggtta 9180
tccacagaat caggggataa cgcaggaaag aacatgtgag caaaaggcca gcaaaaggcc 9240
aggaaccgta aaaaggccgc gttgctggcg tttttccata ggctccgccc ccctgacgag 9300
catcacaaaa atcgacgctc aagtcagagg tggcgaaacc cgacaggact ataaagatac 9360
caggcgtttc cccctggaag ctccctcgtg cgctctcctg ttccgaccct gccgcttacc 9420

```
ggatacctgt ccgcctttct cccttcggga agcgtggcgc tttctcatag ctcacgctgt   9480

aggtatctca gttcggtgta ggtcgttcgc tccaagctgg gctgtgtgca cgaacccccc   9540

gttcagcccg accgctgcgc cttatccggt aactatcgtc ttgagtccaa cccggtaaga   9600

cacgacttat cgccactggc agcagccact ggtaacagga ttagcagagc gaggtatgta   9660

ggcggtgcta cagagttctt gaagtggtgg cctaactacg gctacactag aagaacagta   9720

tttggtatct gcgctctgct gaagccagtt accttcggaa aaagagttgg tagctcttga   9780

tccggcaaac aaaccaccgc tggtagcggt ggtttttttg tttgcaagca gcagattacg   9840

cgcagaaaaa aaggatctca agaagatcct ttgatctttt ctacggggtc tgacgctcag   9900

tggaacgaaa actcacgtta agggattttg gtcatgagat tatcaaaaag gatcttcacc   9960

tagatccttt taaattaaaa atgaagtttt aaatcaatct aaagtatata tgagtaaact  10020

tggtctgaca gttaccaatg cttaatcagt gaggcaccta tctcagcgat ctgtctattt  10080

cgttcatcca tagttgcctg actcctgcaa accacgttgt gtctcaaaat ctctgatgtt  10140

acattgcaca agataaaaat atatcatcat gaacaataaa actgtctgct tacataaaca  10200

gtaatacaag gggtgttatg agccatattc aacgggaaac gtcttgctcg aggccgcgat  10260

taaattccaa catggatgct gatttatatg ggtataaatg ggctcgcgat aatgtcgggc  10320

aatcaggtgc gacaatctat cgattgtatg ggaagcccga tgcgccagag ttgtttctga  10380

aacatggcaa aggtagcgtt gccaatgatg ttacagatga gatggtcaga ctaaactggc  10440

tgacggaatt tatgcctctt ccgaccatca agcattttat ccgtactcct gatgatgcat  10500

ggttactcac cactgcgatc cccgggaaaa cagcattcca ggtattagaa gaatatcctg  10560

attcaggtga aaatattgtt gatgcgctgg cagtgttcct gcgccggttg cattcgattc  10620

ctgtttgtaa ttgtcctttt aacagcgatc gcgtatttcg tctcgctcag gcgcaatcac  10680

gaatgaataa cggtttggtt gatgcgagtg attttgatga cgagcgtaat ggctggcctg  10740

ttgaacaagt ctggaaagaa atgcataagc ttttgccatt ctcaccggat tcagtcgtca  10800

ctcatggtga tttctcactt gataacctta tttttgacga ggggaaatta ataggttgta  10860

ttgatgttgg acgagtcgga atcgcagacc gataccagga tcttgccatc ctatggaact  10920

gcctcggtga gttttctcct tcattacaga aacggctttt tcaaaaatat ggtattgata  10980

atcctgatat gaataaattg cagtttcatt tgatgctcga tgagtttttc taagggcggc  11040

ctgccaccat acccacgccg aaacaagcgc tcatgagccc gaagtggcga gcccgatctt  11100

ccccatcggt gatgtcggcg atataggcgc cagcaaccgc acctgtggcg ccggtgatga  11160

gggcgcgcca agtcgacgtc cggcagtc                                     11188
```

<210> SEQ ID NO 12
<211> LENGTH: 11187
<212> TYPE: DNA
<213> ORGANISM: Artificial Sequence
<220> FEATURE:
<223> OTHER INFORMATION: Synthetic polynucleotide

<400> SEQUENCE: 12

```
ctagaaccgg tgacgtctcc catggtgaag cttggatctg aattcggtac ctagttataa     60

tagtaatcaa ttacggggtc attagttcat agcccatata tggagttccg cgttacataa    120

cttacggtaa atggcccgcc tggctgaccg cccaacgacc cccgcccatt gacgtcaata    180

atgacgtatg ttcccatagt aacgccaata gggactttcc attgacgtca atgggtggag    240

tatttacggt aaactgccca cttggcagta catcaagtgt atcatatgcc aagtacgccc    300
```

-continued

```
cctattgacg tcaatgacgg taaatggccc gcctggcatt atgcccagta catgacctta    360
tgggactttc ctacttggca gtacatctac gtattagtca tcgctattac catggtcgag    420
gtgagcccca cgttctgctt cactctcccc atctcccccc cctccccacc cccaattttg    480
tatttattta tttttaatt attttgtgca gcgatggggg cggggggggg gggggggcgc    540
gcgccaggcg gggcggggcg gggcgagggg cggggcgggg cgaggcggag aggtgcggcg    600
gcagccaatc agagcggcgc gctccgaaag tttcctttta tggcgaggcg gcggcggcgg    660
cggccctata aaaagcgaag cgcgcggcgg gcgggagtcg ctgcgacgct gccttcgccc    720
cgtgccccgc tccgccgccg cctcgcgccg cccgccccgg ctctgactga ccgcgttact    780
cccacaggtg agcgggcggg acggcccttc tcctccgggc tgtaattagc gcttggttta    840
atgacggctt gtttcttttc tgtggctgcg tgaaagcctt gaggggctcc gggagctaga    900
gcctctgcta accatgttca tgccttcttc tttttcctac agctcctggg caacgtgctg    960
gttattgtgc tgtctcatca ttttggcaaa gaattcctcg aagatccgaa gggaaagtct   1020
tccacgactg tgggatccgt tcgaagatat caccggttga gccaccatgg aattcagcag   1080
ccccagcaga gaggaatgcc ccaagcctct gagccgggtg tcaatcatgg ccggatctct   1140
gacaggactg ctgctgcttc aggccgtgtc ttgggcttct ggcgctagac cttgcatccc   1200
caagagcttc ggctacagca gcgtcgtgtg cgtgtgcaat gccacctact gcgacagctt   1260
cgaccctcct acctttcctg ctctgggcac cttcagcaga tacgagagca ccagatccgg   1320
cagacggatg gaactgagca tgggacccat ccaggccaat cacacaggca ctggcctgct   1380
gctgacactg cagcctgagc agaaattcca gaaagtgaaa ggcttcggcg gagccatgac   1440
agatgccgcc gctctgaata tcctggctct gtctccacca gctcagaacc tgctgctcaa   1500
gagctacttc agcgaggaag gcatcggcta caacatcatc agagtgccca tggccagctg   1560
cgacttcagc atcaggacct acacctacgc cgacacaccc gacgatttcc agctgcacaa   1620
cttcagcctg cctgaagagg acaccaagct gaagatccct ctgatccaca gagccctgca   1680
gctggcacaa agacccgtgt cactgctggc ctctccatgg acatctccca cctggctgaa   1740
aacaaatggc gccgtgaatg gcaagggcag cctgaaaggc caacctggcg acatctacca   1800
ccagacctgg gccagatact tcgtgaagtt cctggacgcc tatgccgagc acaagctgca   1860
gttttgggcc gtgacagccg agaacgaacc ttctgctgga ctgctgagcg gctacccctt   1920
tcagtgcctg ggctttacac ccgagcacca gcgggacttt atcgcccgtg atctgggacc   1980
cacactggcc aatagcaccc accataatgt gcggctgctg atgctggacg accagagact   2040
gcttctgccc cactgggcta aagtggtgct gacagatcct gaggccgcca aatacgtgca   2100
cggaatcgcc gtgcactggt atctggactt tctggcccct gccaaggcca cactgggaga   2160
gacacacaga ctgttcccca acaccatgct gttcgccagc gaagcctgtg tgggcagcaa   2220
gttttgggaa cagagcgtgc ggctcggcag ctgggataga ggcatgcagt acagccacag   2280
catcatcacc aacctgctgt accacgtcgt cggctggacc gactggaatc tggccctgaa   2340
tcctgaaggc ggccctaact gggtccgaaa cttcgtggac agccccatca tcgtggacat   2400
caccaaggac accttctaca agcagcccat gttctaccac ctgggacact tcagcaagtt   2460
catccccgag ggctctcagc gcgttggact ggtggcttcc cagaagaacg atctggacgc   2520
cgtggctctg atgcaccctg atggatctgc tgtggtggtg gtcctgaacc gcagcagcaa   2580
agatgtgccc ctgaccatca aggatcccgc cgtgggattc ctggaaacaa tcagccctgg   2640
```

-continued

```
ctactccatc cacacctacc tgtggcgtag acagtgacaa ttgttaatta agtttaaacc   2700
ctcgaggccg caagcttatc gataatcaac ctctggatta caaaatttgt gaaagattga   2760
ctggtattct taactatgtt gctcctttta cgctatgtgg atacgctgct ttaatgcctt   2820
tgtatcatgc tattgcttcc cgtatggctt tcattttctc ctccttgtat aaatcctggt   2880
tgctgtctct ttatgaggag ttgtggcccg ttgtcaggca acgtggcgtg gtgtgcactg   2940
tgtttgctga cgcaaccccc actggttggg gcattgccac cacctgtcag ctcctttccg   3000
ggactttcgc tttccccctc cctattgcca cggcggaact catcgccgcc tgccttgccc   3060
gctgctggac aggggctcgg ctgttgggca ctgacaattc cgtggtgttg tcggggaaat   3120
catcgtcctt tccttggctg ctcgcctgtg ttgccacctg gattctgcgc gggacgtcct   3180
tctgctacgt cccttcggcc ctcaatccag cggaccttcc ttcccgcggc ctgctgccgg   3240
ctctgcggcc tcttccgcgt cttcgccttc gccctcagac gagtcggatc tccctttggg   3300
ccgcctcccc gcatcgatac cgtcgactag agctcgctga tcagcctcga ctgtgccttc   3360
tagttgccag ccatctgttg tttgcccctc ccccgtgcct tccttgaccc tggaaggtgc   3420
cactcccact gtcctttcct aataaaatga ggaaattgca tcgcattgtc tgagtaggtg   3480
tcattctatt ctggggggtg gggtggggca ggacagcaag ggggaggatt gggaagacaa   3540
tagcaggcat gctggggaga gatccacgat aacaaacagc tttttggggg tgaacatatt   3600
gactgaattc cctgcaggtt ggccactccc tctctgcgcg ctcgctcgct cactgaggcc   3660
gcccgggcaa agcccgggcg tcgggcgacc tttggtcgcc cggcctcagt gagcgagcga   3720
gcgcgcagag agggagtggc caactccatc actaggggtt cctgcggccg ctcgtacggt   3780
ctcgaggaat tcctgcagga taacttgcca acctcattct aaaatgtata tagaagccca   3840
aaagacaata acaaaaatat tcttgtagaa caaaatggga aagaatgttc cactaaatat   3900
caagatttag agcaaagcat gagatgtgtg gggatagaca gtgaggctga taaaatagag   3960
tagagctcag aaacagaccc attgatatat gtaagtgacc tatgaaaaaa atatggcatt   4020
ttacaatggg aaaatgatgg tctttttctt ttttagaaaa acagggaaat atatttatat   4080
gtaaaaaata aaagggaacc catatgtcat accatacaca caaaaaaatt ccagtgaatt   4140
ataagtctaa atggagaagg caaaacttta aatcttttag aaaataatat agaagcatgc   4200
agaccagcct ggccaacatg atgaaaccct ctctactaat aataaaatca gtagaactac   4260
tcaggactac tttgagtggg aagtcctttt ctatgaagac ttctttggcc aaaattaggc   4320
tctaaatgca aggagatagt gcatcatgcc tggctgcact tactgataaa tgatgttatc   4380
accatcttta accaaatgca caggaacaag ttatggtact gatgtgctgg attgagaagg   4440
agctctactt ccttgacagg acacatttgt atcaacttaa aaaagcagat ttttgccagc   4500
agaactattc attcagaggt aggaaactta gaatagatga tgtcactgat tagcatggct   4560
tccccatctc cacagctgct tcccacccag gttgcccaca gttgagtttg tccagtgctc   4620
agggctgccc actctcagta agaagcccca caccagcccc tctccaaata tgttggctgt   4680
tccttccatt aaagtgaccc cactttagag cagcaagtgg atttctgttt cttacagttc   4740
aggaaggagg agtcagctgt gagaacctgg agcctgagat gcttctaagt cccactgcta   4800
ctggggtcag ggaagccaga ctccagcatc agcagtcagg agcactaagc ccttgccaac   4860
atcctgtttc tcagagaaac tgcttccatt ataatggttg tcctttttta agctatcaag   4920
ccaaacaacc agtgtctacc attattctca tcacctgaag ccaagggttc tagcaaaagt   4980
caagctgtct tgtaatggtt gatgtgcctc cagcttctgt cttcagtcac tccactctta   5040
```

```
gcctgctctg aatcaactct gaccacagtt ccctggagcc cctgccacct gctgcccctg   5100
ccaccttctc catctgcagt gctgtgcagc cttctgcact cttgcagagc taataggtgg   5160
agacttgaag gaagaggagg aaagtttctc ataatagcct tgctgcaagc tcaaatggga   5220
ggtgggcact gtgcccagga gccttggagc aaaggctgtg cccaacctct gactgcatcc   5280
aggtttggtc ttgacagaga taagaagccc tggcttttgg agccaaaatc taggtcagac   5340
ttaggcagga ttctcaaagt ttatcagcag aacatgaggc agaagaccct ttctgctcca   5400
gcttcttcag gctcaacctt catcagaata gatagaaaga gaggctgtga gggttcttaa   5460
aacagaagca aatctgactc agagaataaa caacctccta gtaaactaca gcttagacag   5520
agcatctggt ggtgagtgtg ctcagtgtcc tactcaactg tctggtatca gccctcatga   5580
ggacttctct tctttccctc atagacctcc atctctgttt tccttagcct gcagaaatct   5640
ggatggctat tcacagaatg cctgtgcttt cagagttgca ttttttctct ggtattctgg   5700
ttcaagcatt tgaaggtagg aaaggttctc caagtgcaag aaagccagcc ctgagcctca   5760
actgcctggc tagtgtggtc agtaggatgc aaaggctgtt gaatgccaca aggccaaact   5820
ttaacctgtg taccacaagc ctagcagcag aggcagctct gctcactgga actctctgtc   5880
ttctttctcc tgagcctttt cttttcctga gttttctagc tctcctcaac cttacctctg   5940
ccctacccag gacaaaccca agagccactg tttctgtgat gtcctctcca gccctaatta   6000
ggcatcatga cttcagcctg accttccatg ctcagaagca gtgctaatcc acttcagatg   6060
agctgctcta tgcaacacag gcagagccta caaacctttg caccagagcc ctccacatat   6120
cagtgtttgt tcatactcac ttcaacagca aatgtgactg ctgagattaa gattttacac   6180
aagatggtct gtaatttcac agttagtttt atcccattag gtatgaaaga attagcataa   6240
ttccccttaa acatgaatga atcttagatt ttttaataaa tagttttgga agtaaagaca   6300
gagacatcag gagcacaagg aatagcctga gaggacaaac agaacaagaa agagtctgga   6360
aatacacagg atgttcttgg cctcctcaaa gcaagtgcaa gcagatagta ccagcagccc   6420
caggctatca gagcccagtg aagagaagta ccatgaaagc cacagctcta accaccctgt   6480
tccagagtga cagacagtcc ccaagacaag ccagcctgag ccagagagag aactgcaaga   6540
gaaagtttct aatttaggtt ctgttagatt cagacaagtg caggtcatcc tctctccaca   6600
gctactcacc tctccagcct aacaaagcct gcagtccaca ctccaaccct ggtgtctcac   6660
ctcctagcct ctcccaacat cctgctctct gaccatcttc tgcatctctc atctcaccat   6720
ctcccactgt ctacagccta ctcttgcaac taccatctca ttttctgaca tcctgtctac   6780
atcttctgcc atactctgcc atctaccata ccacctctta ccatctacca caccatcttt   6840
tatctccatc cctctcagaa gcctccaagc tgaatcctgc tttatgtgtt catctcagcc   6900
cctgcatgga aagctgaccc cagaggcaga actattccca gagagcttgg ccaagaaaaa   6960
caaaactacc agcctggcca ggctcaggag tagtaagctg cagtgtctgt tgtgttctag   7020
cttcaacagc tgcaggagtt ccactctcaa atgctccaca tttctcacat cctcctgatt   7080
ctggtcacta cccatcttca aagaacagaa tatctcacat cagcatactg tgaaggacta   7140
gtcatgggtg cagctgctca gagctgcaaa gtcattctgg atggtggaga gcttacaaac   7200
atttcatgat gctccccccg ctctgatggc tggagcccaa tccctacaca gactcctgct   7260
gtatgtgttt tcctttcact ctgagccaca gccagagggc aggcattcag tctcctcttc   7320
aggctggggc tggggcactg agaactcacc caacaccttg ctctcactcc ttctgcaaaa   7380
```

-continued

```
caagaaagag ctttgtgctg cagtagccat gaagaatgaa aggaaggctt taactaaaaa   7440
atgtcagaga ttattttcaa ccccttactg tggatcacca gcaaggagga aacacaacac   7500
agagacattt tttcccctca aattatcaaa agaatcactg catttgttaa agagagcaac   7560
tgaatcagga agcagagttt tgaacatatc agaagttagg aatctgcatc agagacaaat   7620
gcagtcatgg ttgtttgctg cataccagcc ctaatcatta gaagcctcat ggacttcaaa   7680
catcattccc tctgacaaga tgctctagcc taactccatg agataaaata aatctgcctt   7740
tcagagccaa agaagagtcc accagcttct tctcagtgtg aacaagagct ccagtcaggt   7800
tagtcagtcc agtgcagtag aggagaccag tctgcatcct ctaattttca aaggcaagaa   7860
gatttgttta ccctggacac caggcacaag tgaggtcaca gagctcttag atatgcagtc   7920
ctcatgagtg aggagactaa agcgcatgcc atcaagactt cagtgtagag aaaacctcca   7980
aaaaagcctc ctcactactt ctggaatagc tcagaggccg aggcggcctc ggcctctgca   8040
taaataaaaa aaattagtca gccatggggc ggagaatggg cggaactggg cggagttagg   8100
ggcgggatgg gcggagttag gggcgggact atggttgctg actaattgag atgcatgctt   8160
tgcatacttc tgcctgctgg ggagcctggg gactttccac acctggttgc tgactaattg   8220
agatgcatgc tttgcatact tctgcctgct ggggagcctg gggactttcc acaccctaac   8280
tgacacacat tccacagctg cattaatgaa tcggccaacg cgcggggaga ggcggtttgc   8340
gtattgggcg ctcttccgct tcctcgctca ctgactcgct gcgctcggtc gttcggctgc   8400
ggcgagcggt atcagctcac tcaaaggcgg taatacggtt atccacagaa tcaggggata   8460
acgcaggaaa gaacatgtga gcaaaaggcc agcaaaaggc caggaaccgt aaaaaggccg   8520
cgttgctggc gtttttccat aggctccgcc cccctgacga gcatcacaaa aatcgacgct   8580
caagtcagag gtggcgaaac ccgacaggac tataaagata ccaggcgttt ccccctggaa   8640
gctccctcgt gcgctctcct gttccgaccc tgccgcttac cggatacctg tccgcctttc   8700
tcccttcggg aagcgtggcg ctttctcata gctcacgctg taggtatctc agttcggtgt   8760
aggtcgttcg ctccaagctg ggctgtgtgc acgaaccccc cgttcagccc gaccgctgcg   8820
ccttatccgg taactatcgt cttgagtcca acccggtaag acacgactta tcgccactgg   8880
cagcagccac tggtaacagg attagcagag cgaggtatgt aggcggtgct acagagttct   8940
tgaagtggtg gcctaactac ggctacacta gaagaacagt atttggtatc tgcgctctgc   9000
tgaagccagt taccttcgga aaaagagttg gtagctcttg atccggcaaa caaaccaccg   9060
ctggtagcgg tggttttttt gtttgcaagc agcagattac gcgcagaaaa aaaggatctc   9120
aagaagatcc tttgatcttt tctacggggt ctgacgctca gtggaacgaa aactcacgtt   9180
aagggatttt ggtcatgaga ttatcaaaaa ggatcttcac ctagatcctt ttaaattaaa   9240
aatgaagttt taaatcaatc taaagtatat atgagtaaac ttggtctgac agttaccaat   9300
gcttaatcag tgaggcacct atctcagcga tctgtctatt tcgttcatcc atagttgcct   9360
gactcctgca aaccacgttg tgtctcaaaa tctctgatgt tacattgcac aagataaaaa   9420
tatatcatca tgaacaataa aactgtctgc ttacataaac agtaatacaa ggggtgttat   9480
gagccatatt caacgggaaa cgtcttgctc gaggccgcga ttaaattcca acatggatgc   9540
tgatttatat gggtataaat gggctcgcga taatgtcggg caatcaggtg cgacaatcta   9600
tcgattgtat gggaagcccg atgcgccaga gttgtttctg aaacatggca aaggtagcgt   9660
tgccaatgat gttacagatg agatggtcag actaaactgg ctgacggaat ttatgcctct   9720
tccgaccatc aagcatttta tccgtactcc tgatgatgca tggttactca ccactgcgat   9780
```

ccccgggaaa acagcattcc aggtattaga agaatatcct gattcaggtg aaaatattgt 9840
tgatgcgctg gcagtgttcc tgcgccggtt gcattcgatt cctgtttgta attgtccttt 9900
taacagcgat cgcgtatttc gtctcgctca ggcgcaatca cgaatgaata acggtttggt 9960
tgatgcgagt gattttgatg acgagcgtaa tggctggcct gttgaacaag tctggaaaga 10020
aatgcataag cttttgccat tctcaccgga ttcagtcgtc actcatggtg atttctcact 10080
tgataacctt atttttgacg aggggaaatt aataggttgt attgatgttg gacgagtcgg 10140
aatcgcagac cgataccagg atcttgccat cctatggaac tgcctcggtg agttttctcc 10200
ttcattacag aaacggcttt ttcaaaaata tggtattgat aatcctgata tgaataaatt 10260
gcagtttcat ttgatgctcg atgagttttt ctaagggcgg cctgccacca tacccacgcc 10320
gaaacaagcg ctcatgagcc cgaagtggcg agcccgatct tccccatcgg tgatgtcggc 10380
gatataggcg ccagcaaccg cacctgtggc gccggtgatg agggcgcgcc aagtcgacgt 10440
ccggcagtct tggccactcc ctctctgcgc gctcgctcgc tcactgaggc cgggcgacca 10500
aaggtcgccc gacgcccggg ctttgcccgg gcggcctcag tgagcgagcg agcgcgcaga 10560
gagggagtgg ccaactccat cactaggggt tcctgctagc tctgggtatt taagcccgag 10620
tgagcacgca gggtctccat tttgaagcgg gaggttacgc gttcgtcgac tactagtggg 10680
taccagagcg tggtgactga gatgttttct aggaaacaca aaagatacaa aaaagaacac 10740
gtggaaggat agccaaaaag gggggctgcc cccatttcct gcaccccgct gcgatggctg 10800
gcaccatttg gaagacttcg agatacactg ttgagcgcag taagacaaca gtgtatctcg 10860
aagtcttcca gatggggcca gccggtccac tctgtatcca ggccagttct gcaaggcgtt 10920
cgaggaccac ccccctcccc tcgccaccag ggtggtctca tacagaactt ataagattcc 10980
caaatccaaa gacatttcac gtttatggtg atttcccaga acacatagcg acatgcaaat 11040
attgcagggc gccactcccc tgtccctcac agccatcttc ctgccagggc gcacgcgcgc 11100
tgggtgttcc cgcctagtga cactgggccc gcgattcctt ggagcgggtt gatgacgtca 11160
gcgtttccca tggtgaatcc ctaggtt 11187

<210> SEQ ID NO 13
<211> LENGTH: 10960
<212> TYPE: DNA
<213> ORGANISM: Artificial Sequence
<220> FEATURE:
<223> OTHER INFORMATION: Synthetic polynucleotide

<400> SEQUENCE: 13
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
cctagttatt aatagtaatc aattacgggg tcattagttc atagcccata tatggagttc 360
cgcgttacat aacttacggt aaatggcccg cctggctgac cgcccaacga cccccgccca 420
ttgacgtcaa taatgacgta tgttcccata gtaacgccaa tagggacttt ccattgacgt 480
caatgggtgg actatttacg gtaaactgcc cacttggcag tacatcaagt gtatcatatg 540
ccaagtacgc cccctattga cgtcaatgac ggtaaatggc ccgcctggca ttatgcccag 600

-continued

```
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tatttttaa ttattttgtg cagcgatggg ggcgggggg    780
gggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgtcctggt ggcgagggga gggggtggt cctcgaacgc   1140
cttgcagaac tggcctggat acagagtgga ccggctggcc ccatctggaa gacttcgaga   1200
tacactgttg tcttactgcg ctcaacagtg tatctcgaag tcttccaaat ggtgccagcc   1260
atcgcagcgg ggtgcaggaa atgggggcag cccccctttt tggctatcct tccacgtgtt   1320
cttttttgta tcttttgtgt ttcctagaaa acatctcagt caccaccttt ctgtggctgc   1380
gtgaaagcct tgaggggctc cgggagctag agcctctgct aaccatgttc atgccttctt   1440
ctttttccta cagctcctgg gcaacgtgct ggttattgtg ctgtctcatc attttggcaa   1500
agaattcctc gaagatccga agggaaagtc ttccacgact gtgggatccg ttcgaagata   1560
tcaccggttg agccaccatg gaattcagca gccccagcag agaggaatgc cccaagcctc   1620
tgagccgggt gtcaatcatg gccggatctc tgacaggact gctgctgctt caggccgtgt   1680
cttgggcttc tggcgctaga ccttgcatcc ccaagagctt cggctacagc agcgtcgtgt   1740
gcgtgtgcaa tgccacctac tgcgacagct tcgaccctcc tacctttcct gctctgggca   1800
ccttcagcag atacgagagc accagatccg gcagacggat ggaactgagc atgggaccca   1860
tccaggccaa tcacacaggc actggcctgc tgctgacact gcagcctgag cagaaattcc   1920
agaaagtgaa aggcttcggc ggagccatga cagatgccgc cgctctgaat atcctggctc   1980
tgtctccacc agctcagaac ctgctgctca agagctactt cagcgaggaa ggcatcggct   2040
acaacatcat cagagtgccc atggccagct gcgacttcag catcaggacc tacacctacg   2100
ccgacacacc cgacgatttc cagctgcaca acttcagcct gcctgaagag gacaccaagc   2160
tgaagatccc tctgatccac agagccctgc agctggcaca aagacccgtg tcactgctgg   2220
cctctccatg gacatctccc acctggctga aaacaaatgg cgccgtgaat ggcaagggca   2280
gcctgaaagg ccaacctggc gacatctacc accagacctg ggccagatac ttcgtgaagt   2340
tcctggacgc ctatgccgag cacaagctgc agttttgggc cgtgacagcc gagaacgaac   2400
cttctgctgg actgctgagc ggctacccct ttcagtgcct gggctttaca cccgagcacc   2460
agcgggactt tatcgcccgt gatctgggac ccacactggc caatagcacc caccataatg   2520
tgcggctgct gatgctggac gaccagagac tgcttctgcc ccactgggct aaagtggtgc   2580
tgacagatcc tgaggccgcc aaatacgtgc acggaatcgc cgtgcactgg tatctggact   2640
ttctggcccc tgccaaggcc acactgggag agacacacag actgttcccc aacaccatgc   2700
tgttcgccag cgaagcctgt gtgggcagca agttttggga acagagcgtg cggctcggca   2760
gctgggatag aggcatgcag tacagccaca gcatcatcac caacctgctg taccacgtcg   2820
tcggctggac cgactggaat ctggccctga atcctgaagg cggccctaac tgggtccgaa   2880
acttcgtgga cagccccatc atcgtggaca tcaccaagga caccttctac aagcagccca   2940
tgttctacca cctgggacac ttcagcaagt tcatccccga gggctctcag cgcgttggac   3000
```

```
tggtggcttc ccagaagaac gatctggacg ccgtggctct gatgcaccct gatggatctg   3060
ctgtggtggt ggtcctgaac cgcagcagca aagatgtgcc cctgaccatc aaggatcccg   3120
ccgtgggatt cctggaaaca atcagccctg gctactccat ccacacctac ctgtggcgta   3180
gacagtgaca attgttaatt aagtttaaac cctcgaggcc gcaagcttat cgataatcaa   3240
cctctggatt acaaaatttg tgaaagattg actggtattc ttaactatgt tgctcctttt   3300
acgctatgtg gatacgctgc tttaatgcct ttgtatcatg ctattgcttc ccgtatggct   3360
ttcattttct cctccttgta taaatcctgg ttgctgtctc tttatgagga gttgtggccc   3420
gttgtcaggc aacgtggcgt ggtgtgcact gtgtttgctg acgcaacccc cactggttgg   3480
ggcattgcca ccacctgtca gctcctttcc gggactttcg ctttccccct ccctattgcc   3540
acggcggaac tcatcgccgc ctgccttgcc cgctgctgga caggggctcg gctgttgggc   3600
actgacaatt ccgtggtgtt gtcggggaaa tcatcgtcct ttccttggct gctcgcctgt   3660
gttgccacct ggattctgcg cgggacgtcc ttctgctacg tcccttcggc cctcaatcca   3720
gcggaccttc cttcccgcgg cctgctgccg gctctgcggc ctcttccgcg tcttcgcctt   3780
cgccctcaga cgagtcggat ctccctttgg gccgcctccc cgcatcgata ccgtcgacta   3840
gagctcgctg atcagcctcg actgtgcctt ctagttgcca gccatctgtt gtttgcccct   3900
cccccgtgcc ttccttgacc ctggaaggtg ccactcccac tgtcctttcc taataaaatg   3960
aggaaattgc atcgcattgt ctgagtaggt gtcattctat tctggggggt ggggtggggc   4020
aggacagcaa gggggaggat tgggaagaca atagcaggca tgctggggag agatccacga   4080
taacaaacag ctttttgggg gtgaacatat tgactgaatt ccctgcaggt tggccactcc   4140
ctctctgcgc gctcgctcgc tcactgaggc cgcccgggca aagcccgggc gtcgggcgac   4200
ctttggtcgc ccggcctcag tgagcgagcg agcgcgcaga gagggagtgg ccaactccat   4260
cactaggggt tcctgcggcc gctcgtacgg tctcgaggaa ttcctgcagg ataacttgcc   4320
aacctcattc taaaatgtat atagaagccc aaaagacaat aacaaaaata ttcttgtaga   4380
acaaaatggg aaagaatgtt ccactaaata tcaagattta gagcaaagca tgagatgtgt   4440
ggggatagac agtgaggctg ataaaataga gtagagctca gaaacagacc cattgatata   4500
tgtaagtgac ctatgaaaaa aatatggcat tttacaatgg gaaaatgatg gtcttttttct   4560
tttttagaaa aacagggaaa tatatttata tgtaaaaaat aaaagggaac ccatatgtca   4620
taccatacac acaaaaaaat tccagtgaat tataagtcta aatggagaag gcaaaacttt   4680
aaatctttta gaaaataata tagaagcatg cagaccagcc tggccaacat gatgaaaccc   4740
tctctactaa taataaaatc agtagaacta ctcaggacta ctttgagtgg gaagtccttt   4800
tctatgaaga cttctttggc caaaattagg ctctaaatgc aaggagatag tgcatcatgc   4860
ctggctgcac ttactgataa atgatgttat caccatcttt aaccaaatgc acaggaacaa   4920
gttatggtac tgatgtgctg gattgagaag gagctctact tccttgacag gacacatttg   4980
tatcaactta aaaaagcaga tttttgccag cagaactatt cattcagagg taggaaactt   5040
agaatagatg atgtcactga ttagcatggc ttccccatct ccacagctgc ttcccaccca   5100
ggttgcccac agttgagttt gtccagtgct cagggctgcc cactctcagt aagaagcccc   5160
acaccagccc ctctccaaat atgttggctg ttccttccat taaagtgacc ccactttaga   5220
gcagcaagtg gatttctgtt tcttacagtt caggaaggag gagtcagctg tgagaacctg   5280
gagcctgaga tgcttctaag tcccactgct actggggtca gggaagccag actccagcat   5340
```

-continued

```
cagcagtcag gagcactaag cccttgccaa catcctgttt ctcagagaaa ctgcttccat   5400
tataatggtt gtcctttttt aagctatcaa gccaaacaac cagtgtctac cattattctc   5460
atcacctgaa gccaagggtt ctagcaaaag tcaagctgtc ttgtaatggt tgatgtgcct   5520
ccagcttctg tcttcagtca ctccactctt agcctgctct gaatcaactc tgaccacagt   5580
tccctggagc ccctgccacc tgctgcccct gccaccttct ccatctgcag tgctgtgcag   5640
ccttctgcac tcttgcagag ctaataggtg gagacttgaa ggaagaggag gaaagtttct   5700
cataatagcc ttgctgcaag ctcaaatggg aggtgggcac tgtgcccagg agccttggag   5760
caaaggctgt gcccaacctc tgactgcatc caggtttggt cttgacagag ataagaagcc   5820
ctggcttttg gagccaaaat ctaggtcaga cttaggcagg attctcaaag tttatcagca   5880
gaacatgagg cagaagaccc tttctgctcc agcttcttca ggctcaacct tcatcagaat   5940
agatagaaag agaggctgtg agggttctta aaacagaagc aaatctgact cagagaataa   6000
acaacctcct agtaaactac agcttagaca gagcatctgg tggtgagtgt gctcagtgtc   6060
ctactcaact gtctggtatc agccctcatg aggacttctc ttctttccct catagacctc   6120
catctctgtt ttccttagcc tgcagaaatc tggatggcta ttcacagaat gcctgtgctt   6180
tcagagttgc atttttctc tggtattctg gttcaagcat ttgaaggtag gaaaggttct   6240
ccaagtgcaa gaaagccagc cctgagcctc aactgcctgg ctagtgtggt cagtaggatg   6300
caaaggctgt tgaatgccac aaggccaaac tttaacctgt gtaccacaag cctagcagca   6360
gaggcagctc tgctcactgg aactctctgt cttctttctc ctgagccttt tcttttcctg   6420
agttttctag ctctcctcaa ccttacctct gccctaccca ggacaaaccc aagagccact   6480
gtttctgtga tgtcctctcc agccctaatt aggcatcatg acttcagcct gaccttccat   6540
gctcagaagc agtgctaatc cacttcagat gagctgctct atgcaacaca ggcagagcct   6600
acaaaccttt gcaccagagc cctccacata tcagtgtttg ttcatactca cttcaacagc   6660
aaatgtgact gctgagatta agattttaca caagatggtc tgtaatttca cagttagttt   6720
tatcccatta ggtatgaaag aattagcata attcccctta aacatgaatg aatcttagat   6780
tttttaataa atagttttgg aagtaaagac agagacatca ggagcacaag gaatagcctg   6840
agaggacaaa cagaacaaga aagagtctgg aaatacacag gatgttcttg gcctcctcaa   6900
agcaagtgca agcagatagt accagcagcc ccaggctatc agagcccagt gaagagaagt   6960
accatgaaag ccacagctct aaccaccctg ttccagagtg acagacagtc cccaagacaa   7020
gccagcctga gccagagaga gaactgcaag agaaagtttc taatttaggt tctgttagat   7080
tcagacaagt gcaggtcatc ctctctccac agctactcac ctctccagcc taacaaagcc   7140
tgcagtccac actccaaccc tggtgtctca cctcctagcc tctcccaaca tcctgctctc   7200
tgaccatctt ctgcatctct catctcacca tctcccactg tctacagcct actcttgcaa   7260
ctaccatctc attttctgac atcctgtcta catcttctgc catactctgc catctaccat   7320
accacctctt accatctacc acaccatctt ttatctccat ccctctcaga agcctccaag   7380
ctgaatcctg ctttatgtgt tcatctcagc ccctgcatgg aaagctgacc ccagaggcag   7440
aactattccc agagagcttg gccaagaaaa acaaaactac cagcctggcc aggctcagga   7500
gtagtaagct gcagtgtctg ttgtgttcta gcttcaacag ctgcaggagt tccactctca   7560
aatgctccac atttctcaca tcctcctgat tctggtcact acccatcttc aaagaacaga   7620
atatctcaca tcagcatact gtgaaggact agtcatgggt gcagctgctc agagctgcaa   7680
agtcattctg gatggtggag agcttacaaa catttcatga tgctcccccc gctctgatgg   7740
```

-continued

```
ctggagccca atccctacac agactcctgc tgtatgtgtt ttcctttcac tctgagccac   7800
agccagaggg caggcattca gtctcctctt caggctgggg ctggggcact gagaactcac   7860
ccaacacctt gctctcactc cttctgcaaa acaagaaaga gctttgtgct gcagtagcca   7920
tgaagaatga aaggaaggct ttaactaaaa aatgtcagag attattttca acccccttact   7980
gtggatcacc agcaaggagg aaacacaaca cagagacatt ttttcccctc aaattatcaa   8040
aagaatcact gcatttgtta aagagagcaa ctgaatcagg aagcagagtt ttgaacatat   8100
cagaagttag gaatctgcat cagagacaaa tgcagtcatg gttgtttgct gcataccagc   8160
cctaatcatt agaagcctca tggacttcaa acatcattcc ctctgacaag atgctctagc   8220
ctaactccat gagataaaat aaatctgcct ttcagagcca aagaagagtc caccagcttc   8280
ttctcagtgt gaacaagagc tccagtcagg ttagtcagtc cagtgcagta gaggagacca   8340
gtctgcatcc tctaattttc aaaggcaaga agatttgttt accctggaca ccaggcacaa   8400
gtgaggtcac agagctctta gatatgcagt cctcatgagt gaggagacta aagcgcatgc   8460
catcaagact tcagtgtaga gaaaacctcc aaaaaagcct cctcactact tctggaatag   8520
ctcagaggcc gaggcggcct cggcctctgc ataaataaaa aaaattagtc agccatgggg   8580
cggagaatgg gcggaactgg gcggagttag gggcgggatg ggcggagtta ggggcgggac   8640
tatggttgct gactaattga gatgcatgct ttgcatactt ctgcctgctg gggagcctgg   8700
ggactttcca cacctggttg ctgactaatt gagatgcatg ctttgcatac ttctgcctgc   8760
tggggagcct ggggactttc cacaccctaa ctgacacaca ttccacagct gcattaatga   8820
atcggccaac gcgcggggag aggcggtttg cgtattgggc gctcttccgc ttcctcgctc   8880
actgactcgc tgcgctcggt cgttcggctg cggcgagcgg tatcagctca ctcaaaggcg   8940
gtaatacggt tatccacaga atcaggggat aacgcaggaa agaacatgtg agcaaaaggc   9000
cagcaaaagg ccaggaaccg taaaaaggcc gcgttgctgg cgtttttcca taggctccgc   9060
cccccctgacg agcatcacaa aaatcgacgc tcaagtcaga ggtggcgaaa cccgacagga   9120
ctataaagat accaggcgtt tccccctgga agctccctcg tgcgctctcc tgttccgacc   9180
ctgccgctta ccggatacct gtccgccttt ctcccttcgg gaagcgtggc gctttctcat   9240
agctcacgct gtaggtatct cagttcggtg taggtcgttc gctccaagct gggctgtgtg   9300
cacgaacccc ccgttcagcc cgaccgctgc gccttatccg gtaactatcg tcttgagtcc   9360
aacccggtaa gacacgactt atcgccactg gcagcagcca ctggtaacag gattagcaga   9420
gcgaggtatg taggcggtgc tacagagttc ttgaagtggt ggcctaacta cggctacact   9480
agaagaacag tatttggtat ctgcgctctg ctgaagccag ttaccttcgg aaaaagagtt   9540
ggtagctctt gatccggcaa acaaaccacc gctggtagcg gtggtttttt tgtttgcaag   9600
cagcagatta cgcgcagaaa aaaaggatct caagaagatc ctttgatctt ttctacgggg   9660
tctgacgctc agtggaacga aaactcacgt taagggattt tggtcatgag attatcaaaa   9720
aggatcttca cctagatcct tttaaattaa aaatgaagtt ttaaatcaat ctaaagtata   9780
tatgagtaaa cttggtctga cagttaccaa tgcttaatca gtgaggcacc tatctcagcg   9840
atctgtctat ttcgttcatc catagttgcc tgactcctgc aaaccacgtt gtgtctcaaa   9900
atctctgatg ttacattgca caagataaaa atatatcatc atgaacaata aaactgtctg   9960
cttacataaa cagtaataca aggggtgtta tgagccatat tcaacgggaa acgtcttgct  10020
cgaggccgcg attaaattcc aacatggatg ctgatttata tgggtataaa tgggctcgcg  10080
```

```
ataatgtcgg gcaatcaggt gcgacaatct atcgattgta tgggaagccc gatgcgccag  10140

agttgtttct gaaacatggc aaaggtagcg ttgccaatga tgttacagat gagatggtca  10200

gactaaactg gctgacggaa tttatgcctc ttccgaccat caagcatttt atccgtactc  10260

ctgatgatgc atggttactc accactgcga tccccgggaa aacagcattc caggtattag  10320

aagaatatcc tgattcaggt gaaaatattg ttgatgcgct ggcagtgttc ctgcgccggt  10380

tgcattcgat tcctgtttgt aattgtcctt ttaacagcga tcgcgtattt cgtctcgctc  10440

aggcgcaatc acgaatgaat aacggtttgg ttgatgcgag tgattttgat gacgagcgta  10500

atggctggcc tgttgaacaa gtctggaaag aaatgcataa gcttttgcca ttctcaccgg  10560

attcagtcgt cactcatggt gatttctcac ttgataacct tatttttgac gaggggaaat  10620

taataggttg tattgatgtt ggacgagtcg gaatcgcaga ccgataccag gatcttgcca  10680

tcctatggaa ctgcctcggt gagttttctc cttcattaca gaaacggctt tttcaaaaat  10740

atggtattga taatcctgat atgaataaat tgcagtttca tttgatgctc gatgagtttt  10800

tctaagggcg gcctgccacc atacccacgc cgaaacaagc gctcatgagc ccgaagtggc  10860

gagcccgatc ttccccatcg gtgatgtcgg cgatataggc gccagcaacc gcacctgtgg  10920

cgccggtgat gagggcgcgc caagtcgacg tccggcagtc                         10960


<210> SEQ ID NO 14
<211> LENGTH: 536
<212> TYPE: PRT
<213> ORGANISM: Homo sapiens

<400> SEQUENCE: 14

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220
```

-continued

```
Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535
```

<210> SEQ ID NO 15
<211> LENGTH: 1608
<212> TYPE: DNA
<213> ORGANISM: Homo sapiens

<400> SEQUENCE: 15

```
atggaattca gcagccccag cagagaggaa tgccccaagc ctctgagccg ggtgtcaatc      60

atggccggat ctctgacagg actgctgctg cttcaggccg tgtcttgggc ttctggcgct     120

agaccttgca tccccaagag cttcggctac agcagcgtcg tgtgcgtgtg caatgccacc     180

tactgcgaca gcttcgaccc tcctaccttt cctgctctgg gcaccttcag cagatacgag     240

agcaccagat ccggcagacg gatggaactg agcatgggac ccatccaggc caatcacaca     300
```

```
ggcactggcc tgctgctgac actgcagcct gagcagaaat tccagaaagt gaaaggcttc    360

ggcggagcca tgacagatgc cgccgctctg aatatcctgg ctctgtctcc accagctcag    420

aacctgctgc tcaagagcta cttcagcgag gaaggcatcg gctacaacat catcagagtg    480

cccatggcca gctgcgactt cagcatcagg acctacacct acgccgacac acccgacgat    540

ttccagctgc acaacttcag cctgcctgaa gaggacacca agctgaagat ccctctgatc    600

cacagagccc tgcagctggc acaaagaccc gtgtcactgc tggcctctcc atggacatct    660

cccacctggc tgaaaacaaa tggcgccgtg aatggcaagg gcagcctgaa aggccaacct    720

ggcgacatct accaccagac ctgggccaga tacttcgtga agttcctgga cgcctatgcc    780

gagcacaagc tgcagttttg ggccgtgaca gccgagaacg aaccttctgc tggactgctg    840

agcggctacc cctttcagtg cctgggcttt acacccgagc accagcggga ctttatcgcc    900

cgtgatctgg gacccacact ggccaatagc acccaccata atgtgcggct gctgatgctg    960

gacgaccaga gactgcttct gccccactgg gctaaagtgg tgctgacaga tcctgaggcc   1020

gccaaatacg tgcacggaat cgccgtgcac tggtatctgg actttctggc ccctgccaag   1080

gccacactgg gagagacaca cagactgttc cccaacacca tgctgttcgc cagcgaagcc   1140

tgtgtgggca gcaagttttg ggaacagagc gtgcggctcg gcagctggga tagaggcatg   1200

cagtacagcc acagcatcat caccaacctg ctgtaccacg tcgtcggctg gaccgactgg   1260

aatctggccc tgaatcctga aggcggccct aactgggtcc gaaacttcgt ggacagcccc   1320

atcatcgtgg acatcaccaa ggacaccttc tacaagcagc ccatgttcta ccacctggga   1380

cacttcagca agttcatccc cgagggctct cagcgcgttg gactggtggc ttcccagaag   1440

aacgatctgg acgccgtggc tctgatgcac cctgatggat ctgctgtggt ggtggtcctg   1500

aaccgcagca gcaaagatgt gcccctgacc atcaaggatc ccgccgtggg attcctggaa   1560

acaatcagcc ctggctactc catccacacc tacctgtggc gtagacag                1608
```

```
<210> SEQ ID NO 16
<211> LENGTH: 524
<212> TYPE: PRT
<213> ORGANISM: Homo sapiens

<400> SEQUENCE: 16

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140
```

```
Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
    370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
        435                 440                 445

Lys Gln Cys Asp Gln Phe Val Ala Glu Tyr Glu Pro Val Leu Ile Glu
    450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
        515                 520
```

<210> SEQ ID NO 17
<211> LENGTH: 1572
<212> TYPE: DNA
<213> ORGANISM: Homo sapiens

<400> SEQUENCE: 17

-continued

```
atgtacgccc tgttcctgct ggccagcctg ctgggcgccg ccctggccgg ccccgtgctg     60

ggcctgaagg agtgcacccg cggcagcgcc gtgtggtgcc agaacgtgaa gaccgccagc    120

gactgcggcg ccgtgaagca ctgcctgcag accgtgtgga acaagcccac cgtgaagagc    180

ctgccctgcg acatctgcaa ggacgtggtg accgccgccg gcgacatgct gaaggacaac    240

gccaccgagg aggagatcct ggtgtacctg gagaagacct gcgactggct gcccaagccc    300

aacatgagcg ccagctgcaa ggagatcgtg gacagctacc tgcccgtgat cctggacatc    360

atcaagggcg agatgagccg ccccggcgag gtgtgcagcg ccctgaacct gtgcgagagc    420

ctgcagaagc acctggccga gctgaaccac cagaagcagc tggagagcaa caagatcccc    480

gagctggaca tgaccgaggt ggtggccccc ttcatggcca acatccccct gctgctgtac    540

ccccaggacg gcccccgcag caagccccag cccaaggaca acggcgacgt gtgccaggac    600

tgcatccaga tggtgaccga catccagacc gccgtgcgca ccaacagcac cttcgtgcag    660

gccctggtgg agcacgtgaa ggaggagtgc gaccgcctgg gccccggcat ggccgacatc    720

tgcaagaact acatcagcca gtacagcgag atcgccatcc agatgatgat gcacatgcag    780

cccaaggaga tctgcgccct ggtgggcttc tgcgacgagg tgaaggagat gcccatgcag    840

accctggtgc ccgccaaggt ggccagcaag aacgtgatcc ccgccctgga gctggtggag    900

cccatcaaga agcacgaggt gcccgccaag agcgacgtgt actgcgaggt gtgcgagttc    960

ctggtgaagg aggtgaccaa gctgatcgac aacaacaaga ccgagaagga gatcctggac   1020

gccttcgaca agatgtgcag caagctgccc aagagcctga gcgaggagtg ccaggaggtg   1080

gtggacacct acggcagcag catcctgagc atcctgctgg aggaggtgag ccccgagctg   1140

gtgtgcagca tgctgcacct gtgcagcggc acccgcctgc ccgccctgac cgtgcacgtg   1200

acccagccca aggacggcgg cttctgcgag gtgtgcaaga agctggtggg ctacctggac   1260

cgcaacctgg agaagaacag caccaagcag gagatcctgg ccgccctgga gaagggctgc   1320

agcttcctgc ccgaccccta ccagaagcag tgcgaccagt tcgtggccga gtacgagccc   1380

gtgctgatcg agatcctggt ggaggtgatg gaccccagct tcgtgtgcct gaagatcggc   1440

gcctgcccca gcgcccacaa gcccctgctg ggcaccgaga agtgcatctg gggccccagc   1500

tactggtgcc agaacaccga gaccgccgcc cagtgcaacg ccgtggagca ctgcaagcgc   1560

cacgtgtgga ac                                                       1572
```

<210> SEQ ID NO 18
<211> LENGTH: 478
<212> TYPE: PRT
<213> ORGANISM: Homo sapiens

<400> SEQUENCE: 18

```
Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
```

```
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475
```

<210> SEQ ID NO 19
<211> LENGTH: 1434
<212> TYPE: DNA
<213> ORGANISM: Homo sapiens

<400> SEQUENCE: 19
atgggccgct gctgcttcta caccgccggc accctgagcc tgctgctgct ggtgaccagc 60
gtgaccctgc tggtggcccg cgtgttccag aaggccgtgg accagagcat cgagaagaag 120
atcgtgctgc gcaacggcac cgaggccttc gacagctggg agaagccccc cctgcccgtg 180
tacacccagt tctacttctt caacgtgacc aaccccgagg agatcctgcg cggcgagacc 240
ccccgcgtgg aggaggtggg cccctacacc taccgcgagc tgcgcaacaa ggccaacatc 300
cagttcggcg acaacggcac caccatcagc gccgtgagca acaaggccta cgtgttcgag 360
cgcgaccaga gcgtgggcga ccccaagatc gacctgatcc gcaccctgaa catccccgtg 420
ctgaccgtga tcgagtggag ccaggtgcac ttcctgcgcg agatcatcga ggccatgctg 480
aaggcctacc agcagaagct gttcgtgacc cacaccgtgg acgagctgct gtggggctac 540
aaggacgaga tcctgagcct gatccacgtg ttccgccccg acatcagccc ctacttcggc 600
ctgttctacg agaagaacgg caccaacgac ggcgactacg tgttcctgac cggcgaggac 660
agctacctga acttcaccaa gatcgtggag tggaacggca agaccagcct ggactggtgg 720
atcaccgaca agtgcaacat gatcaacggc accgacggcg acagcttcca ccccctgatc 780
accaaggacg aggtgctgta cgtgttcccc agcgacttct gccgcagcgt gtacatcacc 840
ttcagcgact acgagagcgt gcagggcctg cccgccttcc gctacaaggt gcccgccgag 900
atcctggcca acaccagcga caacgccggc ttctgcatcc ccgagggcaa ctgcctgggc 960
agcggcgtgc tgaacgtgag catctgcaag aacggcgccc ccatcatcat gagcttcccc 1020
cacttctacc aggccgacga gcgcttcgtg agcgccatcg agggcatgca ccccaaccag 1080
gaggaccacg agaccttcgt ggacatcaac cccctgaccg gcatcatcct gaaggccgcc 1140
aagcgcttcc agatcaacat ctacgtgaag aagctggacg acttcgtgga gaccggcgac 1200
atccgcacca tggtgttccc cgtgatgtac ctgaacgaga gcgtgcacat cgacaaggag 1260
accgccagcc gcctgaagag catgatcaac accaccctga tcatcaccaa catcccctac 1320
atcatcatgg ccctgggcgt gttcttcggc ctggtgttca cctggctggc ctgcaagggc 1380
cagggcagca tggacgaggg caccgccgac gagcgcgccc ccctgatccg cacc 1434

<210> SEQ ID NO 20
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 20
tggaagactt cgagatacac tgt 23

<210> SEQ ID NO 21
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 21
acagtgtatc tcgaagtctt cca 23

<210> SEQ ID NO 22
<211> LENGTH: 21
<212> TYPE: DNA

<213> ORGANISM: Artificial Sequence
<220> FEATURE:
<223> OTHER INFORMATION: Synthetic polynucleotide

<400> SEQUENCE: 22
tttagaaata agtggtagtc a 21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
tgactaccac ttatttctaa a 21

<210> SEQ ID NO 24
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 24
agggtatcaa gactacgaa 19

<210> SEQ ID NO 25
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 25
ttcgtagtct tgataccct 19

<210> SEQ ID NO 26
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 26
tattagatct gatggccgc 19

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
ctccatcact aggggttcct 20

<210> SEQ ID NO 28
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 28
agctctgggt atttaagccc gagtgagcac gcagggtctc cattttgaag cgggaggtta 60

-continued

```
<210> SEQ ID NO 29
<211> LENGTH: 145
<212> TYPE: DNA
<213> ORGANISM: Unknown
<220> FEATURE:
<223> OTHER INFORMATION: AAV2 ITR

<400> SEQUENCE: 29

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag agagggagtg gccaa                                          145


<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30

tattagatct gatggccgcg                                                 20


<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31

tccatcacta ggggttcctg                                                 20
```